(12) United States Patent
Tokumasu et al.

(10) Patent No.: US 7,879,863 B2
(45) Date of Patent: Feb. 1, 2011

(54) ANILINE DERIVATIVES

(75) Inventors: Munetaka Tokumasu, Kawasaki (JP);
Masayuki Sugiki, Kawasaki (JP);
Haruko Hirashima, Kawasaki (JP);
Hideki Matsumoto, Kawasaki (JP);
Toshihiko Yoshimura, Kawasaki (JP);
Yasuko Nogi, Kawasaki (JP); Mitsuo Takahashi, Kawasaki (JP); Manabu Kitazawa, Kawasaki (JP); Akiko Oonuki, Kawasaki (JP); Naoyuki Fukuchi, Kawasaki (JP); Yoichiro Shima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 397 days.

(21) Appl. No.: 11/537,139

(22) Filed: Sep. 29, 2006

(65) Prior Publication Data

US 2007/0066586 A1 Mar. 22, 2007

Related U.S. Application Data

(63) Continuation of application No. PCT/JP2005/006834, filed on Mar. 31, 2005.

(30) Foreign Application Priority Data

Mar. 31, 2004 (JP) .............. 2004-107368

(51) Int. Cl.
*A61K 31/52* (2006.01)
*A61K 31/47* (2006.01)
*A61K 31/445* (2006.01)
*A61K 31/44* (2006.01)
*C07D 487/00* (2006.01)
*C07D 215/02* (2006.01)
*C07D 211/68* (2006.01)

(52) U.S. Cl. .............. 514/263.1; 514/357; 514/318; 514/311; 514/258.1; 546/337; 546/194; 546/166; 544/280

(58) Field of Classification Search ............... 564/342; 514/676, 357, 318, 311, 263.1; 544/280; 546/337, 194, 166
See application file for complete search history.

(56) References Cited

U.S. PATENT DOCUMENTS

| 4,271,193 | A | 6/1981 | Liepmann et al. |
| 5,464,820 | A | 11/1995 | Burton et al. |
| 5,534,533 | A | 7/1996 | Ohtani et al. |
| 6,440,937 | B1 | 8/2002 | Baucke et al. |
| 2003/0055031 | A1 | 3/2003 | Hardy et al. |
| 2004/0180925 | A1 | 9/2004 | Matsuno et al. |

FOREIGN PATENT DOCUMENTS

| BR | 9900694 | 3/1999 |
| JP | 55-4397 | 1/1980 |
| JP | 6-501461 | 2/1994 |
| JP | 08-059658 | 3/1996 |
| JP | 8-73404 | 3/1996 |
| WO | WO 92/04371 | 3/1992 |
| WO | WO92/04371 | 3/1992 |
| WO | WO94/29335 | 12/1994 |
| WO | WO94/29336 | 12/1994 |
| WO | WO95/07291 | 3/1995 |
| WO | WO95/21601 | 8/1995 |
| WO | WO97/04779 | 2/1997 |
| WO | WO98/06740 | 2/1998 |
| WO | WO99/37611 | 7/1999 |
| WO | WO01/09165 | 2/2001 |
| WO | WO02/051836 | 7/2002 |
| WO | WO03/002553 | 1/2003 |
| WO | WO03/015784 | 2/2003 |
| WO | WO03/022809 | 3/2003 |
| WO | WO03/028459 | 4/2003 |
| WO | WO03/076458 | 9/2003 |
| WO | WO2004/024710 | 3/2004 |
| WO | WO2004/096302 | 11/2004 |
| WO | WO2005/000824 | 1/2005 |

| WO | WO2006/017538 | 2/2006 |

OTHER PUBLICATIONS

Hcaplus 136:247485, "Preparation of bicyclic pyrrolyl amides as glycogen phosphorylase inhibitors", Bartlett et. al., Mar. 14, 2002.*
Hcaplus 142:295421, "The role of plasma high molecular weight kininogen in experimental intestinal and systematic inflammation", Isordia-Salas et. al.,, 2004.*
Hcaplus 136:247485, Mar. 14, 2002.*
Hcaplus 1993:649935, (1993).*
Patani et. al., "Bioisosterism: A Rational Approach in Drug Design", Chem. Rev., 1996, 96, pp. 3147-3176.*
Hcaplus 1993:649935, "Study on fluorine-containing aromatic heterocyclic compounds. VII. Synthesis of fluorine-containing aza-and thia-dienzo crown compounds", Chen et. al., 1993.*
International Search Report for PCT Patent App. No. PCT/JP2005/006834 (Jul. 12, 2005).
Anderson, K. W., et al., "The First Intermolecular Friedel-Crafts Acylation with β-Lactams," Org. Lett. 2002;4(3):459-461.
Edmont, D., et al., "Synthesis and Evaluation of Quinoline Carboxyguanidines as Antidiabetic Agents," Bioorg. Med. Chem. Lett. 2000;10:1831-1834.
Emim, J. A. da S., et al., "Evidence for activation of the tissue kallikrein-kinin system in nociceptive transmission and inflammatory responses of mice using a specific enzyme inhibitor," Brit. J. Pharincol. 2000;130:1099-1107.
Kwong, F. Y., et al,, "Copper-Catalyzed Coupling of Alkylamines and Aryl Iodides: An Efficient System Even in an Air Atmosphere," Org. Lett. 2002;4(4):581-584.
Ma, D., et al., "Accelerating Effect Induced by the Structure of α-Amino Acid in the Copper-Catalyzed Coupling Reaction of Aryl Halides with α-Amino Acids. Synthesis of Benzolactam-V8," J. Am. Chem. Soc. 1998;120:12459-12467.
Pimenta, D. C., et al., "Design of Inhibitors for Human Tissue Kallikrein Using Non-Natural Aromatic and Basic Amino Acids," Biol. Chem. 2002;383:853-857.
Takahata, H., et al., "A Convenient Synthesis of Monocytic β-Lactams by Means of Solid-Liquid Phase Transfer Reactions," Chem. Pharm. Bull. 1981;29(4):1063-1068.
Supplementary European Search Report for European Patent App. No. 05728768.2 (received May 15, 2009).

* cited by examiner

*Primary Examiner* — Janet L Andres
*Assistant Examiner* — Binta M Robinson
(74) *Attorney, Agent, or Firm* — Shelly Guest Cermak; Cermak Nakajima LLP

(57) ABSTRACT

The present invention provides a novel compound having a kininogenase-inhibitory action and its pharmaceutical use. The compounds are represented by the formulas (A), (B), (C), (E) and (H):

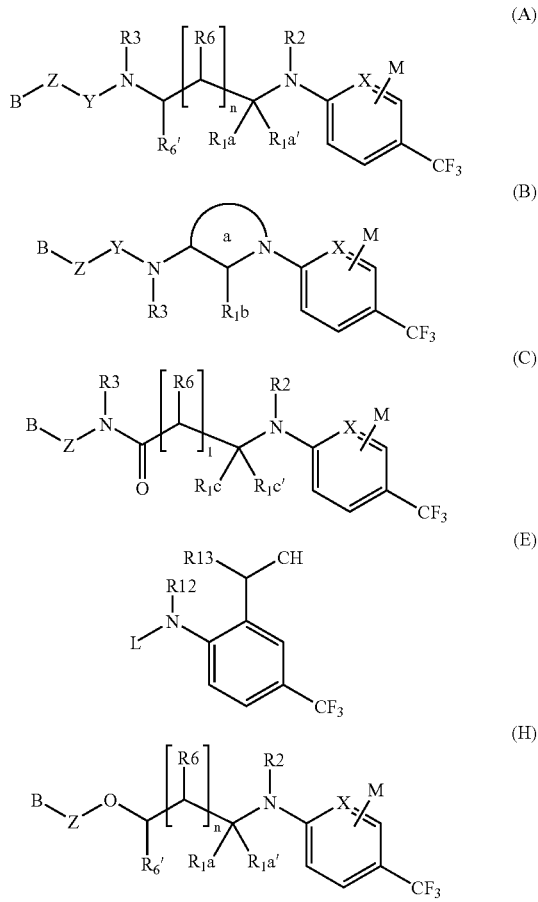

wherein each symbol is as defined in the specification, or a pharmaceutically acceptable salt thereof.

27 Claims, 2 Drawing Sheets

ANILINE DERIVATIVES

This application claims priority under 35 U.S.C. §119 to Japanese Patent Application No. 2004-107368, filed Mar. 31, 2004, and under 35 U.S.C. §120 as a continuation to PCT/JP2005/006834, filed Mar. 31, 2005, the contents of both of which are incorporated by reference in their entireties. The Sequence Listing on Compact Disk filed herewith is also hereby incorporated by reference in its entirety (File Name: US-308 Seq List; File Size: 2 KB; Date Created: Sep. 29, 2006).

BACKGROUND OF THE INVENTION

1. Technical Field

The present invention relates to novel aniline derivatives or salts thereof, production methods thereof, synthetic intermediates therefor, and use of the aniline derivative as a pharmaceutical product. More particularly, the present invention relates to a kininogenase inhibitor (enzyme inhibition) and an agent for the prophylaxis or treatment of various diseases for which the enzyme inhibition is effective.

2. Brief Description of the Related Art

The kallikrein-kinin system plays various physiological functions in living organisms, and functional promotion of a kallikrein-kinin production system is considered to be deeply involved in the pathology of inflammatory allergic diseases such as asthma, rhinitis, arthritis and the like, pain, sepsis, tissue injury and the like (Kinin and angiotensin-molecular mechanism in vivo control, ed. Hisayuki Matsuo, Makoto Katori, Kodansha, Tokyo (1994)). The kallikrein-kinin system is a series of reaction system, wherein the kallikrein enzyme acts on kininogen, a substrate, to cause limited proteolysis, whereby kallidin and bradykinin are produced, then kininase I acts thereon to produce des-$Arg^{10}$-kallidin and des-$Arg^{9}$-bradykinin. These kinins including kallidin, bradykinin, des-$Arg^{10}$-kallidin, des-$Arg^{9}$-bradykinin and the like are active peptides which are physiologically active substances in living organisms, and are known to vary in sensitivity to kinin receptors, depending on the kind of these receptors. As the kallikrein-kinin system reaction pathway, two kinds are known depending on the kind of kallikrein enzyme, which are a plasma kallikrein-kinin system (system wherein plasma kallikrein acts on high molecular weight kininogen) and a tissue kallikrein-kinin system (system wherein tissue kallikrein acts on low molecular weight kininogen). It is assumed that the kinins produced by these pathways act on kinin B2 receptors, which are constitutively expressed in many tissues, to cause most physiological actions, and also act on kinin B1 receptors, which are induced to express by stimulation such as inflammatory response, tissue injury and the like, thus being involved in the retention of inflammatory response and reinforcement algetic reaction associated therewith (*Biochimica et Biophysica Acta*, 1495, 69-77 (2000)). Expression of B1 receptors in the spinal cord of normal mouse is known to be involved in the acute pain during non-inflammation (*PNAS*, 97, 8140-8145 (2000)).

The kinins are peptides that are produced and released from kininogen by limited proteolysis by the above-mentioned kininogenase such as kallikrein and the like, and are endogenous mediators useful for inflammatory reactions. For example, kallidin, bradykinin, des-$Arg^{10}$-kallidin and des-$Arg^{9}$-bradykinin can be mentioned. The main actions thereof are 1) induction of pain, 2) formation of exudates and edema due to increased vascular permeability, 3) contraction of bronchial smooth muscle and intestinal smooth muscle, 4) decreased blood pressure and increased blood flow due to vasodilating action in arteriola, and the like.

The kinins are known to promote production and release of mediators involved in some actions of kinins, such as prostaglandins (PG) etc., by the activation of phospholipase $A_2$. It is known that the PGs themselves do not cause pain or vascular permeability elevating action at a concentration found in inflammatory tissues, but particularly potentiate pain and permeability elevating action when the above-mentioned kinins coexist.

Moreover, involvement of kinins is shown, for example, in the following conditions. Examples of the publications are recited.

1) The state relating to gastrointestinal tract disease: for example, inflammatory bowel disease (*Immunopharmacology*, 43, 103-108 (1999), *Digestive Diseases and Sciences*, 44, 845-851 (1999), *Japanese Journal of Pharmacology*, 90, 59-66 (2002)), and, acute pancreatitis (*British Journal of Pharmacology*, 139, 299-308 (2003), *British Journal of Pharmacology*, 137, 692-700 (2002))

2) The state relating to pain: for example, pain (*Life Sciences*, 61, 1253-1259 (1997), *Brain Research*, 969, 110-116 (2003))

3) The state relating to bronchoconstriction: for example, bronchitis observed in acute allergic reaction in early asthma and inflammatory phase of asthma, and the resulting bronchial obstruction (*European Journal of Pharmacology*, 467, 197-203 (2003), *Am J Physio Lung Cell Mol Physiol*, 286, L734-L740 (2004), *Am Res Respir Dis*, 142, 1367 (1990), *Am Res Respir Dis*, 143, 767 (1991))

4) The state relating to allergic inflammation: for example, particularly allergic rhinitis (*Am Rev Respir Dis*, 137, 613 (1988), *Journal of Clinical Investigation*, 72, 1678 (1983), *Journal of Immunology*, 137, 1323 (1986)) and conjunctivitis (*Infection and Immunity*, 55, 2509 (1987), *Nature*, 337, 385 (1989))

5) The state relating to inflammatory disease: for example, arthritis (*Scand J Rheumatol*, 31, 38-40 (2002), *Pharmacol Ther*, 94, 1-34(2002))

6) The state relating to edematous disease: for example, brain edema (*Brain Res*, 950, 268-278 (2002))

7) The state relating to organ fibrosis: promotion of fibrillization accompanied by collagen production (*Am J Physiol Heart Circ Physiol*, 279, H2829-H2837 (2000), *Journal Biological Chemistry*, 275, 12475-12480 (2000))

8) The state relating to vasodilation and acute hypotension: for example, sepsis, anaphylactic shock and hypovolemic shock; carcinoid syndrome and dumping syndrome (*American Journal of Physiology*, 260, G213 (1991), *Circ Shock*, 27, 93 (1989))

9) The state relating to hemorrhage: for example, hemorrhage (*Ann Thorac Surg*, 68, 473-478 (1999))

10) The state relating to cell proliferative disease: for example, cell proliferative disease (*American Journal of Pathology*, 159, 1797-1805 (2001), *Idrugs*, 6, 581-586 (2003)) and inhibition of neovascularization (*Laboratory Investigation*, 82, 871-880 (2002))

The "kininogenase" is one kind of serine proteases that produce kinins by limited proteolysis of kininogen, a substrate. Several kinds of kininogenase are known, which are largely divided into "tissue kallikrein" and "plasma kallikrein".

(1) The "tissue kallikrein" (TK) is a protein having a molecular weight of about 30,000, and produces and releases kallidin (KD) as a kinin by specifically acting on a low molecular weight kininogen (LMWK), which is a substrate. It is also known that the tissue kallikrein is not present in plasma, but present in various expression tissues. For example, it is found in pancreas, kidney, intestine, salivary gland, urine and the like in human (*Endocrine Reviews*, 22, 184-204 (2001), *Biochemical Journal*, 307, 481-486 (1995)), and rat (*Journal of Biological Chemistry*, 271, 13684-13690 (1996)).

(2) The "plasma kallikrein" (PK) is a protein having a molecular weight of about 100,000, and present in plasma as an inactive enzyme. It is activated by blood coagulation factor XIIa, and produces and releases bradykinin as a kinin by acting on a high molecular weight kininogen, which is a substrate with higher affinity. Plasma kallikrein is quickly and efficiently inhibited by a C1 inactivator and an endogenous inhibitory factor known as $\alpha_2$ macroglobuline.

Kininogen is an endogenous natural substrate of kininogenase enzyme, and is classified into two kinds. (1) The low molecular weight kininogen (LMWK) has a molecular weight within the range of 50,000 to 70,000 depending on the species of origin and formation process of sugar chain.

(2) The high molecular weight kininogen (HMWK) is a protein having a molecular weight within the range of 88,000 to 114,000, and plays a role of a cysteine protease inhibitory factor besides the precursor of kinin.

The above-mentioned two kinds of kininogens are translated from respective mRNAs derived from the same gene and consist of an H chain (Heavy chain or N-terminal), a kinin region and an L chain (Light chain or C-terminal). HMWK has an L chain (molecular weight 45K) longer than an L chain (molecular weight 4.8K) of LMWK, and the two are different on this point.

For example, the detail of the sequence at the cleavage site of human kininogen by plasma kallikrein (PK) and tissue kallikrein (TK) is shown in FIG. 1, and the detail of the cleavage site by kininase I is shown in FIG. 2.

As shown in FIG. 1, when the kinin C-terminal is to be released, PK and TK act on the same cleavage site (I) of the 389th Phe and 390th Arg of human kininogen. On the other hand, when the kinin N-terminal is to be released, PK acts on the cleavage site (II) of the 381st Arg and the 380th Lys to produce bradykinin, and TK acts on the cleavage site (III) of the 379th Met and the 380th Lys to produce kallidin. The bradykinin and kallidin produced in this way act on the kinin B2 receptor to exhibit a physiological action. As shown in FIG. 2, in bradykinin and kallidin, C-terminal Arg is cleaved with kininase I to produce des-Arg$^9$-bradykinin and des-Arg$^{10}$-kallidin, respectively, which mainly act on kinin B1 receptor to exhibit a physiological action.

As an example of a compound having a trifluoromethylaniline-like skeleton, WO2003/022809 discloses a compound represented by the following formula. While the compound of the following formula has a urea bond, the compounds represented by the formulas (A), (B), (C) and (H) of the present invention are markedly different in that the corresponding part is an amide bond, an ether bond and the like. This patent reference describes, moreover, that a compound of the following formula is useful as a therapeutic drug having an analgesic, inflammatory effect via a vanilloid receptor (VR1) antagonistic action. However, the action of the compound of the present invention is based on kininogenase inhibition, and an effect different from the VR1 antagonistic action is expected.

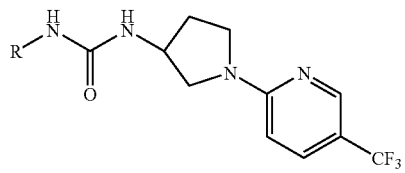

In addition, WO2003/002553 discloses a compound having a dipeptidyl-peptidase IV inhibitory action, which is represented by the following formula, as a therapeutic drug for allergy, inflammation or asthma. However, the compounds represented by the formulas (A), (B), (C) and (H) of the present invention are structurally markedly different in that the amine moiety is an amide bond, an ether bond and the like. This patent reference does not at all describe or suggest the action based on kininogenase inhibition.

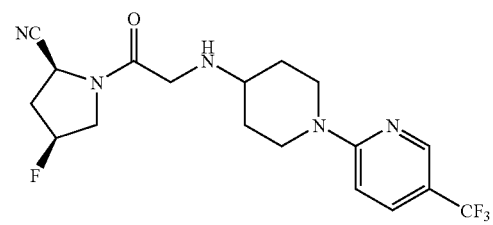

Moreover, WO2002/051836 discloses a compound having a dipeptidyl-peptidase IV inhibitory action, which is represented by the following formula, as a therapeutic drug for inflammatory enteritis or chronic rheumatoid arthritis. However, the compounds represented by the formulas (A), (B), (C) and (H) of the present invention are structurally markedly different in that the amine moiety is an amide bond, an ether bond and the like. This patent reference does not at all describe or suggest the action based on kininogenase inhibition.

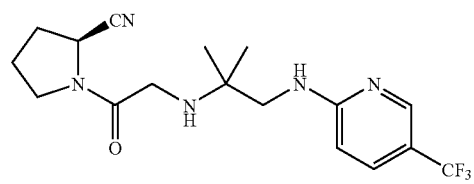

WO97/04779 also discloses a compound having phosphodiesterase IV inhibitory action, which is represented by the following formula, as a therapeutic drug for allergy or inflammation. However, the compounds represented by the formulas (E) and (E') of the present invention are structurally markedly different in that the quinolone moiety is reduced. In addition, this patent reference does not at all describe or suggest the action based on kininogenase inhibition.

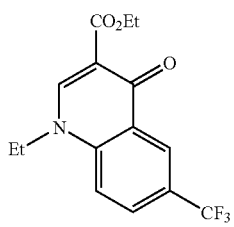

Moreover, the following compound (CAS No. 259196-60-6) is structurally similar to the compounds represented by the formulas (E) and (E') of the present invention and can be purchased as a reagent. However, its use as a pharmaceutical agent is not reported.

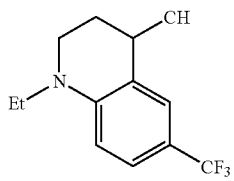

In addition to the above mentioned compounds, various compounds having an aniline-like skeleton have been reported (US2003/0055031; Dawei Ma et al., "*Journal of the American Chemical Society*", (US), 1998, vol. 120, No. 48, pp. 12459-12467; Fuk Yee Kwong et al., "*Organic Letters*", (US), 2002, vol. 4, No. 4, pp. 581-584; Hiroki Takahata et al., "*Chemical & pharmaceutical bulletin*", (JP), 1981, vol. 29, No. 4, pp. 1063-1068; Kevin W. Anderson et al., "*Organic Letters*", (US), 2002, Vol. 4, No. 3, pp. 459-461; Dolores Edmont et al., "*Bioorganic & Medicinal Chemistry Letters*", (UK), 2000, vol. 10, No. 16, pp. 1831-1834). However, these compounds are structurally different from the compounds of the present invention. Furthermore, they have uses which are different from a pharmaceutical agent, and do not envisage the kininogenase inhibitory action of the compounds of the present invention.

SUMMARY OF THE INVENTION

The present invention provides a novel compound having a kininogenase inhibitory action, and use thereof as a pharmaceutical agent. In particular, the present invention provides a pharmaceutical composition containing a compound having a kininogenase inhibitory activity including the compound of the present invention as an active ingredient, and treatment or prophylaxis of a disease for which inhibition of kininogenase is indicated [e.g., gastrointestinal tract diseases (inflammatory bowel disease (IBD), iritable bowel syndrome (IBS), pancreas disease etc.), inflammatory diseases (arthritis, gastritis, pancreatitis, scald, bruise, conjunctivitis, periodontal disease, chronic prostatitis, skin abnormalities (psoriasis, eczema, systemic inflammation reaction syndrome (SIRS) etc.)), fibrosis in organs (liver, kidney, lung, intestine etc.), allergic diseases (asthma, rhinoconjunctivitis (hay fever), rhinorrhea, urticaria etc.), pains (hyperalgesia, migraine, abdominal pain, burn, wound, ablation, rash, bites, insect bite etc.), smooth muscle spasms (asthma, hyperperistalsis, respiratory distress syndrome (RDS) etc.), edematous diseases (burn, brain injury (brain edema), angioneurotic edema etc.), hypotension (shock caused by hemorrhage, sepsis or anaphylaxis, carcinoid syndrome, dumping syndrome etc.), hemorrhage (prevention of excess blood loss during operation, etc.), cell proliferative diseases (cancer (solid tumor, metastatic solid tumor, angiofibroma, myeloma, multiple myeloma, Kaposi's sarcoma etc.) and the like)].

We have conducted intensive studies in an attempt to solve the above-mentioned problem, where we synthesized aniline derivatives, and examined the inhibitory activity thereof in the evaluation system (e.g., enzyme inhibitory activity evaluation of human activated tissue kallikrein) described in the present specification and found that a series of compounds have strong inhibitory activity on kininogenase and confirmed that they are useful as pharmaceutical agents.

The present invention provides a novel aniline derivative that inhibits kininogenase activity, or a salt thereof, and use of the aniline derivative as a pharmaceutical product. One of the subject matters of the present invention is provision of a treatment method (including prophylactic treatment) of various diseases (the above-mentioned various indications), particularly inflammatory bowel disease, irritable bowel syndrome, pancreatitis, asthma, pain and edematous diseases, for which inhibition of kininogenase activity is considered to be effective. One embodiment of the treatment method assumes topical or systemic administration of an effective amount of a kininogenase inhibitor, which is the novel aniline derivative described in the present specification, to patients suffering from the condition of the above-mentioned disease and the like or at a risk of developing the above-mentioned diseased state.

Moreover, the present invention includes a method of preparing a pharmaceutical agent aiming at topical or systemic treatment of the above-mentioned condition, particularly the condition of inflammatory bowel disease, irritable bowel syndrome, pancreatitis, asthma, pain, edematous disease and the like. The pharmaceutical agent contains, as its ingredient, a pharmaceutically acceptable diluent or carrier in combination with a kininogenase inhibitor described in the present specification.

In addition, the present invention provides a pharmaceutical use of a compound having a kininogenase activity inhibitory action, and a novel compound that blocks kinin release from kininogen by selectively inhibiting kininogenase, and furthermore blocks processing of various growth factors or all other actions of these enzymes.

Furthermore, the present invention provides a therapeutic agent for inflammatory bowel disease, which contains a tissue kallikrein inhibitor as an active ingredient.

Accordingly, the present invention provides the following.

(1) A compound represented by any one of the formulas (A), (B) and (C):

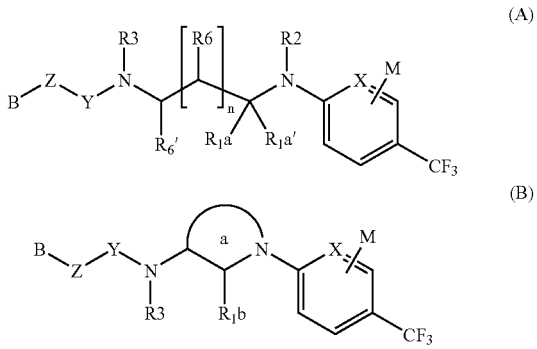

-continued

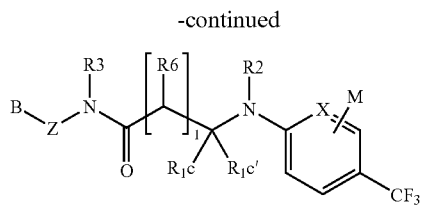 (C)

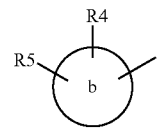 (D)

wherein

X is a carbon atom or a nitrogen atom;

M is selected from the group consisting of a hydrogen atom, a halogeno group, a lower alkyl group optionally having substituent(s), —$(CH_2)_m$ORa, —CH(ORa)(ORa'), —$(CH_2)_m$NRaRa', —$(CH_2)_m$$CO_2$Ra, —$(CH_2)_m$CONRaRa', —CH=CHCO$_2$Ra, —$(CH_2)_m$COCO$_2$Ra and —$(CH_2)_m$PO(ORa)(ORa')

wherein m is an integer of 0 to 2, and

Ra and Ra' are independently selected from the group consisting of a hydrogen atom and a lower alkyl group;

Z is any of a single bond, —CH(Rb)—, —CH(Rb)—CH(Rb')—, —CH=CH— and —C(O)— wherein

Rb and Rb' are independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -QR10 wherein

Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$— and —R11S(O)$_p$— wherein p is an integer of 0 to 2, and

R10 and R11 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;

B is selected from the group consisting of a hydrogen atom, a lower alkyl group optionally having substituent(s) and a group represented by the formula (D):

wherein ring b is selected from the group consisting of a cycloalkyl group, a heterocyclic group and an aryl group, and R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -Q'R20 wherein

Q' is selected from the group consisting of —O—, —S(O)$_{p'}$—, —S(O)$_{p'}$O—, —NH—, —NR21-, —C(=O)—, —C(=O)O—, —C(=O)NH—, —C(=O)NR21-, —S(O)$_{p'}$NH—, —S(O)$_{p'}$NR21-, —NHC(=O)—, —NR21C(=O)—, —NHS(O)$_{p'}$— and —NR21S(O)$_{p'}$— wherein p' is an integer of 0 to 2, and

R20 and R21 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), an acyl group and a hydroxyl group, or R20 and R21 are optionally bonded to form a ring;

R3 is selected from the group consisting of a hydrogen atom, a lower alkyl group optionally having substituent(s) and an aryl group optionally having substituent(s), or R3 is optionally bonded to B to form a nitrogen-containing 5- or 6-membered ring, wherein said nitrogen-containing 5- or 6-membered ring optionally further contains a heteroatom in the ring in addition to the nitrogen atom and is optionally substituted by substituent(s) selected from the group consisting of a hydroxy group, an alkylamino group, an acyl group, a heterocyclic group optionally having substituent(s) and an aryl group optionally having substituent(s); and in the formula (A), Y is —C(O)— or —SO$_2$—;

R$_1$a and R$_1$a' are independently selected from the group consisting of a hydrogen atom, a lower alkyl group optionally having substituent(s) and an aryl group optionally having substituent(s), or R$_1$a and R$_1$a' are optionally bonded to form a 3- to 6-membered ring, wherein said 3- to 6-membered ring optionally contains a heteroatom in the ring and optionally having substituent(s);

R2 is a hydrogen atom or a lower alkyl group, or R$_1$a (or R$_1$a') and R2 are optionally bonded to form a 5- or 6-membered ring, wherein said 5- or 6-membered ring optionally contains a heteroatom in the ring and optionally having substituent(s);

n is 0 or 1; and

R6 and R6' are independently selected from the group consisting of a hydrogen atom, a lower alkyl group optionally having substituent(s), an amino group, an aminoalkyl group and an alkoxy group;

in the formula (B),

Y is —C(O)— or —SO$_2$—;

R$_1$b is a hydrogen atom or a lower alkyl group; and ring a is a nitrogen-containing 5- or 6-membered ring, wherein said nitrogen-containing 5- or 6-membered ring optionally further contains a heteroatom in the ring in addition to the nitrogen atom and optionally having substituent(s); and in the formula (C), R$_1$c and R$_1$c' are independently selected from the group consisting of a hydrogen atom, a lower alkyl group optionally having substituent(s) and an aryl group optionally having substituent(s), or R$_1$c and R$_1$c' are optionally bonded to form a 3- to 6-membered ring, wherein said 3- to 6-membered ring optionally contains a heteroatom in the ring and optionally having substituent(s);

R2 is a hydrogen atom or a lower alkyl group, or R$_1$c (or R$_1$c') and R2 are optionally bonded to form a 5- or 6-membered ring, wherein said 5- or 6-membered ring optionally contains a heteroatom in the ring and optionally having substituent(s);

l is 0 or 1; and

R6 is selected from the group consisting of a hydrogen atom, a lower alkyl group optionally having substituent(s), an amino group, an aminoalkyl group and an alkoxy group, or a pharmaceutically acceptable salt thereof.

(2) The compound of the above-mentioned (1), which is represented by any one of the formulas (A), (B) and (C):

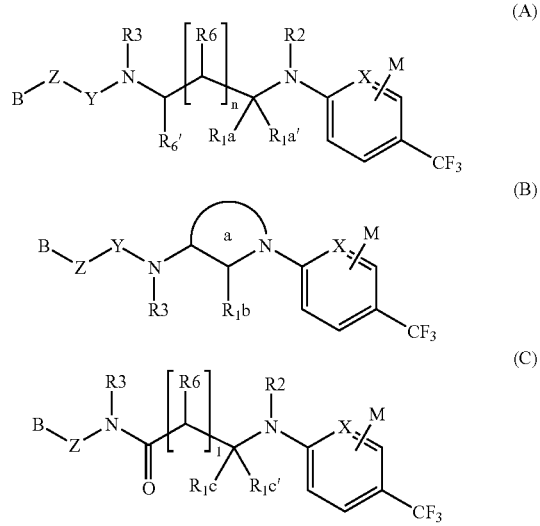

wherein

X is a carbon atom or a nitrogen atom;

M is selected from the group consisting of a hydrogen atom, a halogeno group, a lower alkyl group optionally having substituent(s), —(CH$_2$)$_m$ORa, —CH(ORa)(ORa'), —(CH$_2$)$_m$NRaRa', —(CH$_2$)$_m$CO$_2$Ra, —(CH$_2$)$_m$CONRaRa', —CH═CHCO$_2$Ra, —(CH$_2$)$_m$COCO$_2$Ra and —(CH$_2$)$_m$PO(ORa)(ORa')

wherein m is an integer of 0 to 2, and

Ra and Ra' are independently selected from the group consisting of a hydrogen atom and a lower alkyl group;

Z is any of a single bond, —CH(Rb)—, —CH(Rb)—CH(Rb')— and —CH═CH— wherein

Rb and Rb' are independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -QR10 wherein

Q is selected from the group consisting of —O—, —S(O)$_p$—, —S(O)$_p$O—, —NH—, —NR11-, —C(═O)—, —C(═O)O—, —C(═O)NH—, —C(═O)NR11—, —S(O)$_p$NH—, —S(O)$_p$NR11—, —NHC(═O)—, —NR11C(═O)—, —NHS(O)$_p$— and —R11S(O)$_p$— wherein p is an integer of 0 to 2, and

R10 and R11 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;

B is selected from the group consisting of a hydrogen atom, a lower alkyl group optionally having substituent(s) and a group represented by the formula (D):

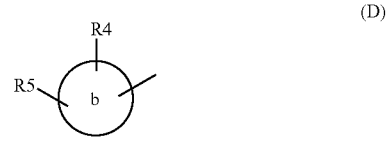

wherein ring b is selected from the group consisting of a cycloalkyl group, a heterocyclic group and an aryl group, and R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -Q'R20 wherein

Q' is selected from the group consisting of —O—, —S(O)$_p$—, —S(O)$_p$O—, —NH—, —NR21-, —C(=O)—, —C(=O)O—, —C(=O)NH—, —C(=O)NR21-, —S(O)$_{p'NH}$—, —S(O)$_p$NR21-, —NHC(=O)—, —NR21C(=O)—, —NHS(O)$_{p'}$— and —NR21S(O)$_{p'}$— wherein p' is an integer of 0 to 2, and

R20 and R21 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R20 and R21 are optionally bonded to form a ring;

R3 is selected from the group consisting of a hydrogen atom and a lower alkyl group; and in the formula (A), Y is —C(O)— or —SO$_2$—;

R$_1$a and R$_1$a' are independently selected from the group consisting of a hydrogen atom and a lower alkyl group optionally having substituent(s), or R$_1$a and R$_1$a' are optionally bonded to form a 3- to 6-membered ring, wherein said 3- to 6-membered ring optionally contains a heteroatom in the ring and optionally having substituent(s);

R2 is a hydrogen atom or a lower alkyl group, or R$_1$a (or R$_1$a') and R2 are optionally bonded to form a 5- or 6-membered ring, wherein said 5- or 6-membered ring optionally contains a heteroatom in the ring and optionally having substituent(s);

n is 0 or 1; and

R6 and R$_6$' are independently selected from the group consisting of a hydrogen atom, a lower alkyl group optionally having substituent(s), an amino group, an aminoalkyl group and an alkoxy group;

in the formula (B),

Y is —C(O)—or —SO$_2$—;

R$_1$b is a hydrogen atom or a lower alkyl group; and ring a is a nitrogen-containing 5- or 6-membered ring, wherein said nitrogen-containing 5 or 6-membered ring optionally further contains a heteroatom in the ring in addition to the nitrogen atom and optionally having substituent(s); and in the formula (C), R$_1$c and R$_1$c' are independently selected from the group consisting of a hydrogen atom and a lower alkyl group optionally having substituent(s), or R$_1$c and R$_1$c' are optionally bonded to form a 3- to 6-membered ring, wherein said 3- to 6-membered ring optionally contains a hetero atom in the ring and optionally having substituent(s);

R2 is a hydrogen atom or a lower alkyl group, or R$_1$c (or R$_1$c') and R2 are optionally bonded to form a 5- or 6-membered ring, wherein said 5- or 6-membered ring optionally contains a heteroatom in the ring and optionally having substituent(s);

l is 0 or 1; and

R6 is selected from the group consisting of a hydrogen atom, a lower alkyl group optionally having substituent(s), an amino group, an aminoalkyl group and an alkoxy group, or a pharmaceutically acceptable salt thereof.

(3) The compound of the above-mentioned (2), wherein X is a carbon atom, or a pharmaceutically acceptable salt thereof.

(4) The compound of the above-mentioned (2) or (3), wherein B is a group represented by the formula (D), or a pharmaceutically acceptable salt thereof.

(5) The compound of any one of the above-mentioned (2) to (4), wherein M is selected from the group consisting of a hydrogen atom, a halogeno group, a lower alkyl group optionally having substituent(s), —(CH$_2$)$_m$ORa, —(CH$_2$)$_m$NRaRa', —(CH$_2$)$_m$CO$_2$Ra and —CH=CHCO$_2$Ra wherein m is an integer of 0 to 2, and Ra and Ra' are independently selected from the group consisting of a hydrogen atom and a lower alkyl group, or a pharmaceutically acceptable salt thereof.

(6) The compound of the above-mentioned (1), which is represented by the formula (A), or a pharmaceutically acceptable salt thereof.

(7) The compound of the above-mentioned (6), wherein B is a group represented by the formula (D), or a pharmaceutically acceptable salt thereof.

(8) The compound of the above-mentioned (6), wherein X is a carbon atom, n is 0, and R2, R3, R6 and R$_6$' are independently selected from the group consisting of a hydrogen atom and a lower alkyl group optionally having substituent(s), or a pharmaceutically acceptable salt thereof.

(9) The compound of the above-mentioned (6), wherein M is selected from the group consisting of a hydrogen atom, a halogeno group and a lower alkyl group optionally having substituent(s), or a pharmaceutically acceptable salt thereof.

(10) The compound of the above-mentioned (6), wherein Y is —C(O)—, or a pharmaceutically acceptable salt thereof.

(11) The compound of the above-mentioned (6), wherein Z is a single bond or —CH(Rb)—, or a pharmaceutically acceptable salt thereof.

(12) The compound of the above-mentioned (6), wherein R$_1$a and R$_1$a' are independently selected from the group consisting of a hydrogen atom and a lower alkyl group optionally having substituent(s), or R$_1$a and R$_1$a' are optionally bonded to form a 3- to 6-membered ring, wherein said 3- to 6-membered ring optionally contains a heteroatom in the ring and optionally having substituent(s), or a pharmaceutically acceptable salt thereof.

(13) The compound of the above-mentioned (6), wherein B is a group represented by the formula (D), and ring b is selected from the group consisting of a phenyl group, a pyridinyl group, an indolyl group and a benzimidazolyl group, or a pharmaceutically acceptable salt thereof.

(14) The compound of the above-mentioned (7), wherein X is a carbon atom, n is 0, and R2, R3, R6 and R$_6$' are independently selected from the group consisting of a hydrogen atom and a lower alkyl group optionally having substituent(s), or a pharmaceutically acceptable salt thereof.

(15) The compound of the above-mentioned (14), wherein M is selected from the group consisting of a hydrogen atom, a halogeno group and a lower alkyl group optionally having substituent(s), or a pharmaceutically acceptable salt thereof.

(16) The compound of the above-mentioned (15), wherein B is a group represented by the formula (D), and ring b is selected from the group consisting of a phenyl group, a pyridinyl group, an indolyl group and a benzimidazolyl group, or a pharmaceutically acceptable salt thereof.

(17) A compound represented by the formula (H):

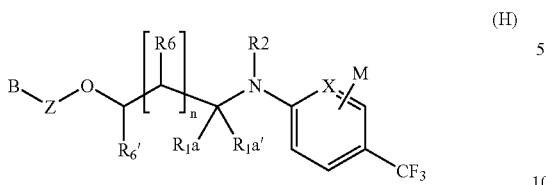

wherein

X is a carbon atom or a nitrogen atom;

M is selected from the group consisting of a hydrogen atom, a halogeno group, a lower alkyl group optionally having substituent(s), —$(CH_2)_m$ORa, —CH(ORa)(ORa'), —$(CH_2)_m$NRaRa', —$(CH_2)_m$CO$_2$Ra, —$(CH_2)_m$CONRaRa', —CH=CHCO$_2$Ra, —$(CH_2)_m$COCO$_2$Ra and —$(CH_2)_m$PO(ORa)(ORa')

wherein m is an integer of 0 to 2, and

Ra and Ra' are independently selected from the group consisting of a hydrogen atom and a lower alkyl group;

Z is selected from the group consisting of a single bond, —CH(Rb)—, —CH(Rb)—CH(Rb')—, —CH=CH— and —C(O)— wherein

Rb and Rb' are independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -QR10 wherein

Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$— and —R11S(O)$_p$— wherein p is an integer of 0 to 2, and

R10 and R11 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;

B is selected from the group consisting of a hydrogen atom, a lower alkyl group optionally having substituent(s) and a group represented by the formula (D):

wherein ring b is selected from the group consisting of a cycloalkyl group, a heterocyclic group and an aryl group, and R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -Q'R20 wherein

Q' is selected from the group consisting of —O—, —S(O)$_{p'}$—, —S(O)$_p$O—, —NH—, —NR21-, —C(=O)—, —C(=O)O—, —C(=O)NH—, —C(=O)NR21-, —S(O)$_{p'}$NH—, —S(O)$_p$NR21-, —NHC(=O)—, —NR21C(=O)—, —NHS(O)$_{p'}$— and —NR21S(O)$_{p'}$— wherein p' is an integer of 0 to 2, and

R20 and R21 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), an acyl group and a hydroxyl group, or R20 and R21 are optionally bonded to form a ring;

$R_1$a and $R_1$a' are independently selected from the group consisting of a hydrogen atom, a lower alkyl group optionally having substituent(s) and an aryl group optionally having substituent(s), or $R_1$a and $R_1$a' are optionally bonded to form a 3- to 6-membered ring, wherein said 3- to 6-membered ring optionally contains a heteroatom in the ring and optionally having substituent(s);

R2 is a hydrogen atom or a lower alkyl group, or $R_1$a (or $R_1$a') and R2 are optionally bonded to form a 5- or 6-membered ring, wherein said 5- or 6-membered ring optionally contains a heteroatom in the ring and optionally having substituent(s);

n is 0 or 1; and

R6 and $R_6$' are independently selected from the group consisting of a hydrogen atom, a lower alkyl group optionally having substituent(s), an amino group, an aminoalkyl group and an alkoxy group, or a pharmaceutically acceptable salt thereof.

(18) The compound of the above-mentioned (17), wherein X is a carbon atom, and B is a group represented by the formula (D), or a pharmaceutically acceptable salt thereof.

(19) The compound of the above-mentioned (17) or (18), wherein M is selected from the group consisting of a hydrogen atom, a halogeno group, a lower alkyl group optionally having substituent(s), —(CH$_2$)$_m$ORa, —(CH$_2$)$_m$NRaRa', —(CH$_2$)$_m$CO$_2$Ra and —CH=CHCO$_2$Ra wherein m is an integer of 0 to 2, and Ra and Ra' are independently selected from the group consisting of a hydrogen atom and a lower alkyl group, or a pharmaceutically acceptable salt thereof.

(20) The compound of the above-mentioned (19), wherein B is a group represented by the formula (D), and ring b is selected from the group consisting of a phenyl group, a pyridinyl group, an indolyl group and a benzimidazolyl group, or a pharmaceutically acceptable salt thereof.

(21) The compound of the above-mentioned (20), wherein R$_1$a and R$_1$a' are independently selected from the group consisting of a hydrogen atom and a lower alkyl group optionally having substituent(s), or R$_1$a and R$_1$a' are optionally bonded to form a 3- to 6-membered ring, wherein said 3- to 6-membered ring optionally contains a heteroatom in the ring and optionally having substituent(s), or a pharmaceutically acceptable salt thereof.

(22) The compound of the above-mentioned (21), wherein n is 0, R2, R6 and R6' are independently selected from the group consisting of a hydrogen atom and a lower alkyl group optionally having substituent(s), and Z is —CH(Rb)— or —CH(Rb)—CH(Rb')—, or a pharmaceutically acceptable salt thereof.

(23) The compound of the above-mentioned (22), wherein B is a group represented by the formula (D), and ring b is selected from the group consisting of a phenyl group, a pyridinyl group, an indolyl group and a benzimidazolyl group, or a pharmaceutically acceptable salt thereof.

(24) A compound represented by the formula (E):

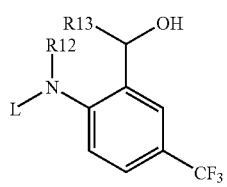

(E)

wherein

R12 is a hydrogen atom or a lower alkyl group, and R13 is a hydrogen atom, or R12 and R13 optionally form, together with the adjacent nitrogen atom and carbon atom, a piperidine ring optionally substituted by 1 or 2 substituents selected from the group consisting of a halogeno group, a lower alkyl group and an alkoxycarbonyl group; and L is selected from the group consisting of an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), a group represented by the formula (F) and a group represented by the formula (G):

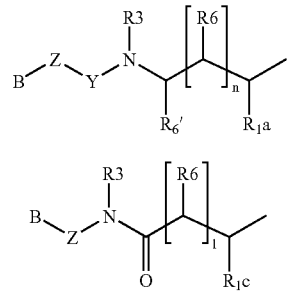

wherein

Z is selected from the group consisting of a single bond, —CH(Rb)—, —CH(Rb)—CH(Rb')— and —CH=CH— wherein

Rb and Rb' are independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -QR10 wherein

Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$— and —R11S(O)$_p$— wherein p is an integer of 0 to 2, and

R10 and R11 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;

B is selected from the group consisting of a hydrogen atom, a lower alkyl group optionally having substituent(s) and a group represented by the formula (D):

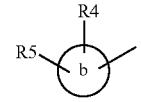

(D)

wherein ring b is selected from the group consisting of a cycloalkyl group, a heterocyclic group and an aryl group, and R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -Q'R20 wherein

Q' is selected from the group consisting of —O—, —S(O)$_p$—, —S(O)$_p$O—, —NH—, —N21-, —C(=O)—, —C(=O)O—, —C(=O)NH—, —C(=O)NR21-, —S(O)$_{p'}$NH—, —S(O)$_p$NR21-, —NHC(=O)—, —NR21C(=O)—, —NHS(O)$_{p'}$— and —NR21S(O)$_{p'}$— wherein p' is an integer of 0 to 2, and

R20 and R21 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R20 and R21 are optionally bonded to form a ring;

R3 is selected from the group consisting of a hydrogen atom and a lower alkyl group; and in the formula (F), Y is —C(O)— or —SO$_2$—;

R$_1$a is a hydrogen atom or a lower alkyl group optionally having substituent(s);

n is 0 or 1; and

R6 and R$_6$' are independently selected from the group consisting of a hydrogen atom, a lower alkyl group optionally having substituent(s), an amino group, an aminoalkyl group and an alkoxy group; and in the formula (G), R$_1$c is a hydrogen atom or a lower alkyl group optionally having substituent(s);

l is 0 or 1; and

R6 is selected from the group consisting of a hydrogen atom, a lower alkyl group optionally having substituent(s), an amino group, an aminoalkyl group and an alkoxy group;

provided that a compound wherein R12 and R13 in combination form an unsubstituted piperidine ring and L is an ethyl group is excluded, or a pharmaceutically acceptable salt thereof.

(25) The compound of the above-mentioned (24), wherein B is a group represented by the formula (D), or a pharmaceutically acceptable salt thereof.

(26) A pharmaceutical agent comprising, as an active ingredient, a compound represented by the formula (E'):

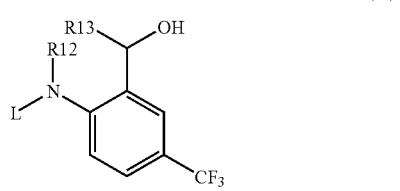

(E')

wherein

R12 is a hydrogen atom or a lower alkyl group, and R13 is a hydrogen atom, or R12 and R13 optionally form, together with the adjacent nitrogen atom and carbon atom, a piperidine ring optionally substituted by 1 or 2 substituents selected from the group consisting of a halogeno group, a lower alkyl group and an alkoxycarbonyl group; and L is selected from the group consisting of an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), a group represented by the formula (F) and a group represented by the formula (G):

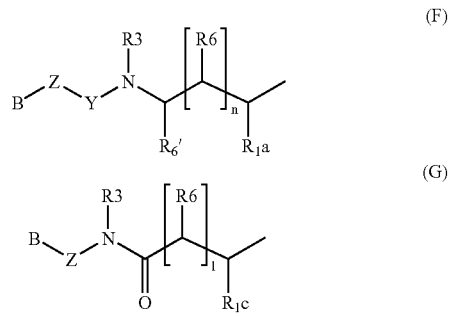

wherein

Z is selected from the group consisting of a single bond, —CH(Rb)—, —CH(Rb)—CH(Rb')— and —CH=CH— wherein

Rb and Rb' are independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -QR10 wherein

Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$— and —R11S(O)$_p$— wherein p is an integer of 0 to 2, and

R10 and R11 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;

B is selected from the group consisting of a hydrogen atom, a lower alkyl group optionally having substituent(s) and a group represented by the formula (D):

(D)

wherein ring b is selected from the group consisting of a cycloalkyl group, a heterocyclic group and an aryl group, and R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and -Q'R20 wherein

Q' is selected from the group consisting of —O—, —S(O)$_{p'}$—, —S(O)$_p$O—, —NH—, —NR21-, —C(=O)—, —C(=O)O—, —C(=O)NH—, —C(=O)NR21-, —S(O)$_{p'}$NH—, —S(O)$_p$NR21-, —NHC(=O)—, —NR21C(=O)—, —NHS(O)$_{p'}$— and —NR21S(O)$_{p'}$— wherein p' is an integer of 0 to 2, and

R20 and R21 are independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R20 and R21 are optionally bonded to form a ring;

R3 is selected from the group consisting of a hydrogen atom and a lower alkyl group; and in the formula (F), Y is —C(O)— or —SO$_2$—;

R$_1$a is a hydrogen atom or a lower alkyl group optionally having substituent(s);

n is 0 or 1; and

R6 and R$_6$' are independently selected from the group consisting of a hydrogen atom, a lower alkyl group optionally having substituent(s), an amino group, an aminoalkyl group and an alkoxy group; and in the formula (G), R$_1$c is a hydrogen atom or a lower alkyl group optionally having substituent(s);

l is 0 or 1; and

R6 is selected from the group consisting of a hydrogen atom, a lower alkyl group optionally having substituent(s), an amino group, an aminoalkyl group and an alkoxy group, or a pharmaceutically acceptable salt thereof.

(27) The pharmaceutical agent of the above-mentioned (26), wherein B is a group represented by the formula (D).

(28) A pharmaceutical agent comprising, as an active ingredient, the compound of any one of in the above-mentioned (1) to (25) or a pharmaceutically acceptable salt thereof.

(29) The pharmaceutical agent of any one of the above-mentioned (26) to (28), wherein said pharmaceutical agent is a kininogenase inhibitor.

(30) The pharmaceutical agent of the above-mentioned (29), wherein said kininogenase is tissue kallikrein.

(31) The pharmaceutical agent of the above-mentioned (29) or (30), wherein said agent is useful for the prophylaxis or treatment of a disease wherein inhibition of kininogenase is indicated.

(32) The pharmaceutical agent of any one of the above-mentioned (26), (28) and (31), wherein said agent is useful for the prophylaxis or treatment of at least one condition selected from the group consisting of a gastrointestinal tract disease, an inflammatory disease, an allergic disease, pain, an edematous disease and a cell proliferative disease.

(33) The pharmaceutical agent of any one of the above-mentioned (26), (28) and (31), wherein said agent is useful for the prophylaxis or treatment of at least one condition selected from the group consisting of an inflammatory bowel disease, an iritable bowel syndrome, pancreatitis and asthma.

(34) A pharmaceutical composition comprising, as an active ingredient, a compound selected from the group consisting of:

the formulas (A), (B) and (C) of the above-mentioned (1);
the formula (H) of the above-mentioned (17);
the formula (E) of the above-mentioned (24);
and the formula (E') of the above-mentioned (26);
or a pharmaceutically acceptable salt thereof,
and a pharmaceutically acceptable carrier.

(35) The pharmaceutical composition of the above-mentioned (34), wherein said pharmaceutical composition is useful for the prophylaxis or treatment of a disease wherein inhibition of kininogenase is indicated.

(36) The pharmaceutical composition of the above-mentioned (34) or (35), wherein said pharmaceutical composition is useful for the prophylaxis or treatment of at least one condition selected from the group consisting of a gastrointestinal tract disease, an inflammatory disease, an allergic disease, pain, an edematous disease and a cell proliferative disease.

(37) The pharmaceutical composition of the above-mentioned (34) or (35), wherein said pharmaceutical composition is useful for the prophylaxis or treatment of at least one condition selected from the group consisting of an inflammatory bowel disease, an iritable bowel syndrome, pancreatitis, asthma, pain and an edematous disease.

(38) A therapeutic agent of an inflammatory bowel disease, comprising a tissue kallikrein inhibitor as an active ingredient.

(39) The therapeutic agent of the above-mentioned (38), wherein the kallikrein inhibitor is the pharmaceutical agent of the above-mentioned (30).

The present invention provides a compound having a kininogenase inhibitory action or a pharmaceutically acceptable salt thereof. The compound is useful as an agent for the treatment or prophylaxis of a disease wherein inhibition of kininogenase is useful for the prophylaxis or treatment thereof, which is specifically a gastrointestinal tract disease (inflammatory bowel disease (IBD), iritable bowel syndrome (IBS), pancreatic disease etc.), an inflammatory disease (arthritis, gastritis, pancreatitis, scald, bruise, conjunctivitis, periodontal disease, chronic prostatitis, skin abnormality (psoriasis, eczema, systemic inflammation reaction syndrome (SIRS) etc.)), fibrosis in organ (liver, kidney, lung, intestine etc.), an allergic disease (asthma, rhinoconjunctivitis (hay fever), rhinorrhea, urticaria etc.), pain (hyperalgesia, migraine, abdominal pain, burn, wound, ablation, rash, bites, insect bite etc.), smooth muscle spasm (asthma, hyperperistalsis, respiratory distress syndrome (RDS) etc.), an edematous disease (burn, brain injury (brain edema), angioneurotic edema etc.), hypotension (shock caused by hemorrhage, sepsis or anaphylaxis, carcinoid syndrome, dumping syndrome etc.), hemorrhage (prevention of excess blood loss during operation etc.), or a cell proliferative disease (cancer (solid tumor, metastatic solid tumor, angiofibroma, myeloma, multiple myeloma, Kaposi's sarcoma etc.)).

Of these, the compound is useful as an agent for the treatment or prophylaxis of a gastrointestinal tract disease, an inflammatory disease, an allergic disease, pain, an edematous disease or a cell proliferative disease, particularly, an inflammatory bowel disease, an irritable bowel syndrome, pancreatitis, asthma, pain or an edematous disease.

The above-mentioned inflammatory bowel disease includes Crohn's disease and ulcerative colitis.

DESCRIPTION OF THE PREFERRED EMBODIMENTS

Figure 1:
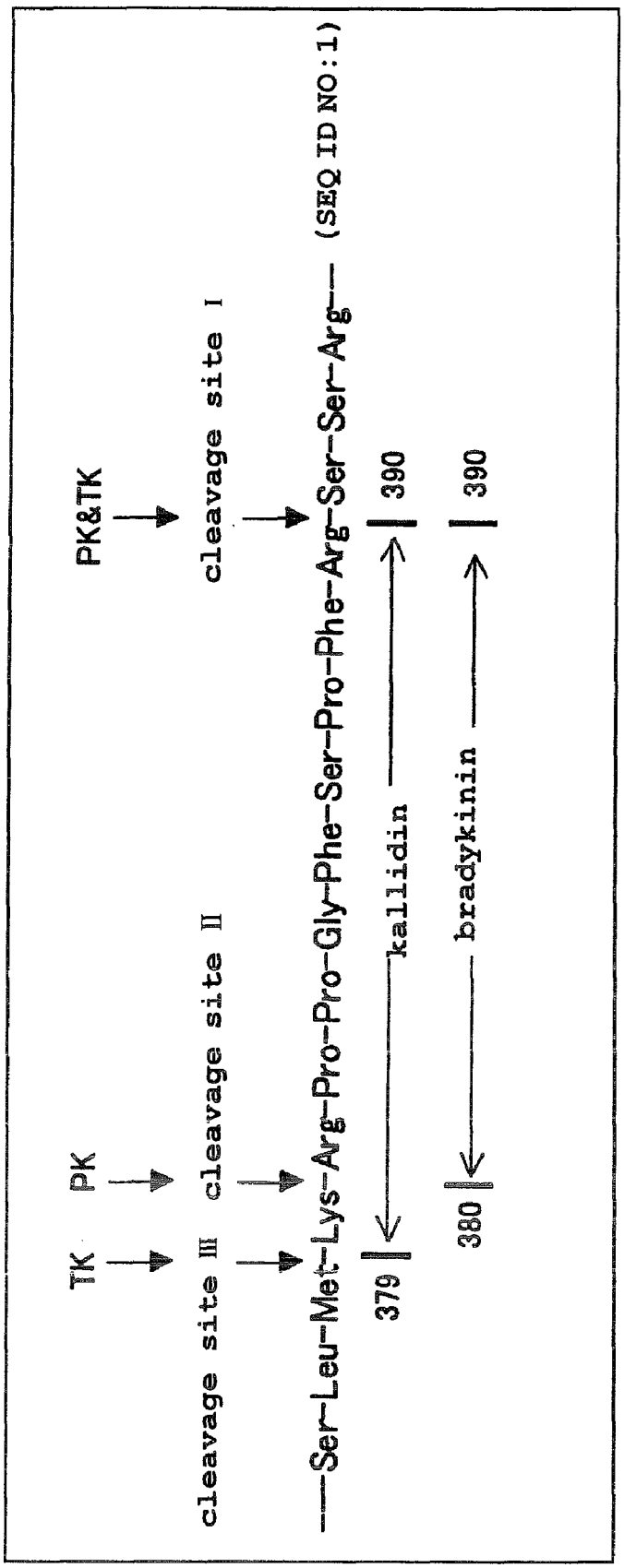
FIG. 1 shows the detail of the sequence at the cleavage site of human kininogen by plasma kallikrein (PK) and tissue kallikrein (TK).
Figure 2:
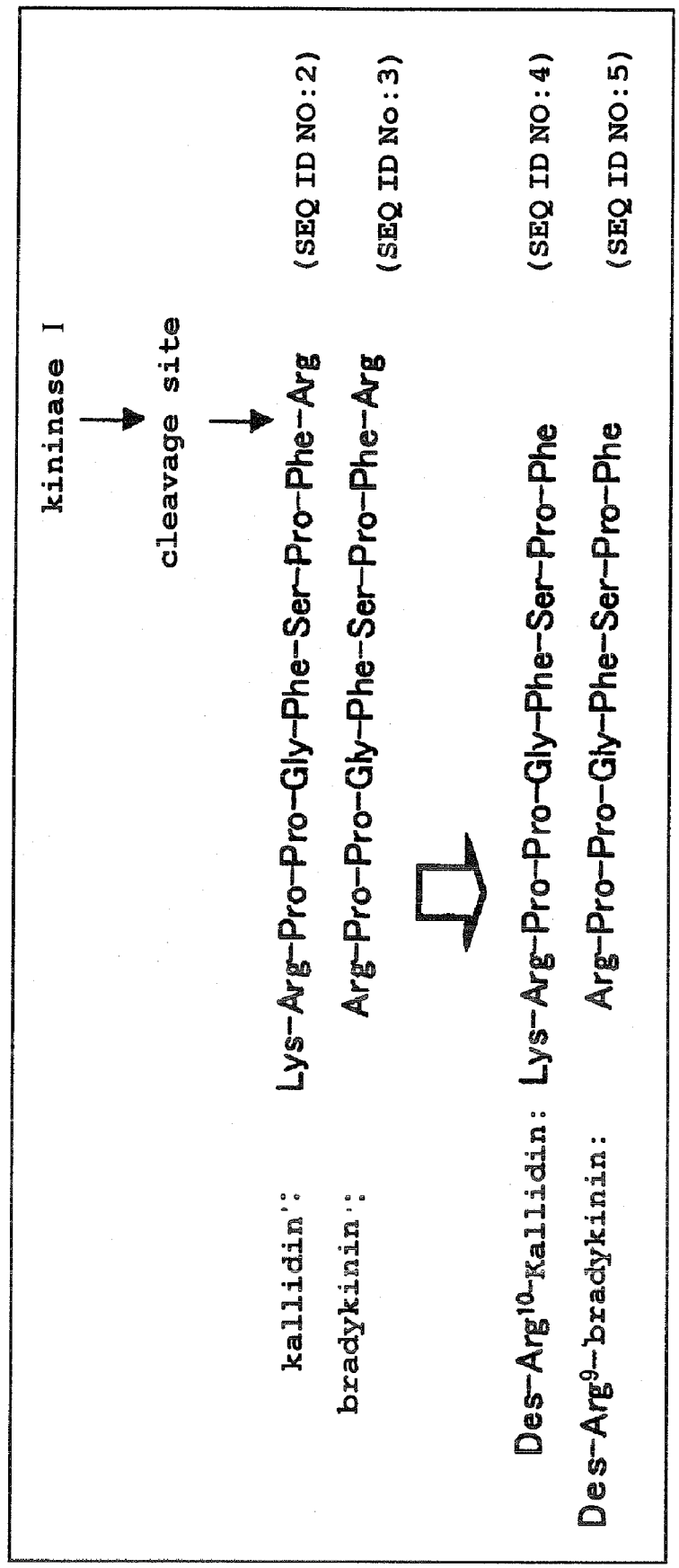
FIG. 2 shows the detail of the sequence at the cleavage site of kallidin and bradykinin by kininase I.

In the present specification, the term "optionally having substituent(s)" means "being substituted or unsubstituted". Unless otherwise specified, the position and number of the substituent(s) are optional, and are not particularly limited. When substituted by two or more substituents, the substituents may be the same or different. As the substituent, for example, an alkyl group, an alkenyl group, an alkynyl group, a halogeno group, a cycloalkyl group, a heterocyclic group, an aryl group, an alkoxy group, a halogenoalkoxy group, a heterocyclyloxy group, an aryloxy group, an aralkyloxy group, an alkylthio group, a heterocyclylthio group, an arylthio group, a nitro group, a cyano group, a hydroxyl group, an acyl group, an oxo group, an amino group, an alkylamino group, an alkylsulfonyl group, a sulfamoyl group, a carboxyl group, an alkoxycarbonyl group, a carbamoyl group, an alkylcarbamoyl group, an acyloxy group, an alkylsulfonylamino group, an arylsulfonylamino group, a hydroxylalkyl group, an alkoxyalkyl group and the like can be mentioned. The definition of each substituent exemplified is given below.

The "halogeno group" can consist of fluorine atom, chlorine atom, bromine atom and iodine atom.

The "alkyl group" is a straight chain or branched chain alkyl group having 1 to 18 carbon atoms or a cyclic alkyl group having 3 to 18 carbon atoms. For example, methyl group, ethyl group, n-propyl group, n-butyl group, n-pentyl group, n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, 2-hexyl group, tert-octyl group, cyclopropyl group, cyclobutyl group, cyclopentyl group, cyclohexyl group, 1-adamantyl group and the like can be mentioned; preferably, n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, 2-hexyl group, tert-octyl group, cyclopropyl group, cyclobutyl group, cyclopentyl group, cyclohexyl group, 1-adamantyl group and the like can be mentioned; and more preferably, isopropyl group, tert-butyl group, tert-octyl group, 1-adamantyl group and the like can be mentioned.

The "lower alkyl group" is a straight chain or branched chain alkyl group having 1 to 6 carbon atoms or a cyclic alkyl group having 3 to 6 carbon atoms, from among the above-mentioned "alkyl groups". For example, methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, cyclopropyl group, cyclobutyl group, cyclopentyl group, cyclohexyl group and the like can be mentioned; and preferably, methyl group, ethyl group, n-propyl group, n-butyl group, n-pentyl group, n-hexyl group, isopropyl group, isobutyl group, sec-butyl group, tert-butyl group, cyclopropyl group, cyclobutyl group and the like can be mentioned.

The "alkenyl group" is an alkenyl group having 2 to 9 carbon atoms, including each isomer. For example, vinyl group, allyl group, propenyl group, butenyl group, pentenyl group, hexenyl group, heptenyl group and the like can be mentioned; and preferably, vinyl group, allyl group, propenyl group and the like can be mentioned.

The "alkynyl group" is an alkynyl group having 2 to 9 carbon atoms, including each isomer. For example, ethynyl, propynyl group, butynyl group, pentynyl group and the like can be mentioned; and preferably, ethynyl, propynyl group and the like can be mentioned.

The "cycloalkyl group" is a nonaromatic cyclic hydrocarbon group having 3 to 10 carbon atoms. For example, cyclopropyl group, cyclobutyl group, cyclopentyl group, cyclohexyl group and the like can be mentioned. When it is represented by R2, R3, R6 or L, cyclopropyl group and cyclobutyl group are preferable. When it is represented by the ring formed by R10 and R11 bonded to each other, or the ring formed by R20 and R21 bonded to each other, cyclopropyl group, cyclobutyl group, cyclopentyl group and cyclohexyl group are preferable.

The "heterocyclic group" is a 5- to 8-membered monocyclic to tricyclic heterocyclic group containing, as a ring atom, 1 to 4 heteroatoms selected from the group consisting of an oxygen atom, a sulfur atom and a nitrogen atom. Any carbon atom to be the ring atom may be substituted by an oxo group, and a sulfur atom or a nitrogen atom may be oxidized to form an oxide. In addition, it may be condensed with a benzene ring. For example, pyridyl group, pyridazinyl group, pyrimidyl group (=pyrimidinyl group), pyrazinyl group, furyl group, thienyl group, pyrrolyl group, isoxazolyl group, oxazolyl group, isothiazolyl group, thiazolyl group, pyrazolyl group, imidazolyl group, oxadiazolyl group, thiadiazolyl group, triazolyl group, tetrazolyl group, benzofuranyl group, benzothienyl group, indolyl group, isoindolyl group, benzoxazolyl group (=benzooxazolyl group), benzothiazolyl group, benzimidazolyl group (=benzoimidazolyl group), indazolyl group, benzisoxazolyl group, benzisothiazolyl group, benzofurazanyl group, benzothiadiazolyl group, purinyl group, quinolyl group (=quinolinyl group), isoquinolyl group, cinnolinyl group, phthalazinyl group, quinazolinyl group, quinoxalinyl group, pteridinyl group, imidazooxazolyl group, imidazothiazolyl group, imidazoimidazolyl group, dibenzofuranyl group, dibenzothienyl group, carbazolyl group, acridinyl group, pyrrolidinyl group, pyrazolidinyl group, imidazolidinyl group, pyrrolinyl group, pyrazolinyl group, imidazolinyl group, tetrahydrofuranyl group, tetrahydrothienyl group, thiazolidinyl group, piperidinyl group (=piperidyl group), piperazinyl group, quinuclidinyl group, tetrahydropyranyl group, tetrahydrothiopyranyl group, morpholinyl group, thiomorpholinyl group, dioxolanyl group, homopiperidinyl group (=homopiperidyl group), homopiperazinyl group, indolinyl group, isoindolinyl group, chromanyl group, isochromanyl group, tetrahydronaphthyridinyl group, azaindolyl group, dioxodihydroindolyl group, tetrahydroquinolyl group, benzotriazolyl group, dioxodihydropurinyl group, azabenzimidazolyl group, oxodihydropyridopyrazinyl group, triazolopyridinyl group, naphthyridinyl group, benzodioxolyl group and the like can be mentioned; preferably, pyridyl group, pyrimidyl group (=pyrimidinyl group), thienyl group, furyl group, pyrrolyl group, oxazolyl group, thiazolyl group, imidazolyl group, benzofuranyl group, benzothienyl group, indolyl group, isoindolyl group, benzothiazolyl group, quinolyl group (=quinolinyl group), isoquinolyl group, pyrrolinyl group, tetrahydrofuranyl group, tetrahydrothienyl group, piperidinyl group (=piperidyl group), piperazinyl group, tetrahydropyranyl group, tetrahydrothiopyranyl group, morpholinyl group, thiomorpholinyl group, homopiperidinyl group (=homopiperidyl group), homopiperazinyl group, dioxodihydroindolyl group, tetrahydroquinolyl group, benzotriazolyl group, dioxodihydropurinyl group, azabenzimidazolyl group, oxodihydropyridopyrazinyl group, triazolopyridinyl group, naphthyridinyl group, benzimidazolyl group, benzodioxolyl group and the like can be mentioned; and more preferably, pyridyl group, thienyl group, furyl group, pyrrolyl group, indolyl group, isoindolyl group, benzothiazolyl group, quinolyl group (=quinolinyl group), isoquinolyl group, pyrrolinyl group, piperidinyl group (=piperidyl group), piperazinyl group, morpholinyl group, homopiperidinyl group (=homopiperidyl group), homopiperazinyl group, tetrahydroquinolyl group, benzimidazolyl group, azabenzimidazolyl group and the like can be mentioned.

The "aryl group" is a monocyclic to tricyclic aromatic hydrocarbon group having 6 to 14 carbon atoms. For example, phenyl group, naphthyl group, anthryl group, phenanthryl group and the like can be mentioned. In addition, the phenyl group may be condensed with a 5- to 8-membered cycloalkyl ring. By condensation, indanyl group, tetrahydronaphthyl group and the like are formed. Preferably, phenyl group, naphthyl group and the like can be mentioned.

The "cycloalkylalkyl group" is an alkyl group (as defined above) substituted by cycloalkyl group(s)(as defined above). For example, cyclopentylmethyl group, cyclopentylethyl group, cyclohexylmethyl group, cyclohexylethyl group and the like can be mentioned; and preferably, cyclopentylmethyl group, cyclohexylmethyl group, cyclopentylethyl group, cyclohexylethyl group and the like can be mentioned.

The "heterocyclylalkyl group" is an alkyl group (as defined above) substituted by heterocycle(s)(as defined above). For example, pyridylmethyl group, pyridylethyl group, thienylmethyl group, benzothienylmethyl group, indolylmethyl group, indolylethyl group, thiazolylmethyl group, isoindolylmethyl group, benzothiazolylmethyl group, quinolylmethyl group, isoquinolylmethyl group, pyrrolidylmethyl group, piperidinylmethyl group, pyrrolinylmethyl group, tetrahydrofuranylmethyl group, tetrahydrothienylmethyl group, piperidinylmethyl group, piperazinylmethyl group and the like can be mentioned; preferably, pyridylmethyl group, thienylmethyl group, indolylmethyl group, indolylethyl group, quinolylmethyl group, pyrrolinylmethyl group, piperidinylmethyl group and the like can be mentioned; and more preferably, pyridylmethyl group, thienylmethyl group, indolylmethyl group, piperidinylmethyl group and the like can be mentioned.

The "aralkyl group" is an alkyl group (as defined above) substituted by aryl group(s)(as defined above). For example, phenylmethyl group (benzyl group), triphenylmethyl group (trityl group), diphenylmethyl group, 2-phenylethyl (phenethyl group), 3-phenylpropyl group, 2-phenylpropyl group, 4-phenylbutyl group, naphthylmethyl group and the like can be mentioned; and preferably, phenylmethyl group (benzyl group), diphenylmethyl group and the like can be mentioned.

The "acyl group" is a formyl group, or an acyl group having a straight chain or branched chain alkyl group having 1 to 6 carbon atoms or a cyclic alkyl group having 3 to 6 carbon atoms (=lower alkyl group; as defined above), an acyl group having an alkenyl group having 2 to 6 carbon atoms, or an acyl group having an optionally substituted aryl group (as defined above). For example, formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group, naphthoyl group and the like can be mentioned; and preferably, acetyl group, propionyl group, butyryl group, isobutyryl group, valeryl group, isovaleryl group, pivaloyl group, benzoyl group and the like can be mentioned.

The "aminoalkyl group" is an alkyl group (as defined above) substituted by amino group(s) or alkylamino group(s) (as defined later). For example, aminomethyl group, aminoethyl group, aminopropyl group, aminoisopropyl group, dimethylaminomethyl group, diethylaminomethyl group and the like can be mentioned; and preferably, aminomethyl group, aminoethyl group, methylaminomethyl group, diethylaminomethyl group and the like can be mentioned.

The "alkoxy group" is an alkoxy group having a straight chain or branched chain alkyl group having 1 to 18 carbon atoms or a cyclic alkyl group having 3 to 18 carbon atoms. For example, methoxy group, ethoxy group, n-propoxy group, n-butoxy group, n-pentyloxy group, n-hexyloxy group, n-heptyloxy group, n-octyloxy group, n-nonyloxy group, n-decyloxy group, n-undecyloxy group, n-dodecyloxy group, isopropoxy group, isobutoxy group, sec-butoxy group, tert-butoxy group, cyclopropyloxy group, cyclobutoxy group, cyclopentyloxy group, cyclohexyloxy group, cycloheptyloxy group, 2-cyclohexylethoxy group, 1-adamantyloxy group, 2-adamantyloxy group, 1-adamantylmethyloxy group, 2-(1-adamantyl)ethyloxy group, trifluoromethoxy group and the like can be mentioned; preferably, methoxy group, ethoxy group, n-propoxy group, n-butoxy group, n-pentyloxy group, n-hexyloxy group, n-dodecyloxy group, isopropoxy group, isobutoxy group, sec-butoxy group, tert-butoxy group, cyclopropyloxy group, cyclopentyloxy group, cyclohexyloxy group, cycloheptyloxy group and the like can be mentioned; and more preferably, methoxy group, ethoxy group, n-propoxy group, n-butoxy group, n-hexyloxy group, isopropoxy group, isobutoxy group, sec-butoxy group, tert-butoxy group and the like can be mentioned.

The "halogenoalkoxy group" is an alkoxy group (as defined above) substituted by halogeno group(s)(as defined above). For example, chloromethoxy group, fluoromethoxy group, chloroethoxy group, fluoroethoxy group, dichloromethoxy group, difluoromethoxy group, trichloromethoxy group, trifluoromethoxy group, bromomethoxy group and the like can be mentioned; preferably, chloromethoxy group, dichloromethoxy group, trichloromethoxy group and trifluoromethoxy group can be mentioned; and more preferably, chloromethoxy group, trifluoromethoxy group and the like can be mentioned.

The "heterocyclyloxy group" is a group having a heterocyclic group (as defined above) on the oxygen atom. For example, 2-pyridyloxy group, 3-pyridyloxy group, 4-pyridyloxy group, 2-pyrimidinyloxy group, 6-quinolyloxy group, 7-quinolyloxy group, 6-isoquinolyloxy group, 7-isoquinolyloxy group, 2-indolyloxy group, 3-indolyloxy group, 4-indolyloxy group, 5-indolyloxy group, 6-indolyloxy group, 7-indolyloxy group, 4-piperidinyloxy group, 3-pyrrolidinyloxy group, tetrahydropyranyloxy group, 4-benzimidazolyloxy group and the like can be mentioned; and preferably, 4-piperidinyloxy group, 3-pyrrolidinyloxy group, 4-benzimidazolyloxy group and the like can be mentioned.

The "aryloxy group" is a group having an aryl group (as defined above) on the oxygen atom. For example, phenoxy group, 1-naphthyloxy group, 2-naphthyloxy group, tetrahydronaphthyloxy group and the like can be mentioned; and preferably, phenoxy group and the like can be mentioned.

The "aralkyloxy group" is a group having an aralkyl group (as defined above) on the oxygen atom. For example, benzyloxy group, trityloxy group, diphenylmethyloxy group, phenethyloxy group and the like can be mentioned; and preferably, benzyloxy group, diphenylmethyloxy group and the like can be mentioned.

The "alkylthio group" is an alkylthio group having a straight chain or branched chain alkyl group having 1 to 6 carbon atoms or a cyclic alkyl group having 3 to 6 carbon atoms. For example, methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group, cyclobutylthio group and the like can be mentioned; and preferably, methylthio group, ethylthio group, n-propylthio group, isopropylthio group, cyclopropylthio group, cyclobutylthio group and the like can be mentioned.

The "heterocyclylthio group" is a group having a heterocyclic group (as defined above) on the sulfur atom. For example, 2-pyridylthio group, 3-pyridylthio group, 4-pyridylthio group, 2-pyrimidinylthio group, quinolylthio group, indolylthio group, 3-pyrrolidinylthio group, 4-piperidinylthio group, tetrahydropyranylthio group and the like can be mentioned; and preferably, 2-pyridylthio group, 3-pyridylthio group, 4-pyridylthio group, 3-pyrrolidinylthio group, 4-piperidinylthio group and the like can be mentioned.

The "arylthio group" is a group having an aryl group (as defined above) on the sulfur atom. For example, phenylthio group, 1-naphthylthio group, 2-naphthylthio group and the like can be mentioned; and preferably, phenylthio group and the like can be mentioned.

The "alkylamino group" is an amino group mono- or di-substituted by an alkyl group, where the alkyl group is exemplified by those shown for the aforementioned "alkyl group". For example, methylamino group, ethylamino group, propylamino group, isopropylamino group, dimethylamino group, diethylamino group, dipropylamino group, diisopropylamino group, methylethylamino group and the like can be mentioned; and preferably, methylamino group, ethylamino group, dimethylamino group, diethylamino group and the like can be mentioned.

The "alkylsulfonyl group" is an alkylsulfonyl group having a straight chain or branched chain alkyl group having 1 to 12 carbon atoms or a cyclic alkyl group having 3 to 12 carbon atoms. For example, methylsulfonyl group, ethylsulfonyl group, propylsulfonyl group, butylsulfonyl group, pentylsulfonyl group, hexylsulfonyl group, heptylsulfonyl group, octylsulfonyl group, nonylsulfonyl group, decylsulfonyl group, undecylsulfonyl group, dodecylsulfonyl group and the like can be mentioned; and preferably, methylsulfonyl group, ethylsulfonyl group and the like can be mentioned.

The "alkoxycarbonyl group" is an alkoxycarbonyl group having a straight chain or branched chain alkyl group having 1 to 6 carbon atoms or a cyclic alkyl group having 3 to 6 carbon atoms (=lower alkyl group; as defined above). For example, methoxycarbonyl group, ethoxycarbonyl group, propoxycarbonyl group, isopropoxycarbonyl group, n-butoxycarbonyl group, isobutoxycarbonyl group, sec-butoxycarbonyl group, tert-butoxycarbonyl group and the like can be mentioned; and preferably, methoxycarbonyl group, ethoxycarbonyl group, propoxycarbonyl group, isopropoxycarbonyl group and the like can be mentioned.

The "alkylcarbamoyl group" is a carbamoyl group optionally having one or two straight chain or branched chain alkyl groups having 1 to 6 carbon atoms or cyclic alkyl groups having 3 to 6 carbon atoms (=lower alkyl group; as defined above) on the nitrogen of the carbamoyl group. For example, N-methylcarbamoyl group, N-ethylcarbamoyl group, N,N-dimethylcarbamoyl group, N-pyrrolidylcarbonyl group, N-piperidylcarbonyl group, N-morpholinylcarbonyl group and the like can be mentioned; and preferably, N-methylcarbamoyl group, N,N-dimethylcarbamoyl group, N-ethylcarbamoyl group, N-pyrrolidylcarbonyl group, N-piperidylcarbonyl group and the like can be mentioned.

The "acyloxy group" is a formyloxy group, or an acyloxy group having a straight chain or branched chain alkyl group having 1 to 6 carbon atoms or a cyclic alkyl group having 3 to 6 carbon atoms (=lower alkyl group; as defined above), an acyloxy group having an alkenyl group having 2 to 6 carbon atoms, or an acyloxy group having an optionally substituted (as defined above) aryl group (as defined above). For example, formyloxy group, acetyloxy group, propionyloxy group, isopropionyloxy group, butyryloxy group, isobutyryloxy group, valeryloxy group, isovaleryloxy group, pivaloyloxy group, hexanoyloxy group, acryloyloxy group, methacryloyloxy group, crotonoyloxy group, isocrotonoyloxy group, benzoyloxy group, naphthoyloxy group and the like can be mentioned; and preferably, acetyloxy group, propionyloxy group, isopropionyloxy group, butyryloxy group, isobutyryloxy group, benzoyloxy group and the like can be mentioned.

The "alkylsulfonylamino group" is a sulfonylamino group substituted by a straight chain or branched chain alkyl group having 1 to 6 carbon atoms or a cyclic alkyl group having 3 to 6 carbon atoms (=lower alkyl group; as defined above). For example, methylsulfonylamino group, ethylsulfonylamino group, propylsulfonylamino group, isopropylsulfonylamino group, butylsulfonylamino group, isobutylsulfonylamino group and the like can be mentioned; and preferably, methylsulfonylamino group, ethylsulfonylamino group and the like can be mentioned.

The "arylsulfonylamino group" is a sulfonylamino group substituted by an aryl group (as defined above). For example, phenylsulfonylamino group, naphthylsulfonylamino group and the like can be mentioned; and preferably, phenylsulfonylamino group and the like can be mentioned.

The "hydroxyalkyl group" is a straight chain or branched chain alkyl group having 1 to 6 carbon atoms, which is substituted by hydroxy group(s). For example, hydroxymethyl group, 1-hydroxyethyl group, 2-hydroxyethyl group and the like can be mentioned; and preferably, hydroxymethyl group can be mentioned.

The "alkoxyalkyl group" is a straight chain or branched chain alkyl group having 1 to 6 carbon atoms, which is substituted by alkoxy group(s)(as defined above). For example, methoxymethyl group, 1-methoxyethyl group, 2-methoxyethyl group, ethoxymethyl group and the like can be mentioned; and preferably, methoxymethyl group can be mentioned.

In the present specification, the ring formed by R10 and R11 bonded to each other is a nitrogen-containing 5- or 6-membered ring formed with the adjacent nitrogen atom. Specifically, piperidine ring, pyrrolidine ring, piperazine ring, morpholine ring, thiomorpholine ring and the like can be mentioned. The ring may have substituent(s)(as defined above).

In the present specification, the ring formed by R20 and R21 bonded to each other is a nitrogen-containing 5- or 6-membered ring formed with the adjacent nitrogen atom, and specifically, piperidine ring, pyrrolidine ring, piperazine ring, morpholine ring, thiomorpholine ring and the like can be mentioned. The ring may have substituent(s)(as defined above).

In the present specification, the "3- to 6-membered ring, wherein said 3- to 6-membered ring optionally contains a heteroatom in the ring and optionally having substituent(s)" formed by $R_1a$ and $R_1a'$ bonded to each other is a 3- to 6-membered ring optionally containing, in the ring, 1 or 2 heteroatoms selected from the group consisting of oxygen atom, sulfur atom and nitrogen atom, which optionally has substituent(s)(as defined above). Specifically, tetrahydropyran ring, piperidine ring, tetrahydrothiopyran ring, cyclopropane ring, cyclobutane ring, cyclopentane ring, cyclohexane ring and the like can be mentioned.

In the present specification, the "5- or 6-membered ring, wherein said 5- or 6-membered ring optionally contains a heteroatom in the ring and optionally having substituent(s)" formed by $R_1a$ (or $R_1a'$) and R2 bonded to each other is a 5- or 6-membered ring optionally containing, in the ring, 1 or 2 heteroatoms selected from the group consisting of oxygen atom, sulfur atom and nitrogen atom, which optionally has substituent(s)(as defined above). Specifically, tetrahydropyran ring, piperidine ring, tetrahydrothiopyran ring, pyrrolidine ring, morpholine ring, thiomorpholine ring and the like can be mentioned.

In the present specification, the "3- to 6-membered ring, wherein said 3- to 6-membered ring optionally contains a heteroatom in the ring and optionally having substituent(s)" formed by $R_1c$ and $R_1c'$ bonded to each other is a 3- to 6-membered ring optionally containing, in the ring, 1 or 2 heteroatoms selected from the group consisting of oxygen atom, sulfur atom and nitrogen atom, which optionally has substituent(s)(as defined above). Specifically, tetrahydropyran ring, piperidine ring, tetrahydrothiopyran ring, cyclopropane ring, cyclobutane ring, cyclopentane ring, cyclohexane ring and the like can be mentioned.

In the present specification, the "5- or 6-membered ring, wherein said 5- or 6-membered ring optionally contains a heteroatom in the ring and optionally having substituent(s)" formed by $R_1c$ (or $R_1c'$) and R2 bonded to each other is a 5- or 6-membered ring optionally containing, in the ring, 1 or 2 heteroatoms selected from the group consisting of oxygen atom, sulfur atom and nitrogen atom, which optionally has substituent(s)(as defined above). Specifically, tetrahydropyran ring, piperidine ring, tetrahydrothiopyran ring, pyrrolidine ring, morpholine ring, thiomorpholine ring and the like can be mentioned.

The "nitrogen-containing 5- or 6-membered ring, wherein said 5- or 6-membered ring optionally further contains a heteroatom in the ring in addition to the nitrogen atom and optionally having substituent(s)" for ring a is a nitrogen-containing 5- or 6-membered ring optionally further containing a heteroatom (oxygen atom or sulfur atom) in addition to the nitrogen atom, which optionally has substituent(s)(as defined above). As the ring, piperidine, pyrrolidine, piperazine, morpholine, thiomorpholine and the like can be preferably mentioned.

The "nitrogen-containing 5- or 6-membered ring, wherein said nitrogen-containing 5- or 6-membered ring optionally further contains a heteroatom in the ring in addition to the nitrogen atom)" formed by R3 and B bonded to each other is a nitrogen-containing 5- or 6-membered ring optionally further containing a hetero atom (oxygen atom or sulfur atom) in addition to the nitrogen atom. As the ring, piperidine, pyrrolidine, piperazine, morpholine, thiomorpholine, 2-piperidinone, 3-piperidinone, 4-piperidinone, 2-pyrrolidinone, 3-pyrrolidinone and the like can be preferably mentioned.

In the formula (A), (B), (C) or (H), "X" is preferably a carbon atom.

In the formula (A), (B), (C) or (H), "M" is preferably a hydrogen atom, —$(CH_2)_m$ORa, —$(CH_2)_m$NRaRa', or —$(CH_2)_m$CO$_2$Ra. As Ra or Ra', a hydrogen atom and a lower alkyl group are preferable, and a hydrogen atom and a methyl group are particularly preferable. As "m", 0 and 1 are preferable.

In the formula (A) or (B), "Y" is preferably —C(O)— or —SO$_2$—, particularly preferably —C(O)—.

In the formula (A) or (B), "Z" is preferably a single bond, —CH(Rb)—, —CH(Rb)—CH(Rb')— or —CH═CH—, and particularly preferably, a single bond, —CH(Rb)— or —CH(Rb)—CH(Rb')—. As Rb or Rb', a hydrogen atom, an alkyl group (methyl group etc.) and -QR10 (preferably, Q is —O— or —NR11-) are preferable, and a lower alkyl group optionally having substituent(s) is also preferable. R10 and R11 are each preferably independently a hydrogen atom or a lower alkyl group. In addition, it is preferable that R10 and R11 be bonded to form a cyclopropane ring.

In the formula (C) or (H), "Z" is preferably a single bond, —CH(Rb)— or —CH(Rb)— CH(Rb')—, and particularly preferably —CH(Rb)— or —CH(Rb)—CH(Rb')—. As Rb or Rb', a hydrogen atom, —OR10 and —NR10R11 are preferable, and R10 and R11 are preferably each independently a hydrogen atom or a lower alkyl group.

In the formula (A), (B), (C) or (H), "B" is preferably a lower alkyl group optionally having substituent(s), or the formula (D):

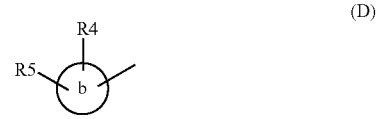

(D)

wherein each symbol is as defined above. As preferable examples of the "lower alkyl group optionally having substituent(s)", a methyl group, an ethyl group and a propyl group can be particularly mentioned, and as the "substituent(s)", a phenyl group, a hydroxyl group, an oxo group, an amino group, an alkylamino group and a heterocyclic group (piperidinyl group, pyridyl group, thienyl group, imidazolyl group, indolyl group, quinolyl group, benzothiazolyl group, piperidinyl group, tetrahydroquinolyl group, benzimidazolyl group, azabenzimidazolyl group, isoquinolyl group, etc.) are preferable.

For ring b, preferred are a heterocyclic group and an aryl group, as the heterocyclic group, a piperidinyl group, a pyridyl group, a thienyl group, an imidazolyl group, an indolyl group, a quinolyl group, a benzothiazolyl group, a piperidinyl group, a tetrahydroquinolyl group, a benzimidazolyl group, an azabenzimidazolyl group and an isoquinolyl group are particularly preferable, and as the aryl group, a phenyl group is preferable.

For R4 or R5 as the substituent of ring b, preferred are each independently a hydrogen atom, a halogeno group (fluorine atom, chlorine atom), an aryl group optionally having substituent(s), a heterocyclic group optionally having substituent(s), an alkyl group (particularly lower alkyl group) optionally having substituent(s) and -Q'R20 (wherein Q' is preferably —O—, —NR21 or —C(=O)NR21-, as R20 or R21, preferred are each independently a hydrogen atom, a lower alkyl group and a hydroxyl group); and a piperidinyl group, a phenyl group, a pyridyl group, a thienyl group, an imidazolyl group, an indolyl group, a quinolyl group, a benzothiazolyl group, a methyl group and an ethyl group are particularly preferable.

In the formula (A), (C) or (H), "R2" is preferably a hydrogen atom or a lower alkyl group optionally having substituent(s), and a hydrogen atom is particularly preferable.

In the formula (A), (B) or (C), "R3" is preferably a hydrogen atom.

In the formula (A) or (H), "$R_1a$" or "$R_1a'$" is preferably a hydrogen atom or a lower alkyl group, and a hydrogen atom, an isopropyl group, an isobutyl group, a sec-butyl group and a tert-butyl group are particularly preferable.

When one of $R_1a$ and $R_1a'$ is a hydrogen atom, a preferable configuration is shown by the following formula (A'):

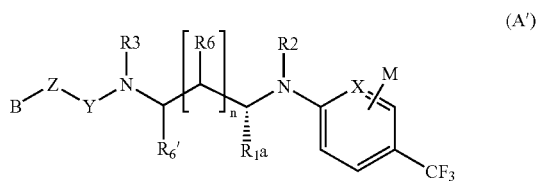

wherein each symbol is as defined above.

In the formula (A) or (H), "n" is 0 or 1, and 0 is particularly preferable.

In the formula (B), "$R_1b$" is preferably a hydrogen atom.

In the formula (C), "$R_1c$" or "$R_1c'$" is preferably a hydrogen atom or a lower alkyl group, and a hydrogen atom, an isopropyl group, an isobutyl group, a sec-butyl group and a tert-butyl group are particularly preferable. When $R_1c$ and $R_1c'$ forms a ring, cyclopentane, cyclohexane and tetrahydrothiopyran are preferable.

In the formula (C), "l" is preferably 0 or 1, and 1 is particularly preferable.

In the formula (C), when one of $R_1c$ and $R_1c'$ is a hydrogen atom, a preferable configuration is shown by the following formula (C'):

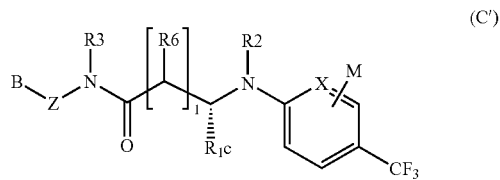

wherein each symbol is as defined above.

R12 and R13 in the formula (E) or the formula (E') preferably form a piperidine ring together with the adjacent nitrogen atom and carbon atom, and when they do not form a ring, R12 is preferably a hydrogen atom. L is preferably an alkyl group optionally having substituent(s) or a cycloalkyl group, and an alkyl group and a cycloalkyl group are preferable. Moreover, an n-propyl group, an n-butyl group, an isobutyl group, an n-pentyl group, a cyclopropylmethyl group and a cyclobutylmethyl group are particularly preferable.

The "kininogenase inhibitor" in the present invention refers to a pharmaceutical agent that substantially inhibits "kininogenase". Here, kininogenase includes tissue kallikrein and plasma kallikrein. As kininogenase, preferred is tissue kallikrein.

In addition, the "tissue kallikrein inhibitor" in the present invention refers to a pharmaceutical agent that substantially inhibits "tissue kallikrein". As the tissue kallikrein inhibitor, a compound showing a pIC50 of not less than 5 in the evaluation system in Experimental Example 1 of the present specification is preferable, and a compound showing a pIC50 of not less than 6 is particularly preferable. As the "tissue kallikrein inhibitor", for example, the following compounds are included in addition to the compounds described in the specification of the present invention.

The compounds of claim 1 of WO95/07291 (e.g., Examples 1 to 366, particularly, FE999024 of Example 161 etc.), the compounds of claim 1 of WO92/04371 (e.g., Examples 1 to 181), the compounds of claim 1 of WO2003/076458 (e.g., Examples 1 to 58), the compounds of claim 1 of JP08-59658A (e.g., Examples 1 to 7), the compounds of claim 1 of WO94/29335 (e.g., Examples 1 to 8), the compounds of claim 1 of WO94/29336 (e.g., Examples 1 to 90), the compounds of claim 1 of WO99/37611 (e.g., Examples 1 to 26), the compounds of claim 1 of WO98/06740, the compounds of claim 1 of WO0/09165, the compounds of claim 1 of U.S. Pat. No. 5,464,820, the compounds in *British Journal of Pharmacology*, 130, 1099-1107 (2000), the compounds in *Biological Chemistry*, 383, 853-857, (2002), Cetraxate, ONO-3307, Melagatran and the like can be mentioned.

When the compound of the present invention can form a salt, a pharmaceutically acceptable salt is preferable. As such pharmaceutically acceptable salt, when the compound has an acidic group such as a carboxyl group and the like, for example, ammonium salt; salts with alkali metals such as sodium, potassium and the like; salts with alkaline earth metals such as calcium, magnesium and the like; aluminum salt; zinc salt; salts with organic amines such as triethylamine, ethanolamine, morpholine, pyrrolidine, piperidine, piperazine, dicyclohexylamine and the like; and salts with basic amino acids such as arginine, lysine and the like can be mentioned.

When the compound has a basic group, salts with inorganic acids such as hydrochloric acid, sulfuric acid, phosphoric acid, nitric acid, hydrobromic acid and the like; salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, trifluoroacetic acid and the like; and salts with organic sulfonic acids such as methanesulfonic acid, benzenesulfonic acid, p-toluenesulfonic acid and the like can be mentioned.

As a method for forming a salt, mixing the compound of the present invention with a necessary acid or base at a suitable amount ratio in a solvent or dispersing agent, or cation exchange or anion exchange of a salt in other form is carried out.

The compound of the present invention includes solvates thereof, such as hydrates, alcohol addition products, and the like.

The compound of the present invention encompasses an optical isomer thereof, a stereoisomer thereof, a regioisomer thereof, a tautomer thereof, a rotational isomer thereof, and mixtures thereof at an optional ratio, when they are present. These can be each obtained as a single product by synthesis methods and separation methods known per se. For example, an optical isomer can be obtained by the use of an optically active synthetic intermediate, or by subjecting a racemate of the synthetic intermediate or the final product to optical resolution according to a conventional method.

The compound of the present invention can be converted to a prodrug. In the present invention, the term prodrug means a compound that is converted in the body to produce the compound of the present invention. For example, when the active compound contains a carboxyl group or a phosphoric acid group, an ester thereof, an amide thereof, and the like can be mentioned, and when the active compound contains a carboxyl group, a group that is converted to a carboxyl group by oxidative metabolism, such as hydroxymethyl group and the like can be mentioned. When the active compound contains an amino group, an amide thereof, a carbamate thereof, and the like can be mentioned. When the active compound contains a hydroxyl group, an ester thereof, a carbonate thereof, a carbamate thereof, and the like can be mentioned. When the compound of the present invention is converted to a prodrug, it may be bonded to amino acid or sugar.

Since the compound of the present invention and a pharmaceutically acceptable salt thereof (hereinafter to be simply referred to as the compound of the present invention) have a superior action to inhibit the physiological activity of kininogenase in mammals (e.g., bovine, horse, dog, mouse, rat etc.) including humans, it can be used as a pharmaceutical agent. The compound of the present invention or a salt thereof can be administered as it is, or as a pharmaceutical composition containing pharmaceutically acceptable carriers according to a method known per se, orally or parenterally (e.g., routes via intravenous, subcutaneous, intramuscular, suppository, intestinal infusion, ointment, plaster, sublingual, instillation, inhalation, etc.). While the dose for the above-mentioned object is determined depending on the objective treatment effect, administration method, treatment period, age, body weight, and the like, when an oral or parenteral route is employed, the daily dose for an adult is generally 1 µg to 10 g by oral administration, and 0.01 µg to 1 g by parenteral administration, which is administered once to several times per day. The content of the compound of the present invention in the above-mentioned pharmaceutical composition is about 0.01 wt % to 100 wt % of the whole composition.

As a pharmaceutically acceptable carrier for the pharmaceutical composition of the present invention, various organic or inorganic carrier substances conventionally used as materials for preparation can be mentioned. For example, excipients, lubricants, binders, disintegrants, water-soluble polymers, basic inorganic salts for solid preparations; and solvents, dissolution aids, suspending agents, isotonicity agents, buffers, soothing agents, and the like for liquid preparations can be mentioned. Where necessary, general additives, such as preservatives, antioxidants, coloring agents, sweetening agents, souring agents, bubbling agents, flavors, and the like can also be used.

As the dosage form of such pharmaceutical compositions, for example, tablets, powders, pills, granules, capsules, suppositories, liquids, sugar coatings, depots, syrups, suspensions, emulsions, troches, sublingual tablets, adhesive agents, intraorally disintegrants (tablets), inhalants, intestinal infusions, ointments, plasters, tapes, and eye drops can be mentioned, and a pharmaceutical composition can be produced using ordinary preparation auxiliaries and according to a conventional method.

The pharmaceutical composition of the present invention can be produced according to a method conventionally used in the technical field of preparations, such as a method described, for example, in the Japanese Pharmacopoeia and the like. Concrete production methods of the preparation are described in detail in the following.

For example, when the compound of the present invention is formed as an oral preparation, an excipient, and where necessary, a binder, disintegrant, lubricant, coloring agent, flavoring agent, and the like are added, and the mixture is processed according to a conventional method to give, for example, a tablet, powder, pill, granule, capsule, suppository, solution, sugar coating agent, depot, syrup, and the like. As the excipient, for example, lactose, cornstarch, sucrose, glucose, sorbit, crystalline cellulose, and the like can be used, as the binder, for example, polyvinyl alcohol, polyvinyl ether, ethylcellulose, methylcellulose, gum arabic, tragacanth, gelatin, shellac, hydroxypropylcellulose, hydroxypropyl starch, polyvinylpyrrolidone, and the like can be used, as the disintegrant, for example, starch, agar, gelatin powder, crystalline cellulose, calcium carbonate, sodium hydrogencarbonate, calcium citrate, dextran, pectin, and the like can be used, as the lubricant, for example, magnesium stearate, talc, polyethylene glycol, silica, hydrogenated vegetable oil, and the like can be used, as the coloring agent, those permitted to be added to pharmaceutical products can be used, and as the flavoring agent, cocoa powder, menthol, aromatic powder, mentha oil, borneo camphor, powdered cinnamon bark, and the like are used. It is naturally permissible to appropriately apply a sugar coating, gelatin coating, and other necessary coating to these tablets and granules.

When an injection is to be prepared, a pH adjusting agent, buffer, stabilizer, preservative, and the like are added where necessary, and the mixture is processed according to a conventional method to give a subcutaneous, intramuscular, or intravenous injection.

The compound of the present invention can be used appropriately along with one or more other pharmaceutical agents depending on the desired object. For example, when the compound of the present invention is used for inflammatory bowel disease (IBD), it can be used for the treatment in combination with a commercially available therapeutic drug for IBD (for example, anti-TNF preparation, steroid preparation, 5-aminosalicyl acid preparation etc.). When the compound of the present invention is used for the treatment of asthma, it can be used for the treatment in combination with a commercially available therapeutic drug for asthma (for example, bronictiodilator preparations such as β stimulant, theophylline and the like, antiallergic preparations such as leukotriene, thromboxane antagonist and the like, chemical mediator release inhibitor, steroid preparation etc.). When the compound of the present invention is used for the treatment of pancreatitis, it can be used for the treatment in combination with a commercially available therapeutic drug for pancreatitis (for example, protease inhibitor). When the compound of the present invention is used for cancer, it can be used for the treatment in combination with a therapeutic drug for cancer that is usable for the treatment. In the case of concurrent use, the dose thereof is appropriately determined according to the kind and efficacy of the pharmaceutical agent to be concurrently used, administration method, treatment period, age, body weight, and the like. The concurrent use is advantageous in that the doses of the two ingredients can be reduced, and the side effects caused thereby can also be reduced.

While the production methods of the compounds of the present invention are explained in the following, the production methods of the compounds of the present invention are not limited to those mentioned below. In addition, the functional group other than the moiety involved in the reaction may be protected in advance where necessary before carrying out the below-mentioned reactions and deprotected at a suitable stage. In each step, moreover, the reaction may be carried out according to the methods generally employed, and the isolation and purification can be performed by a method conventionally employed, such as crystallization, recrystallization, column chromatography, tin layer chromatography, high performance liquid chromatography (HPLC), and the like, which are selected as appropriate or used in combination.

The symbols used for the explanation of the production methods are shown in the following. Each symbol is as defined above unless otherwise specified.

Hal: halogen atom or pseudohalogen atom group (e.g., triflate etc.)
LG: leaving group
P: protecting group
alkyl: lower alkyl Synthesis method of compound represented by the formula (A)

For example, an aniline derivative (3, X=C) can be synthesized by an aromatic nucleophilic substitution reaction of amino acid derivative (1) and, for example, aromatic halide or aromatic pseudohalide (2) in a solvent that does not adversely influence this reaction (e.g., dimethylacetamide etc.) in the presence of a copper catalyst (e.g., copper iodide) by adding a base (e.g., potassium carbonate etc.)(*J. Am Chem. Soc.*, 120(48), 12459-12467 (1998)).

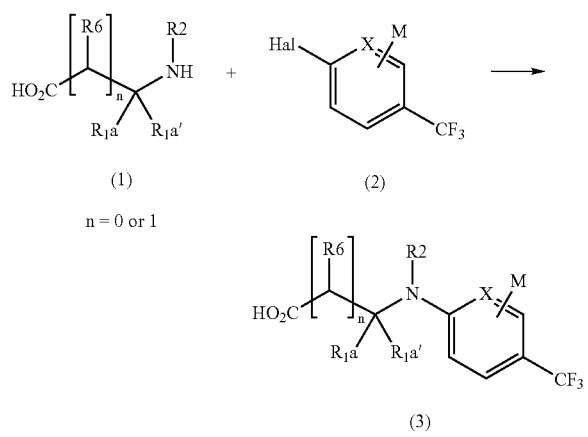

When X is a nitrogen atom, a 2-aminopyridine derivative (3, X=N) can be synthesized by stiring with heating at 50° C. to 120° C. in a solvent that does not adversely influence this reaction (e.g., ethanol etc.) using a base (e.g., triethylamine). The aniline derivative or 2-aminopyridine derivative (3) can be led to alcohol derivative (4) by reacting with, for example, ethyl chloroformate in a solvent that does not adversely influence this reaction (e.g., tetrahydrofuran etc.) in the presence of a base (e.g., triethylamine), and then reacting the resulting compound with a suitable reducing agent (e.g., sodium borohydride).

The alcohol derivative (4) can be led to compound (5) having a leaving group wherein LG in the schema is methanesulfonyloxy group or halogeno group, by reacting with, for example, methanesulfonyl chloride in a solvent that does not adversely influence this reaction (e.g., methylene chloride etc.) in the presence of a base (e.g., triethylamine).

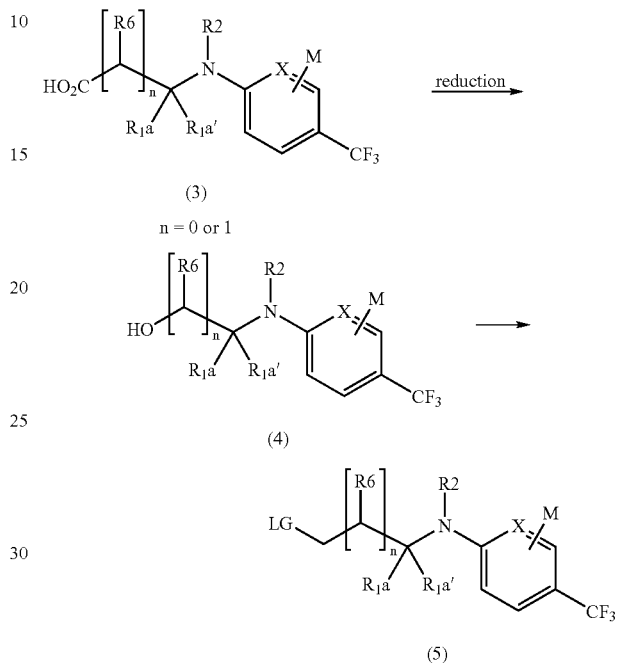

Compound (5) having a leaving group can be led to azide derivative (6) by reacting with, for example, sodium azide in a solvent that does not adversely influence this reaction (e.g., dimethylformamide etc.). The azide derivative (6) can be led to amine derivative (7) by treating with, for example, 10% palladium/carbon in a solvent that does not adversely influence this reaction (e.g., methanol etc.), for example, under a hydrogen atmosphere.

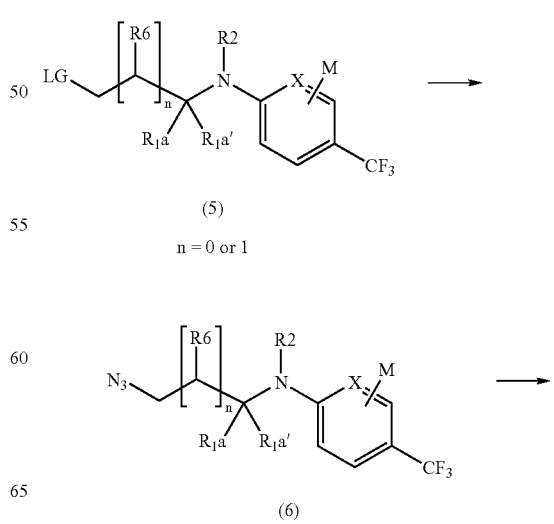

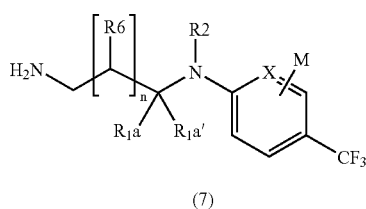

(7)

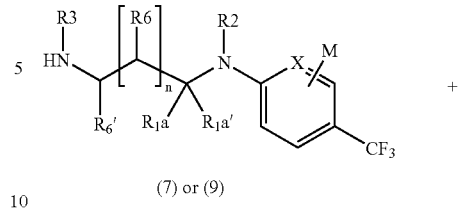

(7) or (9)

n = 0 or 1

When n=0, compound (5) can be led to cyano derivative (8) by reacting with, for example, sodium cyanide in, for example, dimethylformamide. The cyano derivative (8) can also be led to amine derivative (9) wherein n=1, by treating with, for example, 10% palladium/carbon, for example, in ethanol containing 0.5 N hydrogen chloride, for example, under a hydrogen atmosphere.

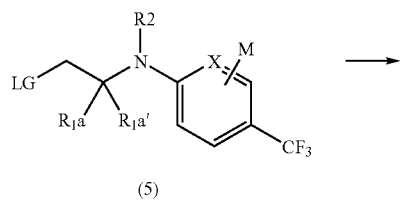

(5)

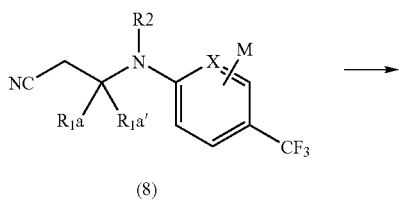

(8)

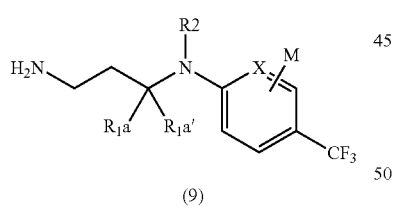

(9)

The object compound (A) can be obtained by reacting amine derivative (7) or (9) with, for example carboxylic acid derivative (10, Y is C=O) in a solvent that does not adversely influence this reaction (e.g., methylene chloride etc.) using a base (e.g., triethylamine), a condensing agent (e.g., 1-ethyl-(3-dimethylaminopropyl)carbodiimide hydrochloride) and an auxiliary condensing agent (e.g., 1-hydroxybenzotriazole). In addition, a sulfonyl derivative can also be synthesized by stirring amine derivative (7) or (9) and, for example, sulfonyl chloride derivative (10, Y is SO$_2$) instead of carboxylic acid derivative (10), in a solvent that does not adversely influence this reaction (e.g., methylene chloride etc.) in the presence of a base (e.g., triethylamine).

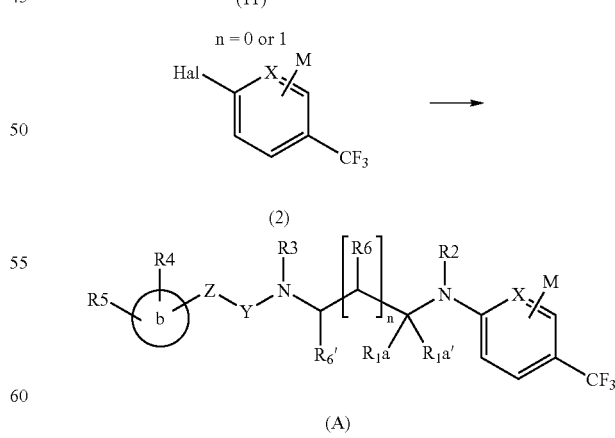

Compound (A) can also be obtained by subjecting previously amidated or sulfoneamidated compound (11) and aromatic halide or aromatic pseudohalide (2) to an aromatic nucleophilic substitution reaction.

When R12 and R13 in the formula (E) do not form a ring and L is represented by the formula (F), the compound corresponds to the formula (A) wherein M is a hydroxymethyl group. Such compound can be synthesized by the above-mentioned method.

Synthesis method of compound represented by the formula (B)

For example, aniline derivative (13) can be obtained by subjecting diamine derivative (12) and aromatic halide or aromatic pseudohalide (2) to an aromatic nucleophilic substitution reaction in a solvent that does not adversely influence this reaction (e.g., 2-propanol etc.) by adding a base (e.g., potassium phosphate), an additive (e.g., ethylene glycol) and a catalyst (e.g., copper iodide)(*Org. Lett.,* 4(4), 581-584, (2002)). When X is a nitrogen atom, for example, 2-aminopyridine derivative (13, X=N) can be synthesized by stirring with heating at 100° C. to 160° C. in dimethylformamide using a base (e.g., potassium carbonate).

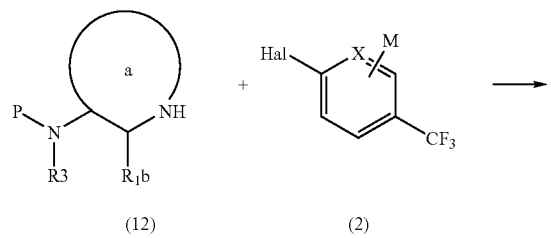

(12)　　(2)

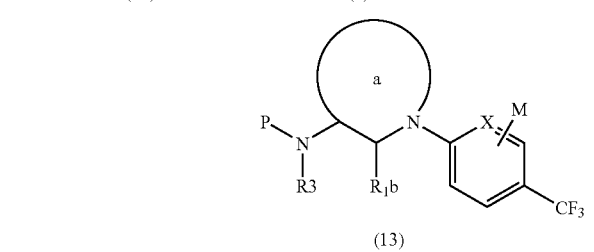

(13)

Amine derivative (14) can be obtained by reacting aniline derivative (13) wherein, for example, protecting group P is a tert-butoxycarbonyl group, with, for example, a dioxane solution containing 4 N hydrogen chloride to remove protecting group P.

The object compound (B) can be obtained from amine derivative (14) and carboxylic acid derivative (10, Y is C=O) in the same manner as above.

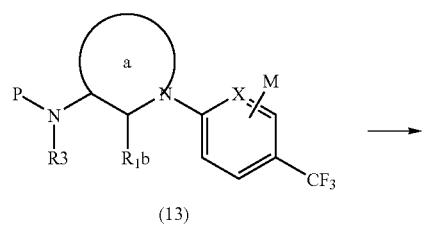

(13)

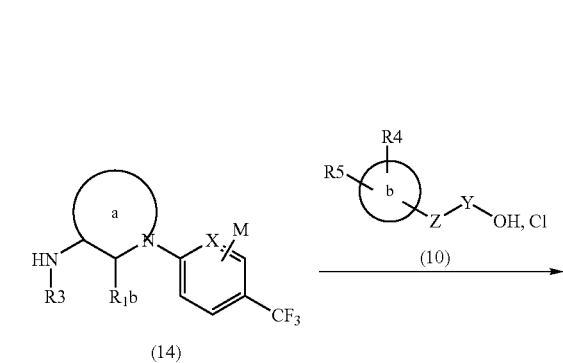

(14)

-continued

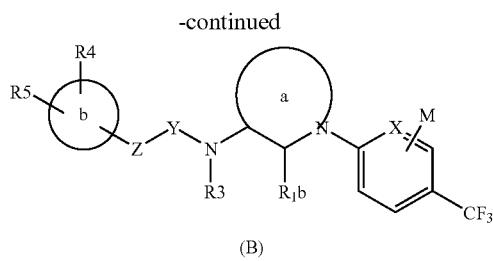

(B)

Compound (B) can also be obtained by subjecting a previously amidated or sulfoneamidated compound to an aromatic nucleophilic substitution reaction in the same manner as in compound (A).

Synthesis method of compound represented by the formula (C)

Cyano derivative (8) shown in the synthesis method of the formula (A) can also be led to carboxylic acid derivative (15) by stirring with heating at 80° C. to 120° C. in a solvent that does not adversely influence this reaction (e.g., 50% aqueous sulfuric acid solution etc.).

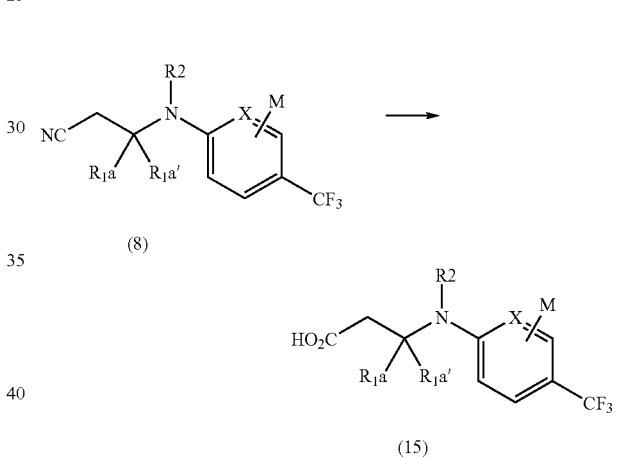

(8)

(15)

The object compound (C) can be obtained from carboxylic acid derivative (15) or compound (3) shown in the synthesis method of the formula (A), and, for example, amine acid derivative (16) in the same manner as above.

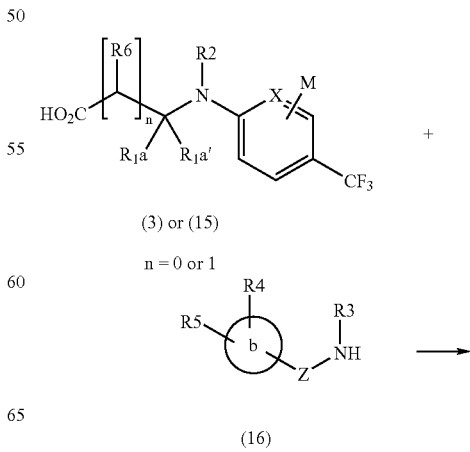

(3) or (15)

n = 0 or 1

(16)

-continued

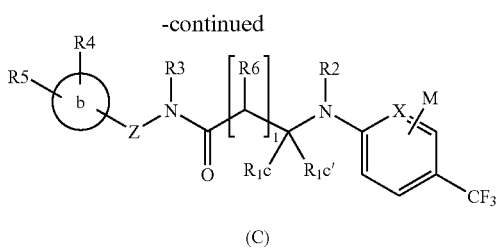

(C)

Compound (C) is obtained by subjecting a previously amidated or sulfoneamidated compound to an aromatic nucleophilic substitution reaction in the same manner as in compound (A).

When R12 and R13 in the formula (E) do not form a ring and L is represented by the formula (G), the compound corresponds to the formula (C) wherein M is a hydroxymethyl group. Such compound can be synthesized by the above-mentioned method.

Synthesis method of compound represented by the formula (E)

For example, halogenated aniline or pseudohalogenated aniline (17) can be led to compound (18) by stiring with heating at 50° C. to 100° C. under a carbon monoxide atmosphere in a solvent that does not adversely influence this reaction (e.g., methanol etc.) in the presence of a base (e.g., triethylamine) and a palladium catalyst (e.g., tetrakistriphenylphosphine palladium). Compound (18) can be led to compound (20) by reacting with suitable acid chloride (19) in a solvent that does not adversely influence this reaction (e.g., methylene chloride etc.) in the presence of a base (e.g., triethylamine).

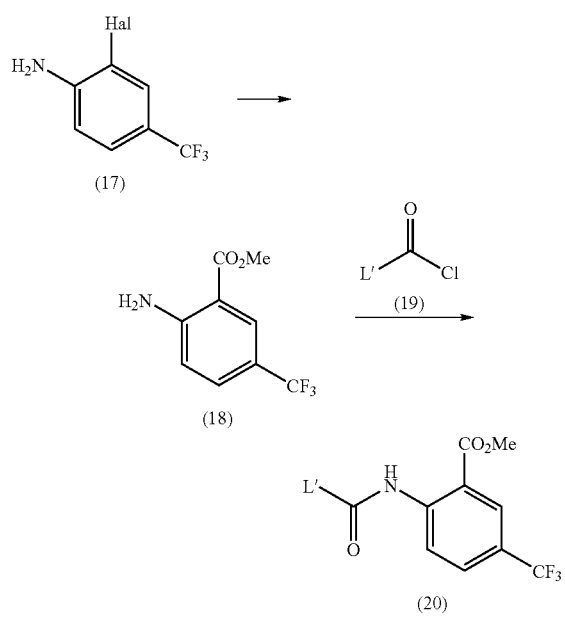

wherein L' is an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s) or an aralkyl group optionally having substituent(s).

Compound (E-1) wherein R12 and R13 in the formula (E) do not form a ring can be obtained by reacting compound (20) with a suitable reducing agent (e.g., lithium aluminum hydride) in a solvent that does not adversely influence this reaction (e.g., tetrahydrofuran etc.).

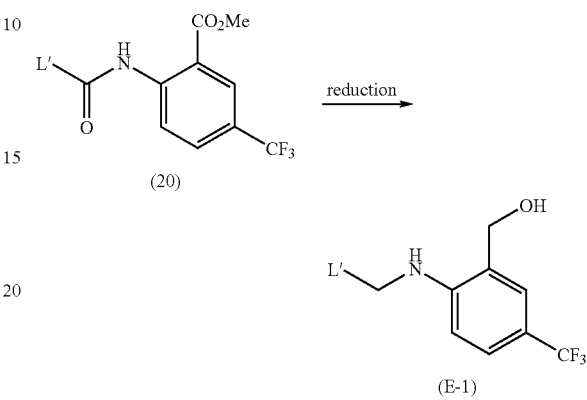

Amide compound (22) can be derived by stiring p-trifluoromethylaniline (21) and, for example, 3-bromopropanoic chloride in a solvent that does not adversely influence this reaction (e.g., methylene chloride etc.) in the presence of a base (e.g., N,N-dimethylaniline). Azetidinone derivative (23) can be synthesized by treating amide compound (22) with a base (e.g., potassium hydroxide) and a phase-transfer catalyst (e.g., tert-butylammonium bromide) in a solvent that does not adversely influence this reaction (e.g., appropriate mixed solvent of methylene chloride and acetonitrile, etc.)(*Chem. Pharm. Bull.,* 29(4), 1063-1068 (1981)). Dihydroquinolone derivative (24) can be synthesized by subjecting azetidinone derivative (23) to an intramolecular Friedel-Crafts reaction, for example, in 1,2-dichloroethane, for example, using trifluoromethanesulfonic acid (*Org. Lett.,* 4(3), 459-461 (2002)). Tetrahydroquinoline derivative (25) can be synthesized by reacting dihydroquinolone derivative (24) with a suitable reducing agent (e.g., sodium borohydride) in a solvent that does not adversely influence this reaction (e.g., ethanol etc.).

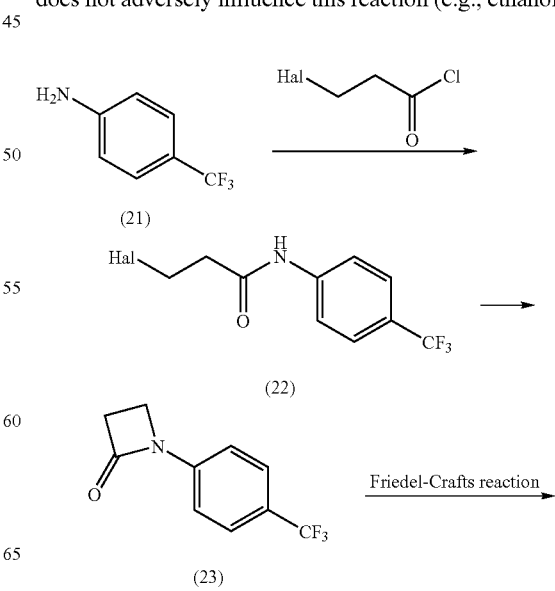

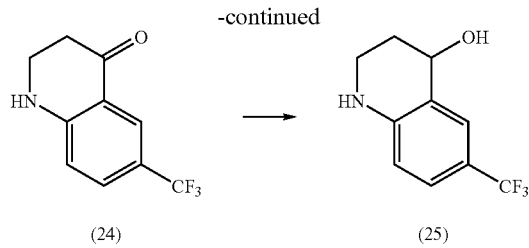

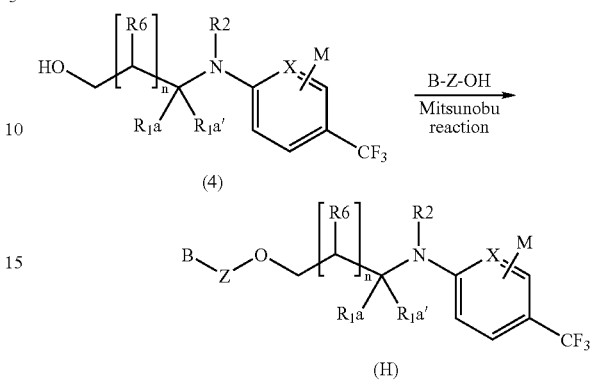

For example, compound (E-2) wherein R12 and R13 in the formula (E) form a ring in combination can be obtained by a reductive amination of tetrahydroquinoline derivative (25) and suitable aldehyde or ketone (26), (F') or (G') using a weak acid (e.g., acetic acid) and a suitable reducing agent (e.g., sodium triacetoxyborohydride), for example, in methylene chloride.

The above-mentioned alcohol derivative (4) can be led to compound (H) by treating with a base (e.g., sodium hydride), and stiring the reaction mixture and a compound having a suitable leaving group with heating at 20° C. to 100° C. in a solvent that does not adversely influence this reaction (e.g., dimethylformamide etc.).

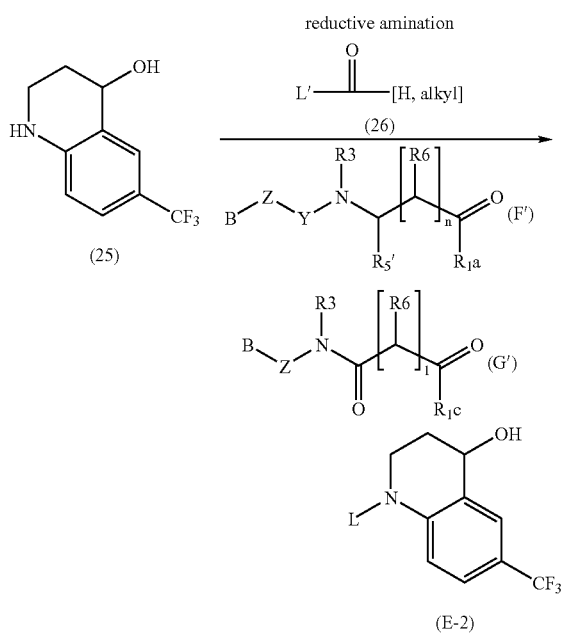

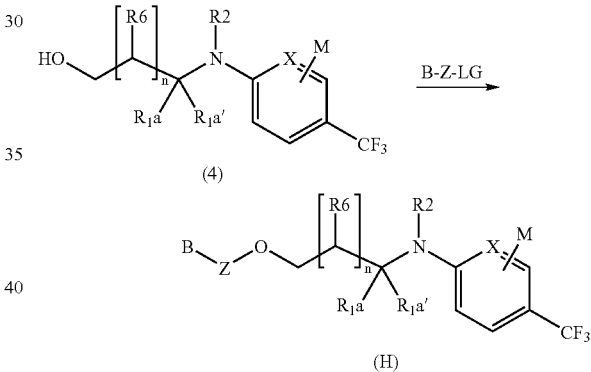

wherein L' is an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s) or an aralkyl group optionally having substituent(s).

A compound wherein the ring formed by R12 and R13 in the formula (E) in combination has substituent(s) can be synthesized according to patent reference (US2003/0055031) or non-patent reference (Dolores Edmont et al., Bioorg. Med. Chem. Lett., 10, 1831-1834 (2000)).

Synthesis method of compound represented by the formula (H)

Aryl ether compound (H) can be obtained by carrying out Mitsunobu reaction of the above-mentioned alcohol derivative (4) and a suitable aryl alcohol in a solvent that does not adversely influence this reaction (e.g., tetrahydrofuran etc.) in the presence of a phosphorus reagent (e.g., triphenylphosphine) and an azo reagent (e.g., diisopropyl azodicarboxylate).

EXAMPLES

The present invention is explained in more detail in the following by referring to Examples, which are not to be construed as limitative.

The structural formulas of the compounds indicated by compound numbers such as A-1, A-2 and the like in the Examples are described in the below-mentioned Tables.

In the present specification, a conventional method means methods generally used for organic syntheses, which are represented by partitioning operation, drying, filtration and concentration.

In the present specification, purification step A means a method comprising subjecting the obtained crude product to reversed-phase high performance liquid chromatography using silica gel chemically bonded with octadecyl group (ODS) as a filler, eluting with a mixed solution of water and acetonitrile, which contains 0.1% (v/v) trifluoroacetic acid, and lyophilizing the object fraction. The purification step B is a purification method of purification step A, which uses water and acetonitrile free of trifluoroacetic acid.

Example 1

Synthesis of $N^1$-(2-phenylethyl)-$N^2$-[4-(trifluoromethyl)phenyl]-D-valinamide trifluoroacetate (C-1)

Step 1

Synthesis of N-[4-(trifluoromethyl)phenyl]-D-valine

4-Trifluoromethyliodobenzene (0.27 g, 1.0 mmol), D-valine (0.12 g, 1.0 mmol), potassium carbonate (0.21 g, 1.5 mmol), copper(I) iodide (19 mg, 0.10 mmol) and dimethylacetamide (1 mL) were charged in a threaded test tube, and the mixture was stirred with heating at 90° C. for 2 days. After work-up according to a conventional method, the object product was eluted by silica gel column chromatography (20% to 40% mixed solvent of ethyl acetate/hexane) to give the title compound (0.12 g, 0.46 mmol, 46%).

$^1$H-NMR(300 MHz, CDCl$_3$) δ=1.06-1.10 (6H, m), 2.17-2.24 (1H, m), 3.94 (1H, d, J=5.4 Hz), 6.66 (2H, d, J=8.4 Hz), 7.24 (2H, d, J=8.4 Hz).

Step 2

Synthesis of $N^1$-(2-phenylethyl)-$N^2$-[4-(trifluoromethyl)phenyl]-D-valinamide trifluoroacetate N-[4-(Trifluoromethyl)phenyl]-D-valine (20 mg, 0.077 mmol) obtained in step 1, phenethylamine (11 μl, 0.087 mmol), 1-ethyl-(3-dimethylaminopropyl)carbodiimide hydrochloride (18 mg, 0.12 mmol) and 1-hydroxybenzotriazole monohydrate (22 mg, 0.12 mmol) were mixed in methylene chloride (3 mL), and the mixture was stirred overnight at room temperature. The solvent was evaporated and, using the following purification step A, the title compound (8.48 mg, 0.018 mmol, 23%) was obtained.

In the same manner as in Example 1 (C-1), compounds C-2 to C-39 were synthesized using the corresponding amino acid etc. instead of D-valine in Step 1 and the corresponding amine instead of phenethylamine in step 2.

Example 2

Synthesis of N-((2R)-3-methyl-2-{[4-(trifluoromethyl)phenyl]amino}butyl)-2-phenylacetamide trifluoroacetate (A-1)

Step 1

Synthesis of (2R)-3-methyl-2-{[4-(trifluoromethyl)phenyl]amino}butan-1-ol

N-[4-(Trifluoromethyl)phenyl]-D-valine (2.15 g, 8.23 mmol) obtained in Step 1 of Example 1 was dissolved in tetrahydrofuran (50 ml), and triethylamine (1.71 mL, 12.3 mmol) and ethyl chloroformate (0.94 mL, 9.88 mmol) were added under cooling. The precipitated salt was filtered off, sodium borohydride (0.62 g, 16.4 mmol) and ice were added, and the mixture was stirred overnight at room temperature. The solvent was evaporated and, after work-up according to a conventional method, the residue was purified by silica gel column chromatography (30% mixed solvent of ethyl acetate/hexane) to give the title compound (0.95 g, 3.84 mmol, 47%).

Step 2

Synthesis of (2R)-3-methyl-N2-[4-(trifluoromethyl)phenyl]butane-1,2-diamine (2R)-3-Methyl-2-{[4-(trifluoromethyl)phenyl]amino}butan-1-ol (1.67 g, 6.76 mmol) obtained in Step 1 was dissolved in methylene chloride (30 mL) and triethylamine (1.20 mL, 8.67 mmol), and methanesulfonyl chloride (0.63 mL, 8.14 mmol) was added dropwise under cooling. After stiring overnight, the mixture was worked-up according to a conventional method to give N-[(1R)-1-(chloromethyl)-2-methylpropyl]-4-(trifluoromethyl)aniline as a crude product. The obtained crude product was dissolved in dimethylformamide (20 mL), sodium azide (0.40 g, 6.15 mmol) was added, and the mixture was stirred overnight at 80° C. The solvent was evaporated, and the residue was worked-up according to a conventional method to give a crude product. The obtained crude product was dissolved in ethyl acetate (20 ml), 10% palladium/carbon (catalytic amount) was added, and the system was purged with hydrogen. The mixture was stirred overnight at room temperature, palladium/carbon was filtered off, and the solvent was evaporated to give the title compound (1.50 g, 6.09 mmol, 90%).

$^1$H-NMR(300 MHz, CDCl$_3$) δ=0.92-1.00 (6H, m), 1.85-1.94 (1H, m), 2.74 (1H, dd, J=7.2, 12.9 Hz), 2.88 (1H, m), 2.94 (1H, dd, J=12.9, 6.3 Hz), 3.20-3.28 (1H, m), 3.98-4.08 (1H, m), 6.63 (2H, d, J=8.4 Hz), 7.37 (2H, d, J=8.4 Hz).

MS (ESI) m/z 247 (M+H)$^+$

Step 3

Synthesis of N-((2R)-3-methyl-2-{[4-(trifluoromethyl)phenyl]amino}butyl)-2-phenylacetamide trifluoroacetate (2R)-3-Methyl-$N^2$-[4-(trifluoromethyl)phenyl]butane-1,2-diamine (8 mg, 0.033 mmol) obtained in step 2, phenylacetic acid (5 mg, 0.037 mmol), 1-ethyl-(3-dimethylaminopropyl)carbodiimide hydrochloride (10 mg, 0.052 mmol), 1-hydroxybenzotriazole monohydrate (8 mg, 0.052 mmol) and triethylamine (9 μl, 0.066 mmol) were mixed in methylene chloride (3 mL), and the mixture was stirred overnight at room temperature. The solvent was evaporated and the residue was purified by purification step A to give the title compound (4.1 mg, 0.009 mmol, 26%).

In the same manner as in Example 2 (A-1), compounds A-2 to A-46 were synthesized using the corresponding amine instead of (2R)-3-methyl-$N^2$-[4-(trifluoromethyl)phenyl]butane-1,2-diamine used in Step 3 of Example 2 and the corresponding carboxylic acid instead of phenylacetic acid.

Example 3

Synthesis of (3S)-N-benzyl-4-methyl-3-{[4-(trifluoromethyl)phenyl]amino}pentanamide (C-40)

Step 1

Synthesis of N-[(1R)-1-(cyanomethyl)-2-methylpropyl]-4-(trifluoromethyl)aniline

N-[(1R)-1-(Chloromethyl)-2-methylpropyl]-4-(trifluoromethyl)aniline (1.0 g, 3.76 mmol) obtained as an intermediate for Step 2 of Example 2 was dissolved in dimethylformamide (30 mL), sodium cyanide (0.22 g, 4.51 mmol) was added, and the mixture was stirred overnight at 90° C. The solvent was evaporated and, after work-up according to a conventional method, the mixture was purified by silica gel column chromatography (20% to 40% mixed solvent of ethyl acetate/hexane) to give the title compound (0.57 g, 2.22 mmol, 59%).

Step 2

Synthesis of (3S)-N-benzyl-4-methyl-3-{[4-(trifluoromethyl)phenyl]amino}pentanamide N-[(1R)-1-(Cyanomethyl)-2-methylpropyl]-4-(trifluoromethyl)aniline (0.1 g, 0.39 mmol) obtained in Step 1 was dissolved in 50% aqueous sulfuric acid solution, and the mixture was stirred overnight at 100° C. The reaction mixture was poured on ice, and adjusted to pH 3 to 5, and the mixture was extracted with ethyl acetate. Work-up according to a conventional method gave a crude product. 32 mg of the obtained crude product, benzylamine (20μ, 0.18 mmol), 1-ethyl-(3-dimethylaminopropyl)carbodiimide hydrochloride (20 mg, 0.10 mmol) and 1-hydroxybenzotriazole monohydrate (20 mg, 0.13 mmol) were mixed in methylene chloride (3 ml), and the mixture was stirred overnight at room temperature. The solvent was evaporated, and the title compound (3.45 mg, 0.007 mmol) was obtained by purification step A.

In the same manner as in synthesis Example 3 (C-40), compounds C-41 to C-43 were synthesized using the corresponding amine instead of benzylamine in Step 2 of Example 3.

Example 4

Synthesis of N-((3S))-4-methyl-3-{[4-(trifluoromethyl)phenyl]amino}pentyl)benzamide trifluoroacetate (A-47)

N-[(1R)-1-(Cyanomethyl)-2-methylpropyl]-4-(trifluoromethyl)aniline (0.2 g, 0.78 mmol) obtained in Step 1 of Example 3 was dissolved in ethanol solution (10 mL) containing 0.5 N hydrogen chloride, 10% palladium/carbon (catalytic amount) was added, the system was purged with hydrogen, and the mixture was stirred overnight. Palladium/carbon was filtered off, and the solvent was evaporated to give a crude product. 10 mg (0.032 mmol) of the obtained crude product, benzoic acid (8 mg, 0.064 mmol), 1-ethyl-(3-dimethylaminopropyl)carbodiimide hydrochloride (12 mg, 0.064 mmol), 1-hydroxybenzotriazole monohydrate (10 mg, 0.064 mmol) and triethylamine (0.02 mL, 0.14 mmol) were mixed in methylene chloride (2 mL), and the mixture was stirred overnight at room temperature. The solvent was evaporated and, after work-up according to a conventional method, and the title compound (4.18 mg, 0.009 mmol, 27%) was obtained by purification step A.

In the same manner as in Example 4 (A-47), compounds A-48 to A-54 were synthesized using the corresponding carboxylic acid instead of benzoic acid in Example 4.

Example 5

Synthesis of 2-phenyl-N-{(3R)-1-[4-(trifluoromethyl)phenyl]pyrrolidin-3-yl}acetamide trifluoroacetate (B-1)

Step 1

Synthesis of tert-butyl {(3R)-1-[4-(trifluoromethyl)phenyl]pyrrolidin-3-yl}carbamate 4-(Trifluoromethyl)iodobenzene (145 µl, 1.0 mmol), tert-butyl (3R)-pyrrolidin-3-ylcarbamate (0.22 g, 1.2 mmol), potassium phosphate (0.43 g, 2.0 mmol), ethylene glycol (0.11 mL, 2.0 mmol), copper(I) iodide (19 mg, 0.10 mmol) and 2-propanol (1 mL) were charged in a threaded test tube, and the mixture was stirred overnight at 80° C. The solvent was evaporated, and the residue was worked-up according to a conventional method. The obtained crude product was purified by silica gel column chromatography (15% mixed solvent of ethyl acetate/hexane) to give the title compound (0.07 g, 0.21 mmol, 21%).

Step 2

Synthesis of 2-phenyl-N-{(3R)-1-[4-(trifluoromethyl)phenyl]pyrrolidin-3-yl}acetamide trifluoroacetate tert-Butyl {(3R)-1-[4-(trifluoromethyl)phenyl]pyrrolidin-3-yl}carbamate (0.07 g, 0.2 1 mmol) obtained in Step 1 was dissolved in dioxane solution containing 4 N hydrogen chloride, the mixture was stirred at room temperature for 2 hours (hours=hrs.), and the solvent was evaporated. About 10 mg of the obtained crude product, phenylacetic acid (4.0 mg, 0.030 mmol), 1-hydroxy-7-azabenzotriazole (7.0 mg), triethylamine (20 µl) and diisopropylcarbodiimide (10 µl) were dissolved in dimethylformamide (1 mL), and the mixture was stirred overnight. The solvent was evaporated, and the title compound (10.1 mg) was obtained by purification step A.

In the same manner as in Example 5 (B-1), compounds B-2 to B-7 were synthesized using the corresponding carboxylic acid instead of phenylacetic acid in Step 2 of Example 5.

Example 6

Synthesis of (2E)-3-(pyridin-2-yl)-N-{1-[5-(trifluoromethyl)pyridin-2-yl]pyrrolidin-3-yl}acrylamide ditrifluoroacetate (B-8)

2-Chloro-5-trifluoromethylpyridine (18 mg, 1.0 mmol), tert-butyl (3R)-pyrrolidin-3-ylcarbamate (0.22 g, 1.2 mmol), triethylamine (1 mL) and ethanol (3 mL) were charged in a threaded test tube, and the mixture was stirred overnight at 130° C. The solvent was evaporated, and the residue was worked-up according to a conventional method to give a crude product (0.32 g). The obtained crude product (0.32 g) of tert-butyl {(3R)-1-[5-(trifluoromethyl)pyridin-2-yl]pyrrolidin-3-yl}carbamate was dissolved in a dioxane solution (3 mL) containing 4 N hydrogen chloride, and the mixture was stirred at room temperature for 2 hrs. The solvent was evaporated, 15 mg of the obtained crude product, 3-(2-pyridyl) acrylic acid (7.3 mg, 0.049 mmol), diisopropylcarbodiimide (10 µl, 0.059 mmol), 1-hydroxy-7-azabenzotriazole (8.0 mg, 0.059 mmol) and triethylamine (20 µl, 0.148 mmol) were mixed in dimethylformamide (1 mL), and the mixture was stirred overnight at room temperature. The solvent was evaporated, and the title compound (6.69 mg, 0.014 mmol) was obtained by purification step A.

Example 7

Synthesis of N-((2R)-2-{[2-(hydroxymethyl)-4-(trifluoromethyl)phenyl]amino}-3-methylbutyl)-2-phenylacetamide (A-55)

Step 1

Synthesis of [2-iodo-5-(trifluoromethyl)phenyl]methanol

2-Iodo-4-(trifluoromethyl)aniline (8.0 g, 27.9 mmol), methanol (5 mL) and triethylamine (10 mL) were dissolved in dimethylformamide (50 ml) and, under a carbon monoxide atmosphere, tetrakis(triphenylphosphine)palladium (1.6 g, 1.4 mmol) was added and the mixture was stirred at 50° C. for 5 days. The solvent was evaporated and work-up according to a conventional method gave a crude product of methyl 2-amino-5-(trifluoromethyl)benzoate. The obtained crude product was dissolved in tetrahydrofuran (20 ml), lithium aluminum hydride (1.0 g, 26.3 mmol) was added under cooling, and the mixture was stirred for 2 hrs. Water (1 ml), 30% aqueous sodium hydroxide solution (1 ml) and water (3 mL) were sequentially added, the precipitate was filtered off, and the filtrate was concentrated to give a crude product of [2-amino-5-(trifluoromethyl)phenyl]methanol. Sodium nitrite (59 mg, 0.86 mmol) was dissolved in conc. sulfuric acid (0.77 mL) and, after cooling, a solution of a crude product (0.15 g, 0.78 mmol) of [2-amino-5-(trifluoromethyl)phenyl]methanol in acetic acid (1.72 ml). After stiring for 30 min. 10% aqueous potassium iodide solution (4.64 mL) was added. After stirring with heating at 70° C. for 30 min, the mixture was worked-up according to a conventional method, and the obtained crude product was purified by silica gel column chromatography (5% to 7.5% ethyl acetate/hexane) to give the title compound (96 mg, 0.32 mmol, 40%).

Step 2

Synthesis of tert-butyl ((1R)-2-methyl-1-{[(phenylacetyl)amino]methyl}propyl)carbamate tert-Butyl [(1R)-1-(hydroxymethyl)-2-methylpropyl]carbamate (4.1 g, 20.2 mmol) was dissolved in methylene chloride (30 ml), triethylamine (3.6 m mL, 26.2 mmol) and methanesulfonyl chloride (1.7 mL, 22.2 mmol) were added, and the mixture was stirred overnight at room temperature. The solvent was evaporated, and the residue was worked-up according to a conventional method to give a crude product. 1.5 g (5.33 mmol) of the obtained crude product and sodium azide (0.42 g, 6.46 mmol) were dissolved in dimethylformamide (20 mL), and the mixture was stirred overnight at 80° C. The solvent was evaporated and work-up according to a conventional method gave a crude product. 0.44 g of the obtained crude product was dissolved in methanol, 10% palladium/carbon (catalytic amount) was added, and the system was purged with hydrogen, which was followed by stiring overnight. After filtering off palladium/carbon, the solvent was evaporated to give a crude product. The obtained crude product (0.20 g), phenylacetic acid (0.14 g, 0.99 mmol), 1-ethyl-(3-dimethylaminopropyl)carbodiimide hydrochloride (0.23 g, 1.19 mmol), 1-hydroxybenzotriazole monohydrate (0.18 g, 1.19 mmol) and triethylamine (0.21 mL, 1.48 mmol) were mixed in methylene chloride (3 mL), and the mixture was stirred overnight at room temperature. The solvent was evaporated and, after work-up according to a conventional method, the residue was purified by silica gel column chromatography (35% to 45% mixed solvent of ethyl acetate/hexane) to give the title compound (0.26 g, 0.80 mmol, 81%).

Step 3

Synthesis of N-((2R)-2-{[2-(hydroxymethyl)-4-(trifluoromethyl)phenyl]amino}-3-methylbutyl)-2-phenylacetamide tert-Butyl ((1R)-2-methyl-1-{[(phenylacetyl)amino]methyl}propyl)carbamate (0.24 g, 0.75 mmol) obtained in Step 2 was dissolved in a dioxane solution (3 ml) containing 4 N hydrogen chloride, and the mixture was stirred at room temperature for 2 hrs. The solvent was evaporated, and 1 N aqueous sodium hydroxide solution and methylene chloride were added. The mixture was worked-up according to a conventional method to give a crude product (0.24 g) of N-[(2R)-2-amino-3-methylbutyl]-2-phenylacetamide. The obtained crude product (40 mg, 0.18 mmol), [2-iodo-5-(trifluoromethyl)phenyl]methanol (45 mg, 0.15 mmol) obtained in step 1, potassium phosphate (63 mg, 0.30 mmol) and ethylene glycol (17 μl, 0.30 mmol) were dissolved in 2-propanol (1 mL), and the mixture was stirred with heating overnight at 80° C. The solvent was evaporated and, after work-up according to a conventional method, the title compound (10.6 mg, 0.027 mmol, 18%) was obtained by purification step B.

Example 8

Synthesis of N-((2R)-2-{[2-amino-4-(trifluoromethyl)phenyl]amino}-3-methylbutyl)-2-phenylacetamide trifluoroacetate (A-56)

In the same manner as in Step 2 of Example 1, a crude product of tert-butyl ((1R)-2-methyl-1-{[(phenylacetyl)amino]methyl}propyl)carbamate was obtained from a crude product (50 mg, 0.25 mmol) of tert-butyl [(1R)-1-(aminomethyl)-2-methylpropyl]carbamate obtained in Step 2 of Example 7 and phenylacetic acid. The obtained crude product was dissolved in a dioxane solution (5 mL) containing 4 N hydrogen chloride, and the mixture was stirred at room temperature for 1 hr. The solvent was evaporated, the obtained crude product, 1-chloro-2-nitro-4-(trifluoromethyl)benzene (30 μl, 0.20 mmol) and potassium carbonate (57 mg, 0.41 mmol) were dissolved in a mixed solvent (2.2 ml) of dimethylformamide and water, and the mixture was stirred overnight at 40° C. The solvent was evaporated and work-up according to a conventional method gave a crude product of N-((2R)-3-methyl-2-{[2-nitro-4-(trifluoromethyl)phenyl]amino}butyl)-2-phenylacetamide. The obtained crude product was dissolved in methanol (5 ml), 10% palladium/carbon (catalytic amount) was added, and the system was purged with hydrogen. After stirring overnight at room temperature, the catalyst was filtered off. The solvent was evaporated, and the title compound (10.1 mg, 0.020 mmol, 8%) was obtained by purification step A.

Compounds A-57 to A-61 were synthesized in the same manner as in Example 8 (A-56) except that the corresponding carboxylic acid was used instead of phenylacetic acid in Example 8.

Example 9

Synthesis of {2-(cyclopropylmethyl)amino-5-trifluoromethyl}phenylmethanol (E-1)

Step 1

Synthesis of methyl {2-(cyclopropylcarbonyl)amino-5-trifluoromethyl}benzoate

Methyl 2-amino-5-(trifluoromethyl)benzoate (0.20 g, 0.91 mmol) obtained as an intermediate for Step 1 of Example 7 was dissolved in methylene chloride (10 ml), triethylamine (0.25 mL, 1.82 mmol) and cyclopropanecarbonyl chloride (0.11 g, 1.1 mmol) were added at 0° C., and the mixture was stirred overnight at room temperature. After work-up according to a conventional method, the mixture was purified by silica gel column chromatography (10% to 30% mixed solvent of ethyl acetate/hexane) to give the title compound (0.10 g, 0.35 mmol).

Step 2

Synthesis of {2-(cyclopropylmethyl)amino-5-trifluoromethyl}phenylmethanol

Methyl {2-(cyclopropylcarbonyl)amino-5-trifluoromethyl}benzoate (0.10 g, 0.35 mmol) obtained in Step 1 was dissolved in THF (5 ml), lithium aluminum hydride (66 mg, 1.74 mmol) was added at 0° C., and the mixture was stirred overnight at room temperature. Water (0.066 mL), 30% aqueous sodium hydroxide solution (0.066 mL) and water (0.20 mL) were sequentially added, and the precipitate was filtered off. The filtrate was concentrated and the residue was purified by silica gel column chromatography (35% to 45% mixed solvent of ethyl acetate/hexane) to give the title compound (7.4 mg, 0.030 mmol, 9%).

Compound E-2 was synthesized in the same manner as in Example 9 (E-1) except that the corresponding acid chloride was used instead of cyclopropanecarbonyl chloride in Step 1 of Example 9.

Example 10

Synthesis of 1-propyl-6-(trifluoromethyl)-1,2,3,4-tetrahydroquinolin-4-ol (E-3)

Step 1

Synthesis of 1-[4-(trifluoromethyl)phenyl]azetidin-2-one

3-Bromopropanoyl chloride (3.13 mL, 31.0 mmol) and N,N-dimethylaniline (3.91 mL, 31.0 mmol) were dissolved in methylene chloride (30 ml), 4-trifluoromethylaniline (5 g, 31.0 mmol) was added dropwise at 0° C., and the mixture was stirred at room temperature for 2 hrs. Work-up of the reaction mixture according to a conventional method gave a crude product. The obtained crude product was dissolved in a mixed solvent (100 mL) of methylene chloride/acetonitrile (20/1), potassium hydroxide (2.28 g, 40.6 mmol) and tetrabutylammonium bromide (3.26 g, 6.76 mmol) were added, and the mixture was stirred overnight at room temperature. The solvent was evaporated and, after work-up according to a conventional method, the mixture was purified by silica gel column chromatography to give the title compound (4.6 g, 21.4 mmol, 71%).

Step 2

Synthesis of 6-(trifluoromethyl)-1,2,3,4-tetrahydroquinolin-4-ol

1-[4-(Trifluoromethyl)phenyl]azetidin-2-one (2.3 g, 10.7 mmol) was dissolved in 1,2-dichloroethane (20 mL), trifluoromethanesulfonic acid (1 mL) was added at 0° C., and the mixture was stirred at room temperature for 30 min. Triethylamine (2.2 mL) was added to the reaction mixture, and the mixture was worked-up according to a conventional method to give a crude product. The obtained crude product was dissolved in ethanol (10 mL), sodium borohydride (0.81 g, 21.4 mmol) was added, and the mixture was stirred for 4 hrs. The solvent was evaporated and the residue was purified by silica gel column chromatography to give the title compound (0.35 g, 1.6 mmol, 15%).

Step 3

Synthesis of 1-propyl-6-(trifluoromethyl)-1,2,3,4-tetrahydroquinolin-4-ol 6-(Trifluoromethyl)-1,2,3,4-tetrahydroquinolin-4-ol (30 mg, 0.14 mmol) obtained in Step 2 was dissolved in methylene chloride (2 ml), propylaldehyde (16 mg, 0.28 mmol), acetic acid (20 µl) and sodium triacetoxyborohydride (59 mg, 0.28 mmol) were added, and the mixture was stirred overnight. The solvent was evaporated, and the residue was subjected to reversed-phase high performance liquid chromatography using ODS as a filler, and eluted with a mixed solution of water and acetonitrile, which contains 0.1% (v/v) trifluoroacetic acid. Aqueous sodium hydrogencarbonate solution was added to the object fraction. Acetonitrile was evaporated under reduced pressure and the remaining aqueous layer was partitioned with ethyl acetate. The solvent was evaporated to dryness to give the title compound (10.4 mg, 0.04 mmol, 29%).

Compounds E-4 to E-6 were synthesized in the same manner as in Example 10 (E-3) except that the corresponding aldehyde was used instead of propylaldehyde in Step 3 of Example 10.

Example 11

Synthesis of N-[(1R)-2-methyl-1-(phenoxymethyl)propyl]-4-(trifluoromethyl)aniline (H-1)

(2R)-3-Methyl-2-{[4-(trifluoromethyl)phenyl]amino}butan-1-ol (50 mg, 0.201 mmol), which is the compound obtained in Step 1 of Example 2, phenol (19 mg) and triphenylphosphine (63 mg) were dissolved in tetrahydrofuran (1 mL), and after cooling to 0° C., diisopropyl azodicarboxylate (0.13 mL) was added dropwise. The mixture was stirred overnight at 50° C. and purified by purification step A to give the title compound (2.18 mg).

Compound H-2 was synthesized in the same manner as in Example 11 (H-1) except that the corresponding alcohol was used instead of phenol in Example 11 (H-1).

Example 12

Synthesis of N-{(1R)-1-[(benzyloxy)methyl]-2-methylpropyl}-4-(trifluoromethyl)aniline (H-3)

Sodium hydride (10 mg) and (2R)-3-methyl-2-{[4-(trifluoromethyl)phenyl]amino}butan-1-ol (30 mg), which is the compound obtained in Step 1 of Example 2, were dissolved in dimethylformamide (1 mL), and then benzyl bromide (0.052 mL) was added. The mixture was stirred at 50° C. for 3 hrs, and the title compound (37.5 mg) was obtained by purification step A.

Compounds H-4 and H-5 were synthesized in the same manner as in Example 12 (H-3) except that the corresponding halide was used instead of benzyl bromide in Example 12 (H-3).

Example 13

Synthesis of N-{(1R)-2-methyl-1-[(2-phenylethoxy)methyl]propyl}-4-(trifluoromethyl)aniline (H-6)

(2R)-3-Methyl-2-{[4-(trifluoromethyl)phenyl]amino}butan-1-ol (50 mg, 0.201 mmol), which is the compound obtained in Step 1 of Example 2, phenethylbromide (0.22 mL, 2.01 mmol) and tetrabutylammonium hydrogensulfate (catalytic amount) were added to a mixed solvent of benzene(1 mL) and 50% aqueous sodium hydroxide solution (1 mL), and the mixture was stirred at 50° C. for 2 days. After work-up according to a conventional method, the mixture was purified by purification step A to give the title compound (4.76 mg).

Example 14

Synthesis of compound H-7

The compound was synthesized using cycloleucine instead of D-valine in Step 1 of Example 1, and then by the operation in the same manner as in Step 1 of Example 2.

Example 15

Synthesis of compounds A-62 to A-219

In the same manner as in Example 2 (A-1), the compounds were synthesized using the corresponding amino acid and the like instead of D-valine in Step 1 of Example 1 and the corresponding carboxylic acid instead of phenylacetic acid in Step 2 of Example 2.

Example 16

Synthesis of compounds A-220 to A-224

In the same manner as in Example 4 (A-47), the compounds were synthesized using the corresponding carboxylic acid instead of benzoic in Example 4.

Example 17

Synthesis of compound A-225

In the same manner as in Example 7 (A-55), the compound was synthesized using 3-dimethylaminomethyl-4-iodobenzotrifluoride instead of [2-iodo-5-(trifluoromethyl)phenyl]methanol in Step 3 of Example 7.

Example 18

Synthesis of compounds B-9 to B-12

In the same manner as in Example 6 (B-8), the compounds were synthesized using the corresponding carboxylic acid instead of 3-(2-pyridyl)acrylic acid in Example 6.

Example 19

Synthesis of compounds C-44 to C-59

In the same manner as in Example 3 (C-40), the compounds were synthesized using D-proline instead of D-valine in Step 1 of Example 1 and the corresponding amine instead of benzylamine in Step 2 of Example 3.

Synthetic Example 1

Synthesis of (1-isopropylpiperidin-4-yl)acetic acid

Methyl 4-piperidineacetate (0.6 g, 3.82 mmol) was dissolved in methylene chloride (20 mL), acetone (1 mL), acetic acid (0.26 mL) and sodium triacetoxyborohydride (1.21 g, 5.73 mmol) were added, and the mixture was stirred overnight at room temperature. The solvent was evaporated, and work-up according to a conventional method gave a crude product. The obtained crude product was dissolved in 6 N aqueous hydrogen chloride solution, and the mixture was stirred overnight at 80° C. The solvent was evaporated to give the title compound, which was used for the synthesis of A-22.

Synthetic Example 2

Synthesis of [4-(piperazin-1-yl)pyridin-3-yl]methanol hydrochloride

4-Chloro-3-hydroxymethylpyridine (*J. Med. Chem.*, 49 (13), 2832-2840 (2002))(143 mg, 1 mmol), 1-(tert-butoxycarbonyl)piperazine (186 mg, 1 mmol) and triethylamine (1 mL, 7 mmol) were dissolved in ethanol(3 mL), and the mixture was stirred overnight in a threaded test tube at 130° C. The solvent was evaporated and work-up according to a conventional method gave a crude product. The obtained crude product was dissolved in a dioxane solution (5 mL) containing 4 N hydrogen chloride, and the mixture was stirred for 2 hrs. The solvent was evaporated to give the title compound, which was used for the synthesis of C-22 and C-37.

Synthetic Example 3

Synthesis of 4-(pyrrolidin-1-yl)phenylacetic acid

Step 1

Synthesis of methyl 4-(pyrrolidin-1-yl)phenylacetate

Methyl 4-aminophenylacetate (0.4 g, 2.4 mmol), 1,4-dibromobutane (0.29 mL, 2.4 mmol) and potassium carbonate (0.34 g, 2.6 mmol) were dissolved in dimethylformamide (30 mL), and the mixture was stirred overnight at 80° C. The solvent was evaporated, and the residue was worked up according to a conventional method and purified by silica gel column chromatography to give the title compound (0.13 g, 0.59 mmol).

Step 2

Synthesis of 4-(pyrrolidin-1-yl)phenylacetic acid

Methyl 4-(pyrrolidin-1-yl)phenylacetate (0.13 g, 0.59 mmol) obtained in Step 1 was dissolved in tetrahydrofuran (1.2 mL), 1 M aqueous lithium hydroxide solution (1.2 mL) was added, and the mixture was stirred for 5 hrs. The mixture was neutralized with 1 N aqueous hydrogen chloride solution (1.2 mL), and the solvent was evaporated to give a crude product of the title compound, which was used for the synthesis of A-54.

Of the intermediates used for syntheses of the Examples, the compounds difficult to obtain were synthesized based on the patent reference and non-patent references shown in Table 1.

TABLE 1

| Structural Formula | CAS No. | Reference | Example |
|---|---|---|---|
|  | 6941-28-2 | Kishor R. Nivalkar et al., Synthetic Communication. 26(19), 3535-3542, (1996) | A-21 |
|  | 162046-56-2 | Sagi et al., Journal of Medicinal Chemistry, 46, 1845-1857, (2003) | A-26 |
|  | 80028-43-9 | R. Montgomery et al., Journal of Chemical Society, 1948, 237-242, (1948) | A-29 |
|  | 209960-90-7 | WO9828269 | C-8 |

TABLE 1-continued

| Structural Formula | CAS No. | Reference | Example |
|---|---|---|---|
| [Structure: 1-phenylpiperidin-4-amine] | 63921-23-3 | Viktor Hahn et al., Chemische Berichte, 74, 1658-1660, (1941) | C-18 |

The structures and analysis values of the compounds described in Examples are shown in the following, wherein TFA means trifluoroacetic acid and the described analytical values were actually measured values.

TABLE 2-1

| Ex. No. | Structural Formula | Analytical value |
|---|---|---|
| A-1 | [Structure] TFA | MS(ESI) m/z 365(M + H)+ |
| A-2 | [Structure] 2TFA | MS(ESI) m/z 346(M + H)+ |
| A-3 | [Structure] 2TFA | MS(ESI) m/z 318(M + H)+ |
| A-4 | [Structure] 2TFA | MS(ESI) m/z 404(M + H)+ |
| A-5 | [Structure] 2TFA | MS(ESI) m/z 418(M + H)+ |

TABLE 2-1-continued
| Ex. No. | Structural Formula | Analytical value |
|---|---|---|
| A-6 | 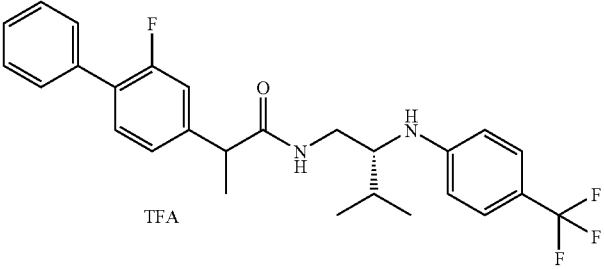 TFA | MS(ESI) m/z 473(M + H)+ |
| A-7 | 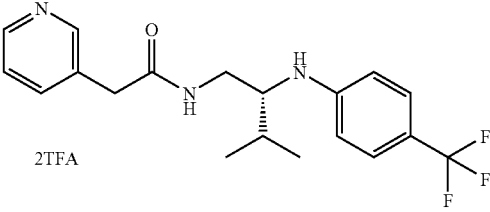 2TFA | MS(ESI) m/z 366(M + H)+ |
| A-8 | 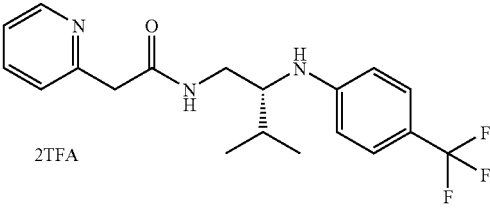 2TFA | 1H-NMR(300 MHz, DMSO-d6) δ = 0.85-0.95(6H, m), 1.80-1.90(1H, m), 3.10-6.72(2H, d, J=8.7 Hz), 7.29(2H, d, J=8.7), 7.84-7.94(2H, m), 8.45(1H, t, J=8.1 Hz), 8.63(1H, m), 8.81(1H, d, J=5.1 Hz). MS(ESI) m/z 366(M + H)+ |
TABLE 2-2
| A-9 | 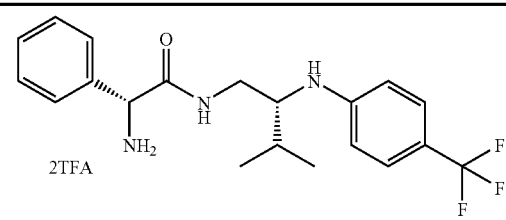 2TFA | MS(ESI) m/z 380(M + H)+ |
|---|---|---|
| A-10 | 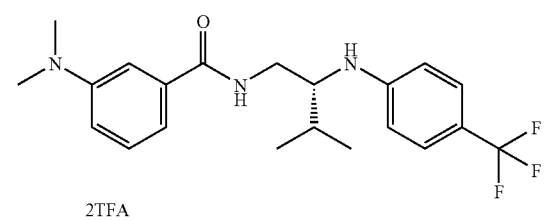 2TFA | MS(ESI) m/z 394(M + H)+ |
| A-11 | 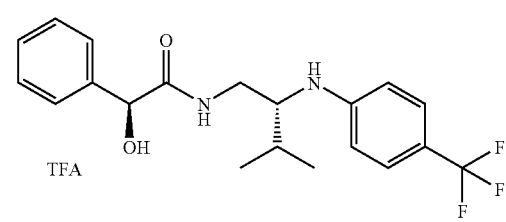 TFA | MS(ESI) m/z 381(M + H)+ |

TABLE 2-2-continued

| | | |
|---|---|---|
| A-12 | (indol-3-yl-glyoxylamide structure) 2TFA | MS(ESI) m/z 418(M + H)+ |
| A-13 | (pyridin-3-yl acrylamide structure) 2TFA | MS(ESI) m/z 378(M + H)+ |
| A-14 | (1-(pyridin-4-yl)piperidine-4-carboxamide structure) 2TFA | 1H-NMR(300 MHz, DMSO-d6) δ = 0.82-0.95(6H, m), 1.40-1.55(2H, m), 1.65-1.85(3H, m), 2.40-2.50(1H, m), 3.20-3.20(5H, m), 3.36(1H, m), 4.10-4.17(2H, m), 6.72(2H, d, J=8.7 Hz), 7.14(2H, d, J=7.5 Hz), 7.29(2H, d, J=8.7), 8.02(1H, m), 8.18(2H, m). MS(ESI) m/z 435(M + H)+ |
| A-15 | (valine amide structure) 2TFA | MS(ESI) m/z 346(M + H)+ |
| A-16 | (1-phenylcyclopropanecarboxamide structure) TFA | MS(ESI) m/z 391(M + H)+ |
| A-17 | (alanine amide structure) 2TFA | MS(ESI) m/z 318(M + H)+ |

TABLE 2-3

| | | |
|---|---|---|
| A-18 | (serine amide structure) 2TFA | MS(ESI) m/z 334(M + H)+ |

TABLE 2-3-continued

| | | |
|---|---|---|
| A-19 | [structure] TFA | MS(ESI) m/z 351(M + H)+ |
| A-20 | [structure] TFA | MS(ESI) m/z 401(M + H)+ |
| A-21 | [structure] 2TFA | MS(ESI) m/z 422(M + H)+ |
| A-22 | [structure] 2TFA | MS(ESI) m/z 414(M + H)+ |
| A-23 | [structure] 2TFA | MS(ESI) m/z 400(M + H)+ |
| A-24 | [structure] TFA | MS(ESI) m/z 483(M + H)+ |
| A-25 | [structure] 2TFA | MS(ESI) m/z 384(M + H)+ |

TABLE 2-3-continued
| A-26 | 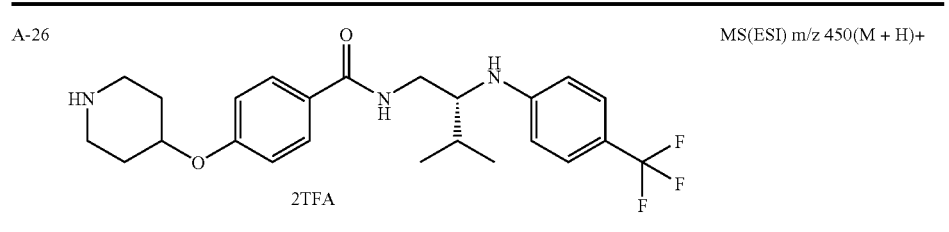 | MS(ESI) m/z 450(M + H)+ |
TABLE 2-4
| A-27 | 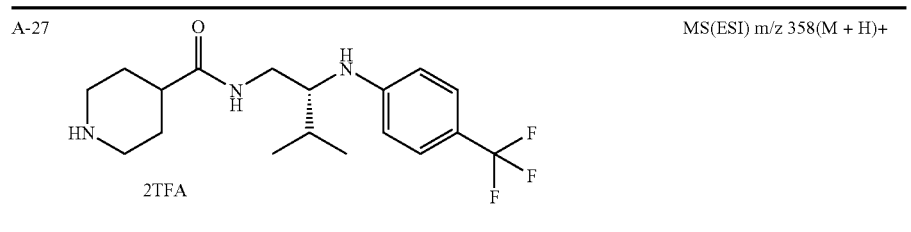 | MS(ESI) m/z 358(M + H)+ |
| A-28 | 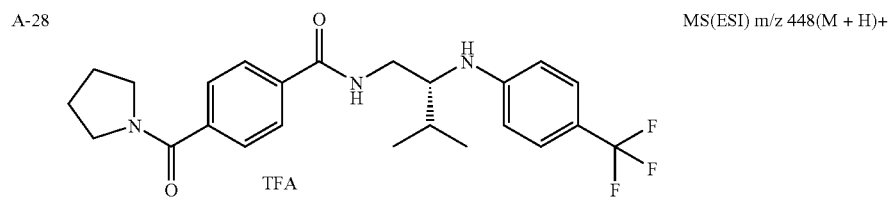 | MS(ESI) m/z 448(M + H)+ |
| A-29 | 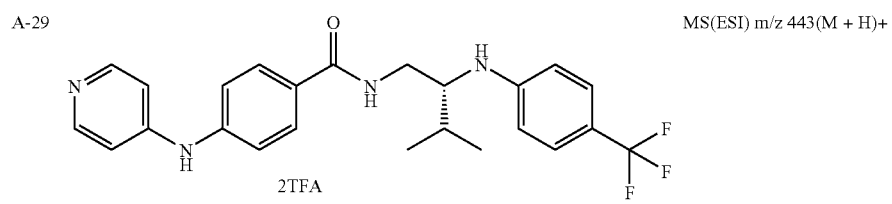 | MS(ESI) m/z 443(M + H)+ |
| A-30 | 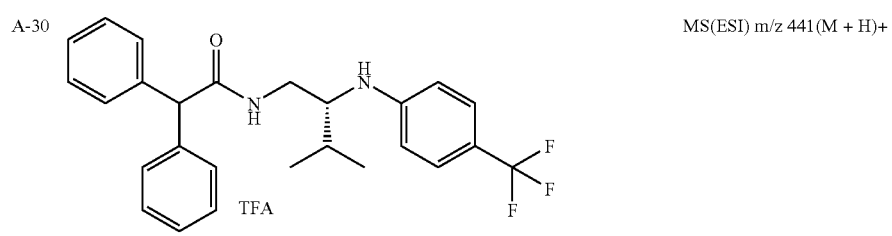 | MS(ESI) m/z 441(M + H)+ |
| A-31 | 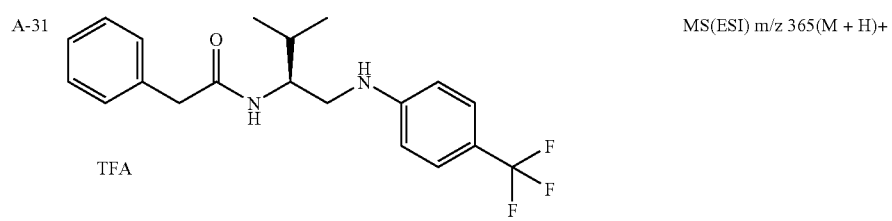 | MS(ESI) m/z 365(M + H)+ |
| A-32 | 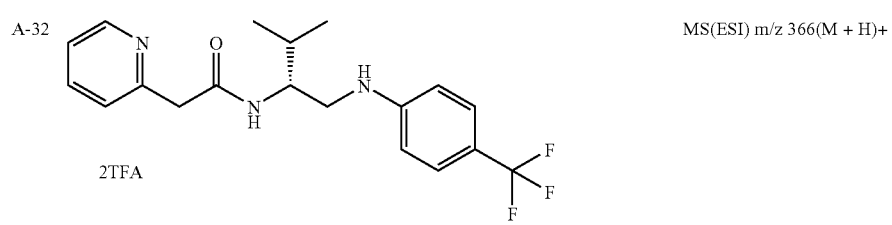 | MS(ESI) m/z 366(M + H)+ |

TABLE 2-4-continued
| A-33 | 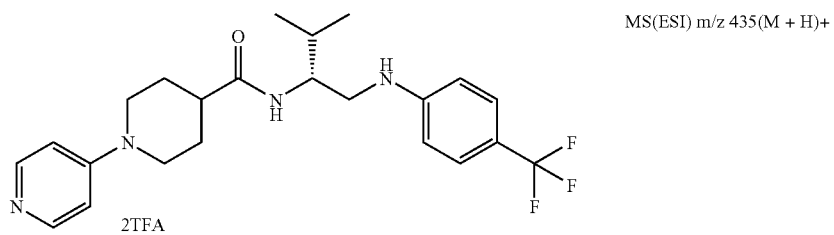 | MS(ESI) m/z 435(M + H)+ |
|---|---|---|
| A-34 | 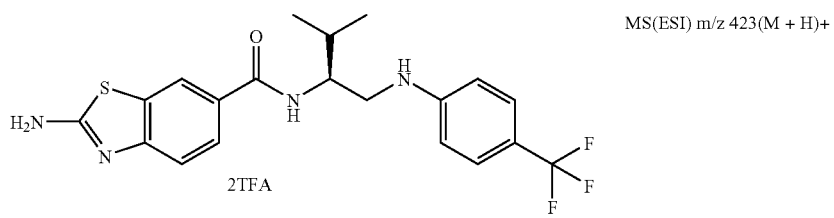 | MS(ESI) m/z 423(M + H)+ |
| A-35 | 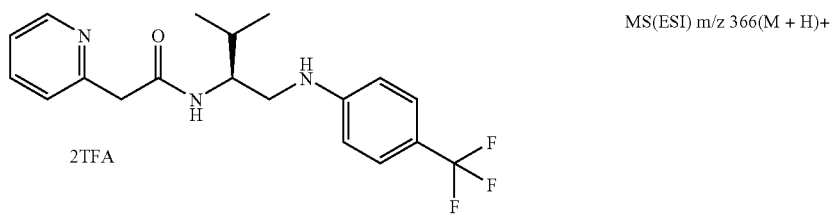 | MS(ESI) m/z 366(M + H)+ |
TABLE 2-5
| A-36 | 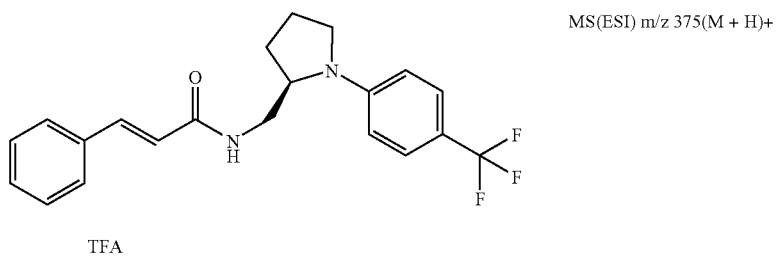 | MS(ESI) m/z 375(M + H)+ |
|---|---|---|
| A-37 | 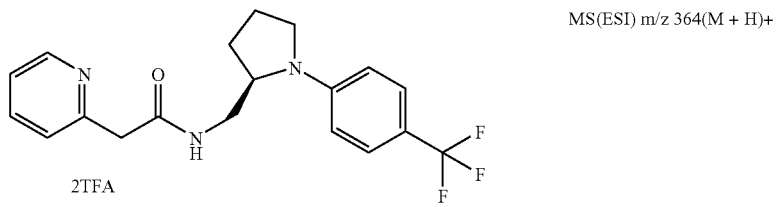 | MS(ESI) m/z 364(M + H)+ |
| A-38 | 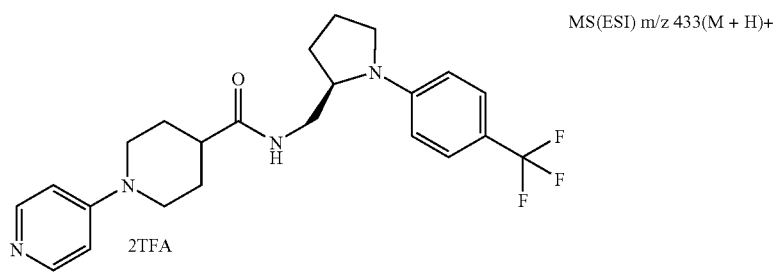 | MS(ESI) m/z 433(M + H)+ |

TABLE 2-5-continued

| | Structure | Data |
|---|---|---|
| A-39 | (phenylacetamide-CH2-(S)-pyrrolidin-2-yl linked to 4-(trifluoromethyl)phenyl) TFA | 1H-NMR (300 MHz, CDCl3) δ = 1.70-1.77(2H, m), 1.93-1.97(2H, m), 3.02-3.17(2H, m), 3.32-3.38(1H, m), 3.46-3.54(1H, m), 3.57(2H, s), 3.93-3.99 (1H, m), 5.50(1H, br), 6.70(2H, d, J=8.8 Hz), 7.17-7.20(2H, m), 7.29-7.37 (3H, m), 7.42(2H, d, J=8.8 Hz). MS(ESI) m/z 363(M + H)+ |
| A-40 | (phenylacetamide-CH2-pyrrolidin-2-yl linked to 4-(trifluoromethyl)phenyl) TFA | MS(ESI) m/z 363(M + H)+ |
| A-41 | (indol-3-yl-acetamide-CH2-pyrrolidin-2-yl linked to 4-(trifluoromethyl)phenyl) 2TFA | MS(ESI) m/z 402(M + H)+ |
| A-42 | (cyclohexanecarboxamide-CH2-pyrrolidin-2-yl linked to 4-(trifluoromethyl)phenyl) TFA | MS(ESI) m/z 355(M + H)+ |
| A-43 | (benzylsulfonamide-CH2-pyrrolidin-2-yl linked to 4-(trifluoromethyl)phenyl) TFA | MS(ESI) m/z 399(M + H)+ |
| A-44 | (phenylacetamide-CH2-cyclopentyl-NH-4-(trifluoromethyl)phenyl) TFA | MS(ESI) m/z 377(M + H)+ |

TABLE 2-6

| | Structure | Data |
|---|---|---|
| A-45 | (pyridin-2-yl-acetamide-CH2-cyclopentyl-NH-4-(trifluoromethyl)phenyl) 2TFA | MS(ESI) m/z 378(M + H)+ |

TABLE 2-6-continued

| | | |
|---|---|---|
| A-46 | (structure) 2TFA | MS(ESI) m/z 447(M + H)+ |
| A-47 | (structure) TFA | 1H-NMR(300 MHz, DMSO-d6) δ = 0.85-0.95(6H, m), 1.50-1.63(1H, m), 1.76-1.90(2H, m), 3.10-3.25(1H, m), 3.30-3.40(2H, m), 6.68(2H, d, J=8.4 Hz), 7.29(2H, d, J=8.4), 7.39-7.52(3H, m), 7.79(2H, dd, J=8.1, 1.2 Hz), 8.41(1H, m). MS(ESI) m/z 365(M + H)+ |
| A-48 | (structure) 2TFA | MS(ESI) m/z 449(M + H)+ |
| A-49 | (structure) 2TFA | MS(ESI) m/z 416(M + H)+ |
| A-50 | (structure) TFA | MS(ESI) m/z 385(M + H)+ |
| A-51 | (structure) 2TFA | MS(ESI) m/z 418(M + H)+ |
| A-52 | (structure) 2TFA | MS(ESI) m/z 414(M + H)+ |

TABLE 2-6-continued

| | | |
|---|---|---|
| A-53 | [structure: PhSO2NH-CH2CH2-CH(iPr)-NH-C6H4-CF3, TFA salt] | MS(ESI) m/z 401(M + H)+ |

TABLE 2-7

| | | |
|---|---|---|
| A-54 | [structure: 4-(pyrrolidin-1-yl)phenyl-CH2-C(O)NH-CH2CH2-CH(iPr)-NH-C6H4-CF3, 2TFA] | 1H-NMR(300 MHz, DMSO-d6)<br>δ = 0.78-0.85(6H, m), 1.36-1.50(2H, m),<br>1.58-1.70(2H, m), 1.70-1.82(1H, m),<br>1.90-1.95(2H, m), 2.90-3.00(1H, m),<br>3.05-3.30(7H, m), 6.45(2H, d, J=8.7),<br>6.58(2H, d, J=8.7 Hz), 7.02(2H, d, J=8.7 Hz),<br>7.24(2H, d, J=8.7 Hz), 7.77 (1H, m).<br>MS(ESI) m/z 448(M + H)+ |
| A-55 | [structure: PhCH2C(O)NH-CH2-CH(iPr)-NH-(2-CH2OH-4-CF3-C6H3)] | 1H-NMR(300 MHz, CDCl3)<br>δ = 0.93-1.02(6H, m), 1.22(1H, d,<br>J=7.0 Hz), 3.18-3.27(1H, m). 3.40-3.57<br>(4H, m), 4.46(1H, d, J=12.5 Hz), 4.60<br>(1H, d, J=12.5 Hz), 5.54(1H, brs), 6.62<br>(1H, d, J=8.6 Hz), 6.94-6.97(2H, m),<br>7.15-7.22(3H, m), 725(1H, d, J=8.6 Hz),<br>7.37(1H, d, J=8.6 Hz).<br>MS(ESI) m/z 395(M + H)+ |
| A-56 | [structure: PhCH2C(O)NH-CH2-CH(iPr)-NH-(2-NH2-4-CF3-C6H3), 2TFA] | MS(ESI) m/z 380(M + H)+ |
| A-57 | [structure: tryptophan-CH2-CH(iPr)-NH-(2-NH2-4-CF3-C6H3), 2TFA] | MS(ESI) m/z 448(M + H)+ |
| A-58 | [structure: indol-3-yl-CH2-C(O)NH-CH2-CH(iPr)-NH-(2-NH2-4-CF3-C6H3), 2TFA] | 1H-NMR(300 MHz, DMSO-d6)<br>δ = 0.83-0.93(6H, m), 1.80-1.90(1H, m),<br>3.00-3.80(5H, m), 6.66(1H, d, J=9.0 Hz),<br>6.84-7.04(6H, m), 7.29(1H, d, J=9.0 Hz),<br>7.41(1H, d, J=9.0 Hz), 7.80(1H, m).<br>MS(ESI) m/z 419(M + H)+ |
| A-59 | [structure: pyridin-2-yl-CH2-C(O)NH-CH2-CH(iPr)-NH-(2-NH2-4-CF3-C6H3), 2TFA] | MS(ESI) m/z 381(M + H)+ |

TABLE 2-7-continued
A-60 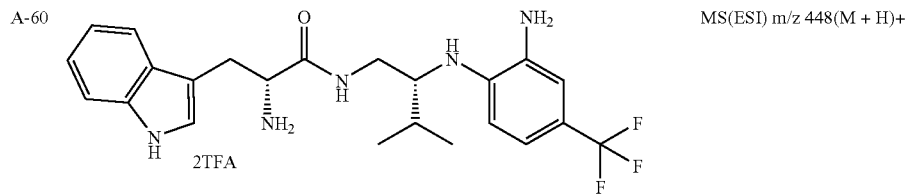 MS(ESI) m/z 448(M + H)+
A-61 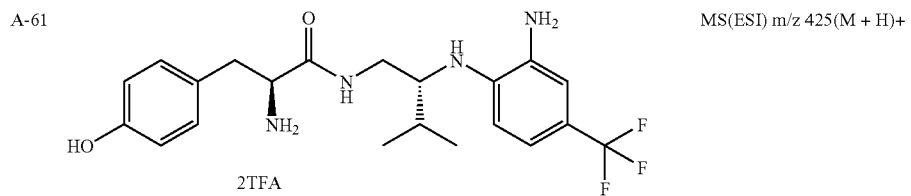 MS(ESI) m/z 425(M + H)+
TABLE 2-8
B-1 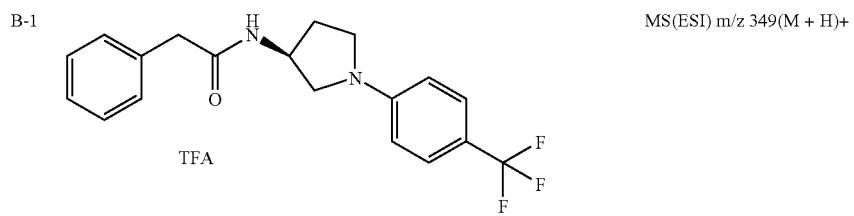 MS(ESI) m/z 349(M + H)+
B-2 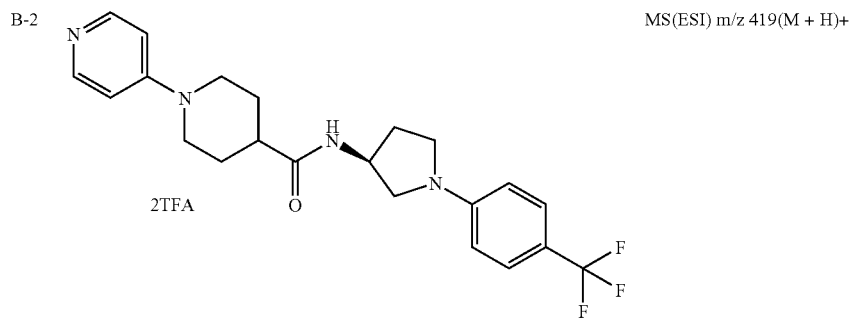 MS(ESI) m/z 419(M + H)+
B-3 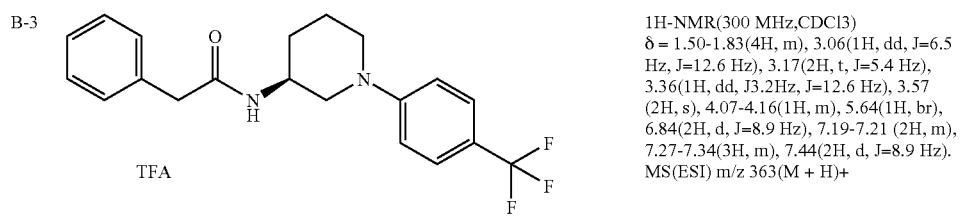 1H-NMR(300 MHz,CDCl3)
δ = 1.50-1.83(4H, m), 3.06(1H, dd, J=6.5 Hz, J=12.6 Hz), 3.17(2H, t, J=5.4 Hz), 3.36(1H, dd, J3.2Hz, J=12.6 Hz), 3.57 (2H, s), 4.07-4.16(1H, m), 5.64(1H, br), 6.84(2H, d, J=8.9 Hz), 7.19-7.21 (2H, m), 7.27-7.34(3H, m), 7.44(2H, d, J=8.9 Hz).
MS(ESI) m/z 363(M + H)+
B-4 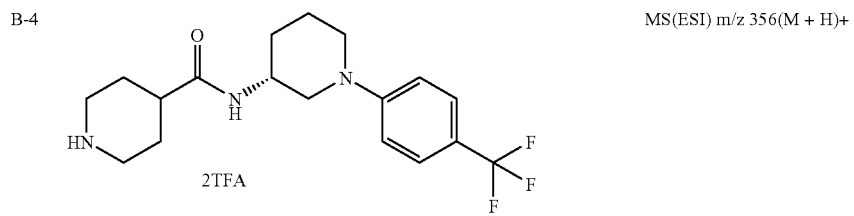 MS(ESI) m/z 356(M + H)+

TABLE 2-8-continued

| | | |
|---|---|---|
| B-5 | (structure: H2N-CH2-C(=O)-NH-[(3R)-piperidin-3-yl]-N1-[4-(trifluoromethyl)phenyl]; 2TFA) | MS(ESI) m/z 302(M + H)+ |
| B-6 | (structure: pyridin-2-yl-CH2-C(=O)-NH-[(3R)-piperidin-3-yl]-N1-[4-(trifluoromethyl)phenyl]; 2TFA) | MS(ESI) m/z 364(M + H)+ |
| B-7 | (structure: 1-(pyridin-4-yl)piperidine-4-carboxamide linked to (3R)-piperidin-3-yl-N1-[4-(trifluoromethyl)phenyl]; 2TFA) | MS(ESI) m/z 433(M + H)+ |
| B-8 | (structure: (E)-3-(pyridin-2-yl)acrylamide-N-[(3R)-pyrrolidin-3-yl]-N1-[5-(trifluoromethyl)pyridin-2-yl]; 2TFA) | MS(ESI) m/z 363(M + H)+ |

TABLE 2-9

| | | |
|---|---|---|
| C-1 | (structure: phenethyl-NH-C(=O)-[(S)-CH(iPr)]-NH-[4-(trifluoromethyl)phenyl]; TFA) | MS(ESI) m/z 365(M + H)+ |
| C-2 | (structure: [1-(pyridin-4-yl)piperidin-4-yl]methyl-NH-C(=O)-[(S)-CH(iPr)]-NH-[4-(trifluoromethyl)phenyl]; 2TFA) | MS(ESI) m/z 435(M + H)+ |

TABLE 2-9-continued
| | | |
|---|---|---|
| C-3 | 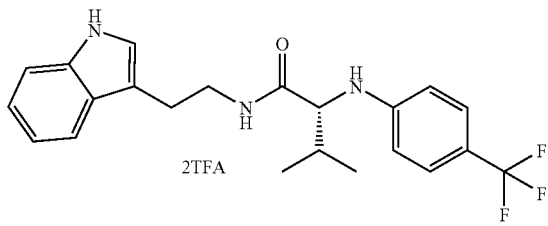 2TFA | MS(ESI) m/z 404(M + H)+ |
| C-4 | 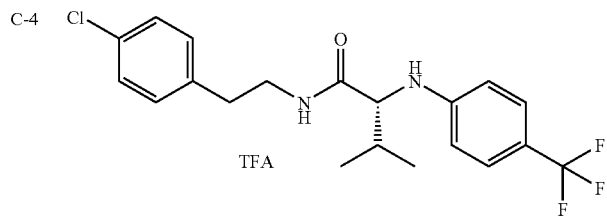 TFA | 1H-NMR(300 MHz, DMSO-d6) δ =0.83(3H, d, J =6.9 Hz), 0.90(3H, d, J =6.9 Hz), 1.90-1.95(1H, m), 2.60-2.70(2H, m), 3.25-3.30(2H, m), 3.49(1H, d, J=7.5 Hz), 6.66(2H, d, J=8.7), 7.13(2H, d, J=8.7 Hz), 7.23(2H, d, J=8.7 Hz), 7.32(2H, d, J=8.7 Hz), 8.01(1H, m). MS(ESI) m/z 399M + H)+ |
| C-5 | 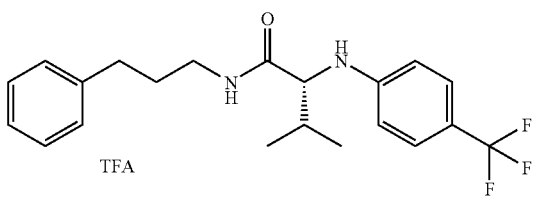 TFA | 1H-NMR(300 MHz, DMSO-d6) δ = 0.83-0.99(6H, m), 1.55-1.65(2H, m), 1.90-2.00(1H, m), 2.40-2.50(2H, m), 3.00-3.10(2H, m), 3.54(2H, d, J=7.8 Hz), 6.73(2H, d, J=8.7), 7.08(2H, d, J=6.6 Hz), 7.23(2H, d, J=6.6 Hz), 7.33(2H, d, J=8.7 Hz), 8.07(1H, m). MS(ESI) m/z 379M + H)+ |
| C-6 | 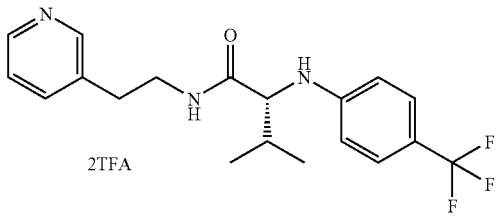 2TFA | 1H-NMR(300M Hz, DMSO-d6) δ = 0.80(3H, d, J=6.6 Hz), 0.87(3H, d, J=6.6 Hz), 1.86-1.96(1H, m), 2.89(2H, t, J=6.3 Hz), 2.95-3.10(1H, m), 3.35-3.55 (3H, m), 6.64(2H, d, J=8.7), 7.31 (2H, d, J=8.7 Hz), 7.77(1H, m), 8.16(1H, m), 8.23(1H, d, J=7.2 Hz), 8.69(1H, m), 8.73(1H, s). MS(ESI) m/z 366M + H)+ |
| C-7 | 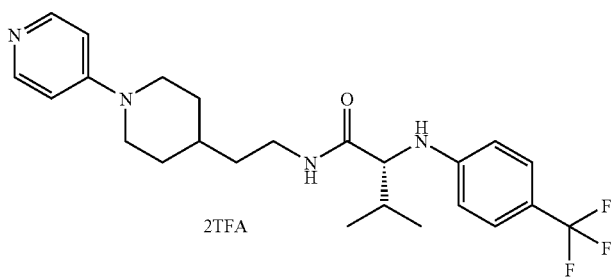 2TFA | MS(ESI) m/z 449(M + H)+ |
| C-8 | 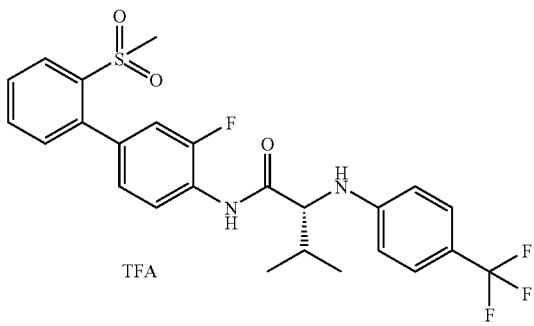 TFA | MS(ESI) m/z 509(M + H)+ |

TABLE 2-10

| | | |
|---|---|---|
| C-9 | [structure with 2,5-dihydropyrrole-carbonyl-phenyl-CH2-NH-C(=O)-CH(iPr)-NH-C6H4-CF3], TFA | MS(ESI) m/z 446(M+H)+ |
| C-10 | [3-chlorophenethyl-NH-C(=O)-CH(iPr)-NH-C6H4-CF3], TFA | MS(ESI) m/z 399(M+H)+ |
| C-11 | [1-benzylpiperidin-4-yl-NH-C(=O)-CH(iPr)-NH-C6H4-CF3], 2TFA | MS(ESI) m/z 434(M+H)+ |
| C-12 | [1H-imidazol-4-yl-ethyl-NH-C(=O)-CH(iPr)-NH-C6H4-CF3], 2TFA | 1H-NMR(300 MHz, DMSO-d6) δ = 0.84(3H, d, J=6.9 Hz), 0.90(3H, d, J=6.9 Hz), 1.90-2.00(1H, m), 2.70-2.80(2H, m), 3.35-3.45(2H, m), 3.48(1H, m), 6.66(2H, d, J=7.8 Hz), 7.33(4H, m), 8.20(1H, m), 8.95(1H, s). MS(ESI) m/z 355(M+H)+ |
| C-13 | [1-methylpiperidin-4-yl-CH2-NH-C(=O)-CH(iPr)-NH-C6H4-CF3], 2TFA | MS(ESI) m/z 372(M+H)+ |
| C-14 | [2,5-dihydropyrrole-C(=O)-CH(iPr)-N(C6H4-CF3)-C(=O)-CH(iPr)-NH-C6H4-CF3], TFA | MS(ESI) m/z 556(M+H)+ |

TABLE 2-10-continued

| | | |
|---|---|---|
| C-15 | [structure: methyl ester of naphthalen-1-ylmethyl amino acid, N-linked to valine-NH-(4-trifluoromethylphenyl), TFA salt] | 1H-NMR(300 MHz, DMSO-d6) δ = 0.65(3H, d, J=6.6 Hz), 0.80(3H, d, J=6.6 Hz), 1.83(1H, m), 3.20-3.35(2H, m), 3.45-3.60(4H, m), 4.63(1H, m), 6.26(1H, d, J=8.1 Hz), 6.67(2H, d, J=7.8 Hz), 7.20-7.30(4H, m), 7.45-7.60(2H, m), 7.73(1H, m), 7.89(1H, d, J=6.9 Hz), 8.03(1H, d, J=7.8 Hz), 8.54(1H, m) MS(ESI) m/z 473(M+H)+ |
| C-16 | [structure: 1-isopropylpiperidin-4-yl-ethyl-NH-C(O)-valine-NH-(4-trifluoromethylphenyl), 2TFA salt] | MS(ESI) m/z 414(M+H)+ |

TABLE 2-11

| | | |
|---|---|---|
| C-17 | [structure: piperidine-1-carbonyl-valine-NH-(4-trifluoromethylphenyl), TFA salt] | MS(ESI) m/z 329(M+H)+ |
| C-18 | [structure: 1-phenylpiperidin-4-yl-NH-C(O)-valine-NH-(4-trifluoromethylphenyl), 2TFA salt] | MS(ESI) m/z 420(M+H)+ |
| C-19 | [structure: 4-(pyridin-2-yl)piperidine-1-carbonyl-valine-NH-(4-trifluoromethylphenyl), 2TFA salt] | MS(ESI) m/z 406(M+H)+ |
| C-20 | [structure: 2-hydroxy-2-phenylethyl-NH-C(O)-valine-NH-(4-trifluoromethylphenyl), TFA salt] | 1H-NMR(300 MHz, CDCl3) δ = 0.95-1.05(6H, m), 2.30-2.40(1H, m), 2.95-3.10(1H, m), 3.35-3.45(1H, m), 3.60-3.80(2H, m), 4.20(1H, m), 4.80(1H, m), 6.60(2H, d, J=8.8 hz), 6.82(1H, m), 7.20-7.35(4H, m), 7.43(2H, d, J=8.8 Hz). MS(ESI) m/z 381(M+H)+ |

TABLE 2-11-continued
C-21 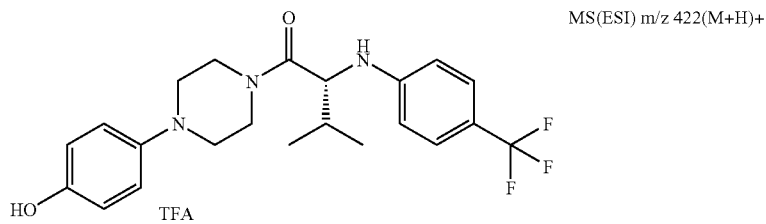 MS(ESI) m/z 422(M+H)+
C-22 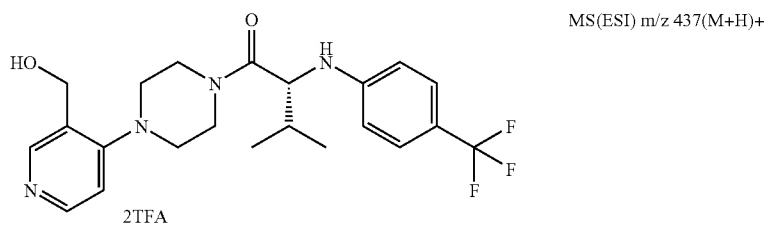 MS(ESI) m/z 437(M+H)+
C-23 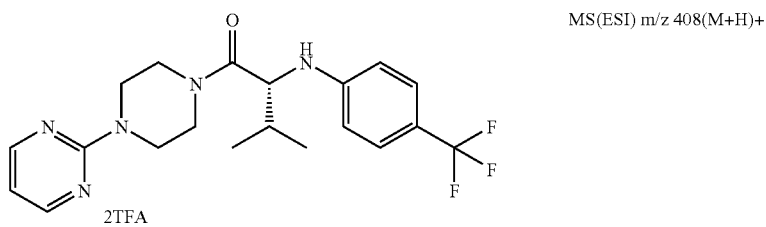 MS(ESI) m/z 408(M+H)+
C-24 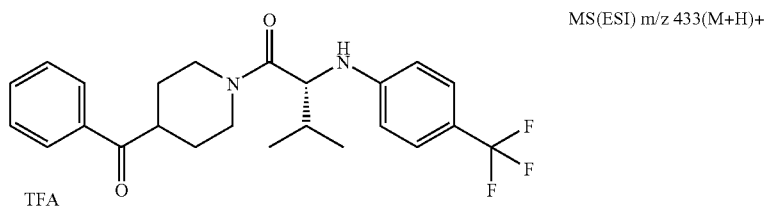 MS(ESI) m/z 433(M+H)+
C-25 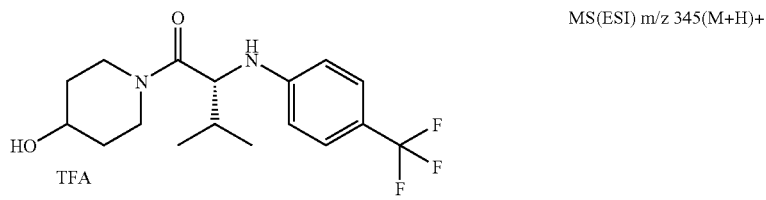 MS(ESI) m/z 345(M+H)+
TABLE 2-12
C-26 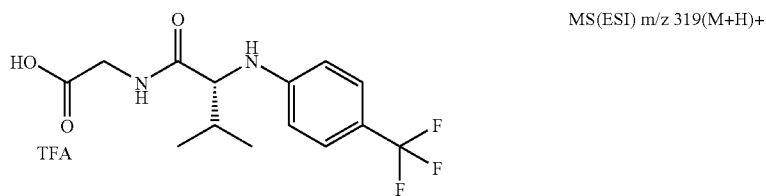 MS(ESI) m/z 319(M+H)+

TABLE 2-12-continued
| C-27 | 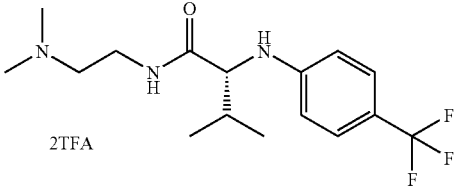 2TFA | MS(ESI) m/z 332(M+H)+ |
|---|---|---|
| C-28 | 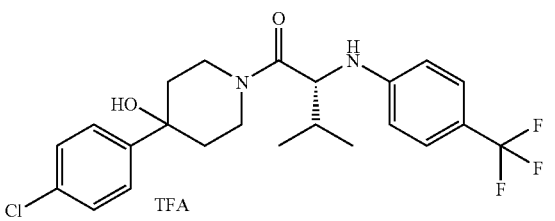 TFA | MS(ESI) m/z 455(M+H)+ |
| C-29 | 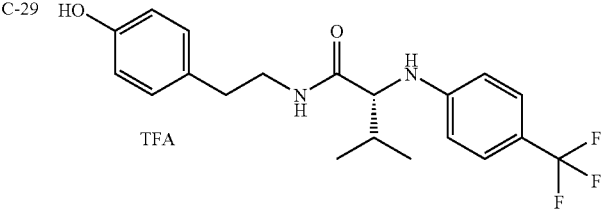 TFA | 1H-NMR(300 MHz, CDCl3) δ = 0.95(3H, d, J=6.9 Hz), 1.01(3H, d, J=6.9 Hz), 2.33(1H, m), 2.67(2H, m), 3.42(1H, m), 3.58(2H, m), 4.15(1H, m), 5.24(1H, m), 6.47(1H, m), 6.57(2H, d, J=8.7 Hz), 6.65(2H, d, J=9.0 Hz), 6.86(2H, d, J=8.7 Hz), 7.42(2H, d, J=9.0 Hz). MS(ESI) m/z 381(M+H)+ |
| C-30 | 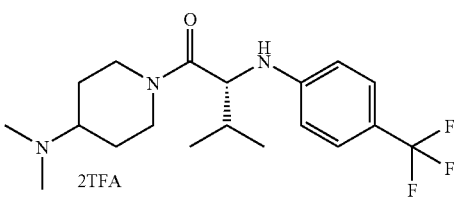 2TFA | MS(ESI) m/z 372(M+H)+ |
| C-31 | 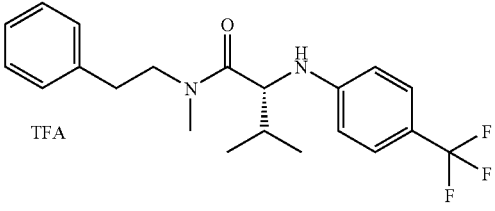 TFA | MS(ESI) m/z 379(M+H)+ |
| C-32 | 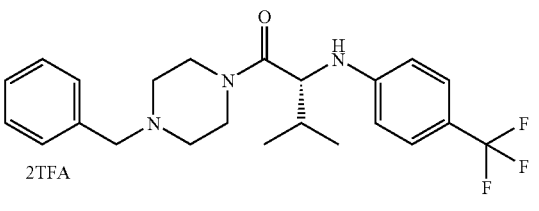 2TFA | MS(ESI) m/z 420(M+H)+ |
| C-33 | 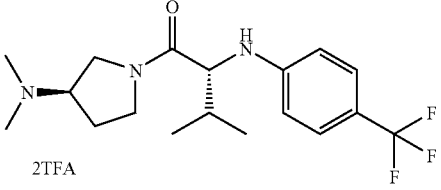 2TFA | MS(ESI) m/z 358(M+H)+ |

TABLE 2-12-continued
| C-34 | 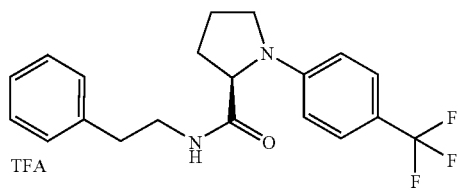 | MS(ESI) m/z 363(M+H)+ |
TABLE 2-13
| C-35 | 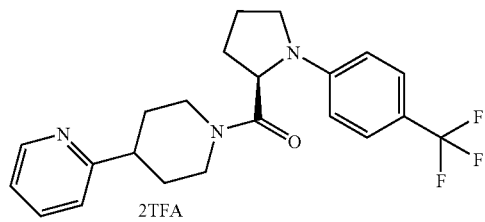 | MS(ESI) m/z 404(M+H)+ |
| C-36 | 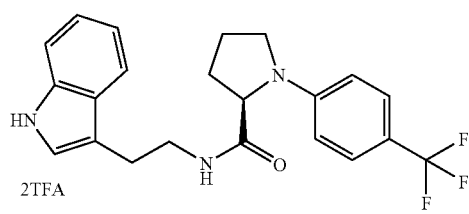 | MS(ESI) m/z 402(M+H)+ |
| C-37 | 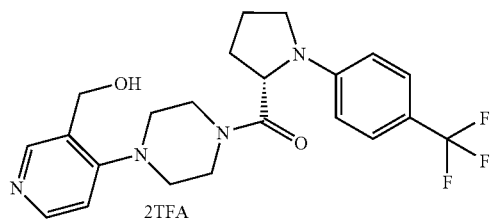 | MS(ESI) m/z 435(M+H)+ |
| C-38 | 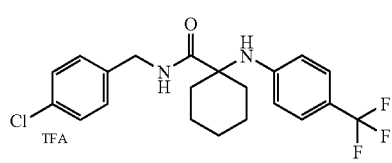 | MS(ESI) m/z 411(M+H)+ |
| C-39 | 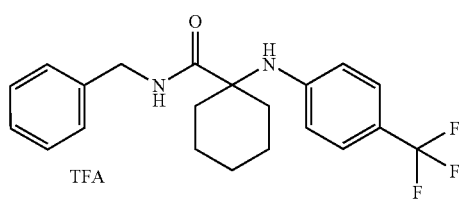 | MS(ESI) m/z 377(M+H)+ |
| C-40 | 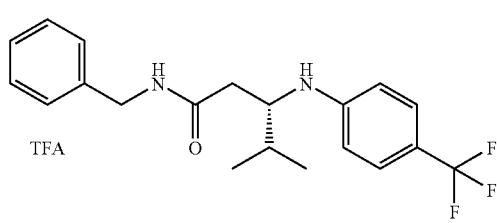 | 1H-NMR(300 MHz, DMSO-d6) δ = 0.86(3H, t, J=6.9 Hz), 0.90(3H, d, J=6.9 Hz), 1.75-1.85(1H, m), 2.20-2.40(2H, m), 3.75(1H, m), 4.21(2H, t, J=6.0 Hz), 6.10(1H, m), 6.69(2H, d, J=8.7 Hz), 7.10-7.20(5H, m), 7.31(2H, d, J=8.7 Hz), 8.28(1H, m). MS(ESI) m/z 365(M+H)+ |

TABLE 2-13-continued

| | | |
|---|---|---|
| C-41 | 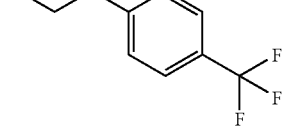 2TFA | MS(ESI) m/z 366(M+H)+ |
| C-42 | 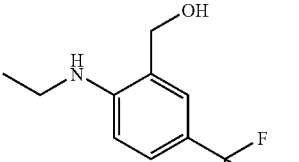 TFA | MS(ESI) m/z 379(M+H)+ |
| C-43 | 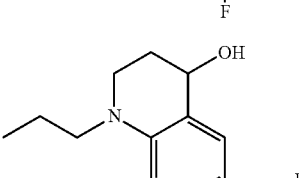 2TFA | MS(ESI) m/z 380(M+H)+ |

TABLE 2-14

| | | |
|---|---|---|
| E-1 | 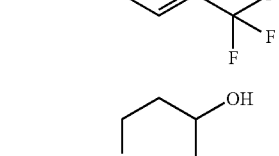 | 1H-NMR(300 MHz, DMSO-d6) δ = 0.22(2H, m), 0.45(2H, m), 1.05-1.10(1H, m), 2.30(2H, t, J=6.3 Hz), 4.43(2H, d, J=5.7 Hz), 5.29(1H, t, J=5.7 Hz), 5.68(1H, m), 6.67(1H, d, J=9.6 Hz), 7.34-7.40(2H, m), MS(ESI) m/z 246(M+H)+ |
| E-2 | | 1H-NMR(300 MHz, CDCl3) δ = 1.31(3H, t, J=6.9 Hz), 3.22(2H, q, J=6.9 hz), 4.66(2H, s), 6.65(1H, dd, J=8.4 Hz), 7.27(1H, d, J=2.4 Hz), 7.44(1H, dd, J=8.4, 2.4 Hz). MS(ESI) m/z 220(M+H)+ |
| E-3 | | 1H-NMR(300 MHz, DMSO-d6) δ = 0.89(3H, t, J=7.2 hz), 1.48-1.58(2H, m), 1.81(2H, qq, J=7.2 Hz), 3.10-3.40(4H, m), 4.53(1H, q, J=4.5 Hz), 5.27(1H, d, J=4.8 Hz), 6.65(1H, d, J=8.4 Hz), 7.28(1H, dd, J=8.7, 2.4 Hz), 7.36(1H, d, J=2.4 Hz). MS(ESI) m/z 260(M+H)+ |
| E-4 | | 1H-NMR(300 MHz, DMSO-d6) δ = 0.90(3H, t, J=7.2 hz), 1.25-1.47(2H, m), 1.63-1.53(2H, m), 3.20-3.40(4H, m), 4.53(1H, q, J=4.8 Hz), 5.26(1H, d, J=5.4 Hz), 6.65(1H, d, J=9.0 Hz), 7.28(1H, dd, J=8.7, 2.1 Hz), 7.37(1H, d, J=2.1 Hz). MS(ESI) m/z 274(M+H)+ |

TABLE 2-14-continued

| | | |
|---|---|---|
| E-5 | 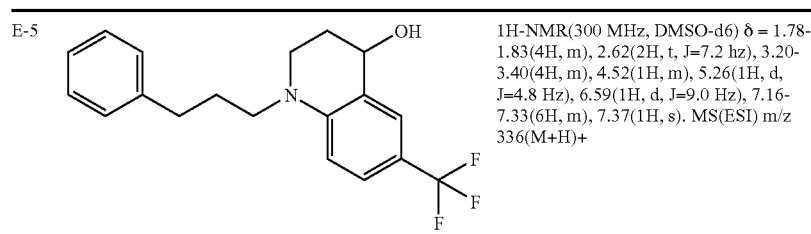 | 1H-NMR(300 MHz, DMSO-d6) δ = 1.78-1.83(4H, m), 2.62(2H, t, J=7.2 hz), 3.20-3.40(4H, m), 4.52(1H, m), 5.26(1H, d, J=4.8 Hz), 6.59(1H, d, J=9.0 Hz), 7.16-7.33(6H, m), 7.37(1H, s). MS(ESI) m/z 336(M+H)+ |
| E-6 | 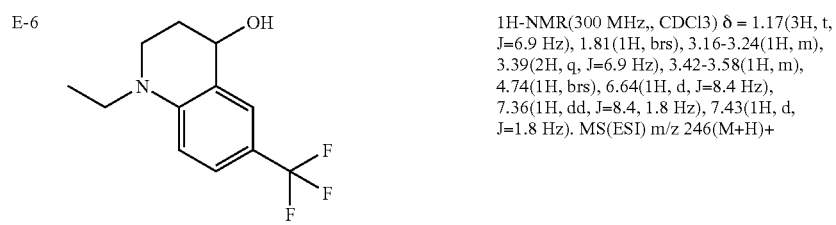 | 1H-NMR(300 MHz,, CDCl3) δ = 1.17(3H, t, J=6.9 Hz), 1.81(1H, brs), 3.16-3.24(1H, m), 3.39(2H, q, J=6.9 Hz), 3.42-3.58(1H, m), 4.74(1H, brs), 6.64(1H, d, J=8.4 Hz), 7.36(1H, dd, J=8.4, 1.8 Hz), 7.43(1H, d, J=1.8 Hz). MS(ESI) m/z 246(M+H)+ |

In the structural formulas in the following Tables, the symbols X1, X2 and X3 show binding sites and [M+H]+ shows actually measured values of mass analysis (MS(ESI)).

The Example compounds in the following Tables include trifluoroacetate thereof, since purification step A was employed as a final purification step in some cases. In the Tables, however, salts are not indicated.

TABLE 2-15

| Compound No. | W1 | [M+H]+ |
|---|---|---|
| A-62 | pyridin-4-ylmethyl-X1 | 366 |
| A-63 | pyridin-3-yl-CH=CH-X1 | 378 |
| A-64 | pyridin-2-yl-X1 | 352 |
| A-65 | pyridin-3-yl-X1 | 352 |
| A-66 | pyridin-4-yl-X1 | 352 |

TABLE 2-15-continued

| Compound No. | W1 | [M+H]+ |
|---|---|---|
| A-67 | pyridin-2-yl-CH=CH-X1 | 378 |
| A-68 | 4-(piperidin-4-ylmethyl)phenyl-X1 | 448 |
| A-69 | cyclohexylmethyl-X1 | 371 |
| A-70 | isoquinolin-7-yl-X1 | 402 |
| A-71 | quinolin-6-yl-X1 | 402 |
| A-72 | phenethyl-X1 | 379 |
| A-73 | styryl-X1 | 377 |

TABLE 2-15-continued
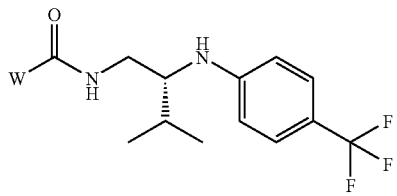
| Compound No. | W1 | [M+H]+ |
|---|---|---|
| A-74 | 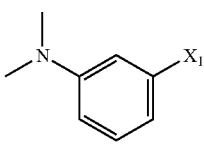 | 394 |
| A-75 |  | 304 |
| A-76 | 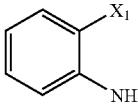 | 366 |
| A-77 | 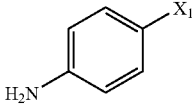 | 366 |
| A-78 | 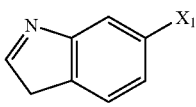 | 390 |
| A-79 | 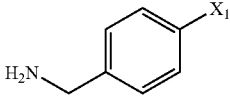 | 380 |
| A-80 | 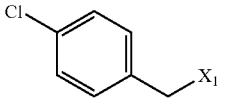 | 399 |
| A-81 | 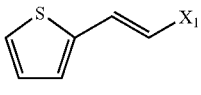 | 383 |
| A-82 | 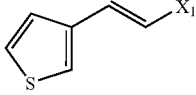 | 383 |
| A-83 | 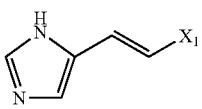 | 367 |
| A-84 | 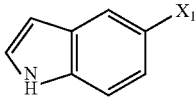 | 390 |
TABLE 2-15-continued
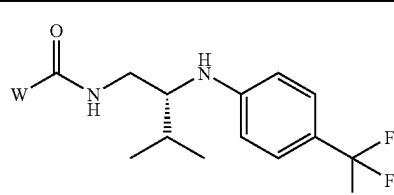
| Compound No. | W1 | [M+H]+ |
|---|---|---|
| A-85 | 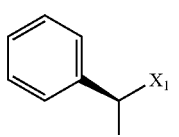 | 380 |
TABLE 2-16
| Compound No. | W | [M+H]+ |
|---|---|---|
| A-86 | 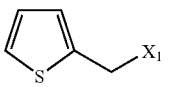 | 371 |
| A-87 | 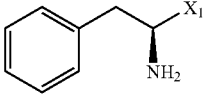 | 394 |
| A-88 | 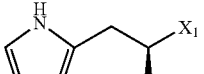 | 384 |
| A-89 | 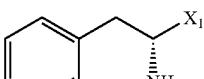 | 394 |
| A-90 | 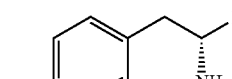 | 410 |
| A-91 | 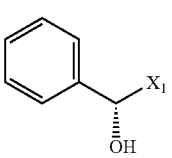 | 381 |
| A-92 |  | 318 |
| A-93 |  | 304 |

TABLE 2-16-continued

| Compound No. | W | [M+H]+ |
|---|---|---|
| A-94 | 1-methylindol-3-yl-CH2-X1 | 418 |
| A-95 | 4-(dimethylamino)phenyl-CH2-X1 | 408 |
| A-96 | benzothiophen-3-yl-CH2-X1 | 421 |
| A-97 | benzo[1,3]dioxol-5-yl-CH2-X1 | 409 |
| A-98 | pyrazin-2-yl-X1 | 353 |
| A-99 | 1H-pyrrol-2-yl-X1 | 340 |
| A-100 | 1H-indol-3-yl-CH(NH2)-X1 | 419 |
| A-101 | pyridin-3-yl-CH2-CH(NH2)-X1 | 395 |
| A-102 | pyridin-4-yl-CH2-CH(NH2)-X1 | 395 |
| A-103 | 4-(dimethylaminomethyl)phenyl-CH2-X1 | 422 |
| A-104 | 4-(methylamino)phenyl-CH2-X1 | 408 |
| A-105 | 1-(isatin-1-yl)-CH2-X1 | 434 |
| A-106 | purin-9-yl-CH2-X1 | 407 |
| A-107 | 1,2,3,4-tetrahydroquinolin-1-yl-CH2-X1 | 420 |
| A-108 | 1H-benzotriazol-1-yl-CH2-X1 | 406 |
| A-109 | 2H-benzotriazol-2-yl-CH2-X1 | 406 |

TABLE 2-17

| Compound No. | W1 | [M+H]+ |
|---|---|---|
| A-110 | indol-1-yl-CH2-X1 | 404 |
| A-111 | benzimidazol-1-yl-CH2-X1 | 405 |
| A-112 | 2-amino-benzimidazol-1-yl-CH2-X1 | 420 |
| A-113 | (R)-1-phenyl-1-(dimethylamino)methyl-X1 | 408 |

TABLE 2-17-continued

| Compound No. | W1 | [M+H]+ |
|---|---|---|
| A-114 | (benzyl with CH(X₁)-N(CH₃)₂) | 422 |
| A-115 | (pyridin-2-yl-CH₂-CH(X₁)-NH₂) | 395 |
| A-116 | (5-fluoro-1H-indol-3-yl-CH₂-X₁) | 422 |
| A-117 | (5-chloro-1H-indol-3-yl-CH₂-X₁) | 438 |
| A-118 | (3-(dimethylamino)benzyl-X₁) | 408 |
| A-119 | (1H-tetrazol-5-yl-CH₂-X₁) | 357 |
| A-120 | (purin-7-yl-CH₂-X) | 407 |
| A-121 | (4-hydroxystyryl-X₁) | 393 |
| A-122 | (4-hydroxyphenethyl-X₁) | 395 |
| A-123 | (3-hydroxybenzyl-X₁) | 381 |
| A-124 | (4-hydroxybenzyl-X₁) | 381 |
| A-125 | (3-hydroxystyryl-X₁) | 393 |
| A-126 | (2H-tetrazol-2-yl-CH₂-X₁) | 357 |
| A-127 | (1H-tetrazol-1-yl-CH₂-X₁) | 357 |
| A-128 | (2-hydroxyphenethyl-X₁) | 395 |
| A-129 | (4-carboxybenzyl-X₁) | 409 |
| A-130 | (3-((dimethylamino)methyl)benzyl-X₁) | 408 |
| A-131 | (caffeine-N7-CH₂-X₁) | 467 |
| A-132 | (3H-imidazo[4,5-b]pyridin-3-yl-CH₂-X₁) | 406 |
| A-133 | (3H-[1,2,3]triazolo[4,5-b]pyridin-3-yl-CH₂-X₁) | 406 |

TABLE 2-18
| Compound No. | W1 | [M+H]+ |
|---|---|---|
| A-134 | 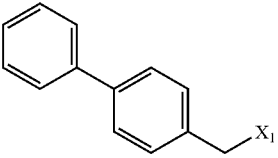 | 441 |
| A-135 | 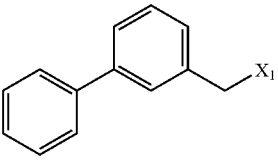 | 441 |
| A-136 | 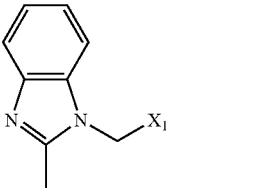 | 419 |
| A-137 | 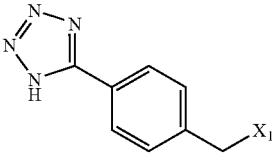 | 433 |
| A-138 | 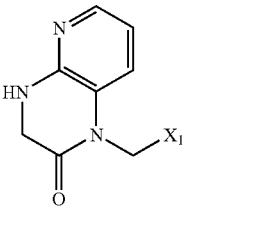 | 436 |
| A-139 | 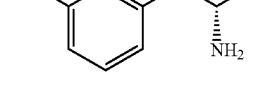 | 439 |
| A-140 | 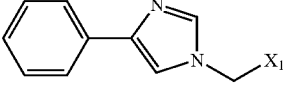 | 431 |
| A-141 | 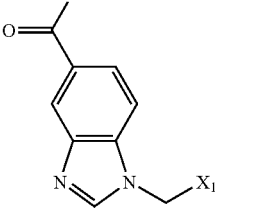 | 449 |
TABLE 2-18-continued
| Compound No. | W1 | [M+H]+ |
|---|---|---|
| A-142 | 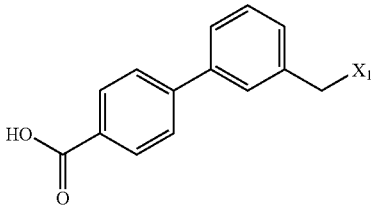 | 485 |
| A-143 | 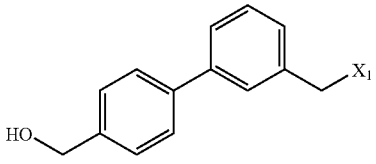 | 471 |
| A-144 | 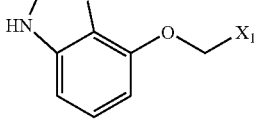 | 421 |
| A-145 | 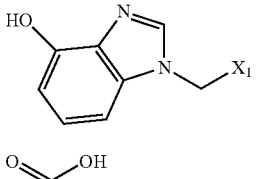 | 421 |
| A-146 | 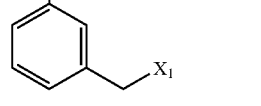 | 409 |
| A-147 | 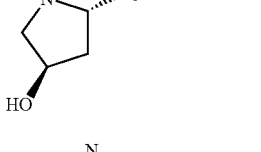 | 360 |
| A-148 | 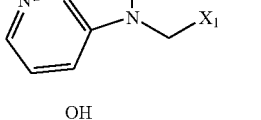 | 407 |
| A-149 | 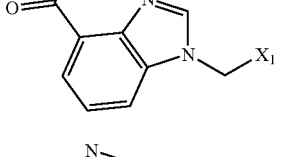 | 449 |
| A-150 | 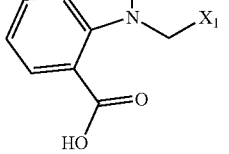 | 449 |

TABLE 2-18-continued

| Compound No. | W1 | [M+H]+ |
|---|---|---|
| A-151 | (methyl benzimidazole carboxylate-CH2-X1) | 463 |
| A-152 | (benzimidazole methyl carboxylate-CH2-X1) | 463 |
| A-153 | (3'-carboxybiphenyl-CH2-X1) | 485 |
| A-154 | (4-carbamoylphenyl-CH2-X1) | 408 |
| A-155 | (4-(hydroxycarbamoyl)phenyl-CH2-X1) | 424 |
| A-156 | (4-(dimethylcarbamoyl)phenyl-CH2-X1) | 436 |
| A-157 | (4-(ethylcarbamoyl)phenyl-CH2-X1) | 436 |

TABLE 2-19

| Compound No. | W1 | [M+H]+ |
|---|---|---|
| A-158 | (3-(1H-tetrazol-5-yl)phenyl-CH2-X1) | 433 |
| A-159 | (4-(hydroxymethyl)phenyl-imidazole-CH2-X1) | 461 |
| A-160 | (3-(methylthio)phenyl-CH2-X1) | 411 |
| A-161 | (4-(methylthio)phenyl-CH2-X1) | 411 |
| A-162 | (3-(carboxymethyl)phenyl-CH2-X1) | 423 |
| A-163 | (4-(carboxymethyl)phenyl-CH2-X1) | 423 |
| A-164 | (pyrido-pyrazinone-CH2-X1) | 450 |
| A-165 | (pyrido-pyrazinone-CH2-X1) | 450 |
| A-166 | (4-((2-(dimethylamino)ethyl)carbamoyl)phenyl-CH2-X1) | 479 |
| A-167 | (4-((4-methylpiperazin-1-yl)carbonyl)phenyl-CH2-X1) | 491 |

TABLE 2-19-continued

| Compound No. | W1 | [M+H]+ |
|---|---|---|
| A-168 | (HO-CH2CH2)2N-C(=O)-C6H4-CH2-X1 | 496 |
| A-169 | 2-methyl-1,8-naphthyridin-3-yl-X1 | 417 |
| A-170 | 2-methyl-1,2,3,4-tetrahydro-1,8-naphthyridin-3-yl-X1 | 421 |
| A-171 | 1,8-naphthyridin-2-yl-CH2CH2-X1 | 431 |
| A-172 | 2-methyl-1,8-naphthyridin-3-yl-CH2-X1 | 431 |
| A-173 | 4-(methoxycarbonyl)-1H-imidazol-1-yl-CH2-X1 | 413 |
| A-174 | naphthalen-1-yl-CH2-X1 | 415 |
| A-175 | naphthalen-2-yl-CH2-X1 | 415 |
| A-176 | phenyl(1H-imidazol-1-yl)CH-X1 | 431 |

TABLE 2-19-continued

| Compound No. | W1 | [M+H]+ |
|---|---|---|
| A-177 | 7-methyl-1,2,3,4-tetrahydro-1,8-naphthyridin-6-yl-CH2-X1 | 435 |
| A-178 | 1,2,3,4-tetrahydro-1,8-naphthyridin-7-yl-CH2-X1 | 421 |

TABLE 2-20

W1-C(=O)-NH-CH2-C*H(iPr)-NH-C6H4-CF3

| Compound No. | W1 | [M+H]+ |
|---|---|---|
| A-179 | pyridin-2-yl-CH2-X1 | 366 |
| A-180 | pyridin-3-yl-CH2-X1 | 366 |
| A-181 | pyridin-4-yl-CH2-X1 | 366 |
| A-182 | 1-(pyridin-4-yl)piperidin-4-yl-X1 | 435 |

TABLE 2-21

W1-C(=O)-NH-C*H(iPr)-CH2-NH-C6H4-CF3

| Compound No. | W1 | [M+H]+ |
|---|---|---|
| A-183 | phenyl-CH2-X1 | 365 |

TABLE 2-22

| Compound No. | W1 | W2 | W3 | [M+H]+ |
|---|---|---|---|---|
| A-184 | benzyl-X1 | Me X2 | X3 H | 379 |
| A-185 | 4-(dimethylamino)benzyl-X1 | Me X2 | X3 H | 422 |
| A-186 | (1H-indol-3-yl)methyl-X1 | Me X2 | X3 H | 418 |
| A-187 | (pyridin-4-yl)methyl-X1 | Me X2 | X3 H | 380 |
| A-188 | benzyl-X1 | H X2 | X3 Me | 379 |

TABLE 2-23

| Compound No. | W1 | Configuration of * carbon | [M+H]+ |
|---|---|---|---|
| A-189 | phenyl-X1 | R | 349 |
| A-190 | phenethyl-X1 | R | 377 |
| A-191 | pyridin-2-yl-X1 | R | 350 |

TABLE 2-23-continued

| Compound No. | W1 | Configuration of * carbon | [M+H]+ |
|---|---|---|---|
| A-192 | piperidin-4-yl-X1 | R | 356 |
| A-193 | (2-amino-(1H-indol-3-yl)methyl)-X1 | R | 417 |
| A-194 | 3-(dimethylamino)benzyl-X1 | R | 406 |
| A-195 | 4-(dimethylamino)benzyl-X1 | R | 406 |
| A-196 | quinolin-6-yl-X1 | R | 400 |
| A-197 | (pyridin-4-yl)methyl-X1 | R | 364 |
| A-198 | (pyridin-3-yl)methyl-X1 | R | 364 |
| A-199 | (1-isopropylpiperidin-4-yl)methyl-X1 | R | 412 |
| A-200 | 1-(pyridin-4-yl)piperidin-4-yl-X1 | S | 433 |

TABLE 2-23-continued

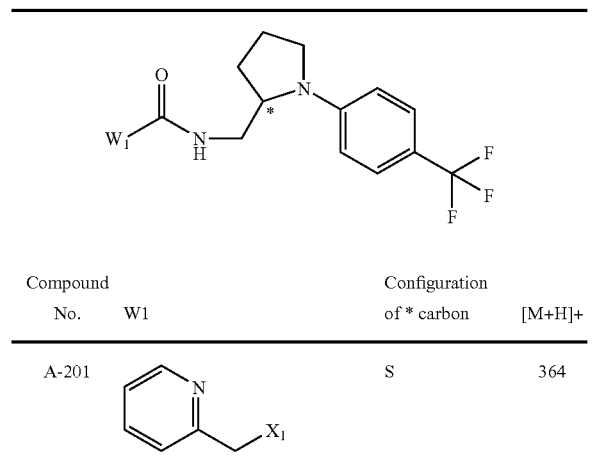

| Compound No. | W1 | Configuration of * carbon | [M+H]+ |
|---|---|---|---|
| A-201 | pyridin-2-ylmethyl-X1 | S | 364 |

TABLE 2-24

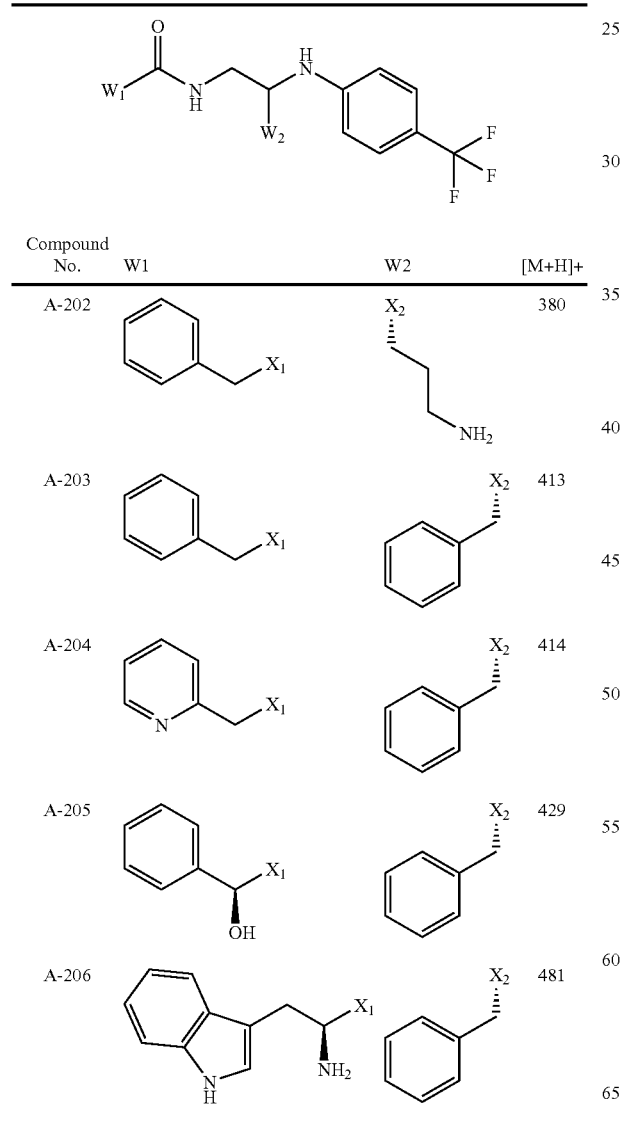

| Compound No. | W1 | W2 | [M+H]+ |
|---|---|---|---|
| A-202 | benzyl-X1 | X2-CH2CH2CH2-NH2 | 380 |
| A-203 | benzyl-X1 | benzyl-X2 | 413 |
| A-204 | pyridin-2-ylmethyl-X1 | benzyl-X2 | 414 |
| A-205 | α-hydroxybenzyl-X1 | benzyl-X2 | 429 |
| A-206 | tryptophanyl-X1 (NH2) | benzyl-X2 | 481 |

TABLE 2-24-continued

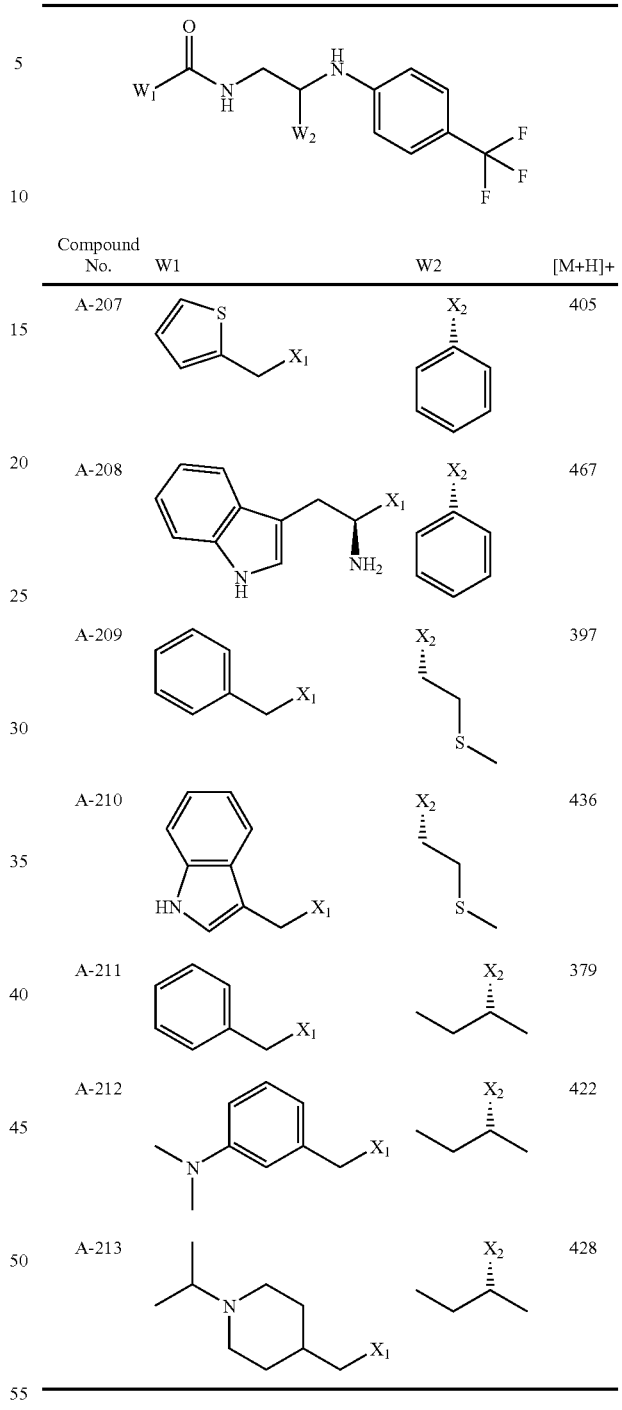

| Compound No. | W1 | W2 | [M+H]+ |
|---|---|---|---|
| A-207 | thiophen-2-ylmethyl-X1 | phenyl-X2 | 405 |
| A-208 | tryptophanyl-X1 (NH2) | phenyl-X2 | 467 |
| A-209 | benzyl-X1 | X2-CH2CH2-S-CH3 | 397 |
| A-210 | (1H-indol-3-yl)methyl-X1 | X2-CH2CH2-S-CH3 | 436 |
| A-211 | benzyl-X1 | sec-butyl-X2 | 379 |
| A-212 | 3-(dimethylamino)benzyl-X1 | sec-butyl-X2 | 422 |
| A-213 | (1-isopropylpiperidin-4-yl)methyl-X1 | sec-butyl-X2 | 428 |

TABLE 2-25

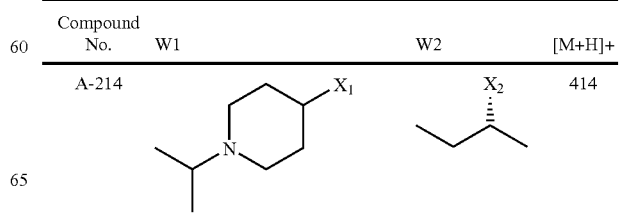

| Compound No. | W1 | W2 | [M+H]+ |
|---|---|---|---|
| A-214 | 1-isopropylpiperidin-4-yl-X1 | sec-butyl-X2 | 414 |

TABLE 2-25-continued

| Compound No. | W1 | W2 | [M+H]+ |
|---|---|---|---|
| A-215 | 1-(pyridin-4-yl)piperidin-4-yl-X₁ | sec-butyl-X₂ | 449 |
| A-216 | (1H-indol-3-yl)methyl-X₁ | sec-butyl-X₂ | 418 |
| A-217 | benzo[d][1,3]dioxol-5-ylmethyl-X₁ | sec-butyl-X₂ | 423 |
| A-218 | 4-(dimethylamino)benzyl-X₁ | sec-butyl-X₂ | 422 |
| A-219 | 2-amino-2-(1H-indol-3-yl)ethyl-X₁ | sec-butyl-X₂ | 447 |

TABLE 2-26

W₁-C(=O)-NH-CH₂CH₂-CH(iPr)-NH-C₆H₄-CF₃

| Compound No. | W1 | [M+H]+ |
|---|---|---|
| A-220 | benzyl-X₁ | 379 |
| A-221 | pyridin-2-ylmethyl-X₁ | 380 |
| A-222 | 4-(dimethylamino)benzyl-X₁ | 422 |
| A-223 | 3-(dimethylamino)benzyl-X₁ | 422 |

TABLE 2-26-continued

W₁-C(=O)-NH-CH₂CH₂-CH(iPr)-NH-C₆H₄-CF₃

| Compound No. | W1 | [M+H]+ |
|---|---|---|
| A-224 | 4-(dimethylamino)benzyl-X₁ | 422 |

TABLE 2-27

W₁-C(=O)-NH-CH₂-CH(iPr)-NH-C₆H₃(CH₂NMe₂)(CF₃)

| Compound No. | W1 | [M+H]+ |
|---|---|---|
| A-225 | benzyl-X₁ | 422 |

TABLE 2-28

W₁-pyrrolidin-3-yl-N(C₆H₄CF₃)

| Compound No. | W1 | [M+H]+ |
|---|---|---|
| B-9 | 2-(pyridin-2-yl)acetamido-X₁ | 351 |
| B-10 | 2-phenylacetamido-X₁ | 350 |
| B-11 | 2-(pyridin-2-yl)acetamido-X₁ | 351 |

TABLE 2-28-continued

[Structure: W1-pyrrolidinyl-phenyl-CF3]

| Compound No. | W1 | [M+H]+ |
|---|---|---|
| A-12 | [pyridinyl-piperidinyl-C(=O)-NH-X1] | 420 |

TABLE 2-29

[Structure: W1-CH2-C(=O)-pyrrolidinyl-phenyl-CF3]

| Compound No. | W1 | [M+H]+ |
|---|---|---|
| C-44 | [phenyl-CH2CH2-NH-X1] | 377 |
| C-45 | [benzyl-NH-X1] | 363 |
| C-46 | [pyridin-2-yl-CH2CH2-NH-X1] | 378 |
| C-47 | [pyridin-2-yl-CH2-NH-X1] | 364 |
| C-48 | [benzo[1,3]dioxol-5-yl-CH2-NH-X1] | 407 |
| C-49 | [pyridin-3-yl-CH2-NH-X1] | 364 |

TABLE 2-29-continued

[Structure: W1-CH2-C(=O)-pyrrolidinyl-phenyl-CF3]

| Compound No. | W1 | [M+H]+ |
|---|---|---|
| C-50 | [pyridin-4-yl-CH2-NH-X1] | 364 |
| C-51 | [pyrimidin-2-yl-piperazinyl-X1] | 420 |
| C-52 | [2-chlorophenyl-piperazinyl-X1] | 452 |
| C-53 | [3-hydroxyphenyl-piperazinyl-X1] | 434 |
| C-54 | [2-hydroxyphenyl-piperazinyl-X1] | 434 |
| C-55 | [4-(dimethylamino)piperidinyl-X1] | 384 |
| C-56 | [4-hydroxyphenyl-piperazinyl-X1] | 434 |
| C-57 | [4-hydroxy-4-phenylpiperidinyl-X1] | 433 |

TABLE 2-29-continued

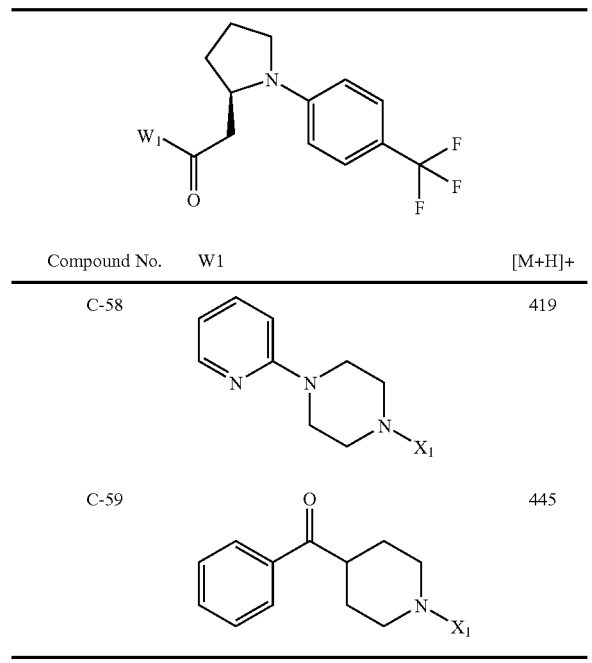

| Compound No. | W1 | [M+H]+ |
|---|---|---|
| C-58 | (2-pyridyl-piperazinyl-X₁) | 419 |
| C-59 | (benzoyl-piperidinyl-X₁) | 445 |

TABLE 2-30

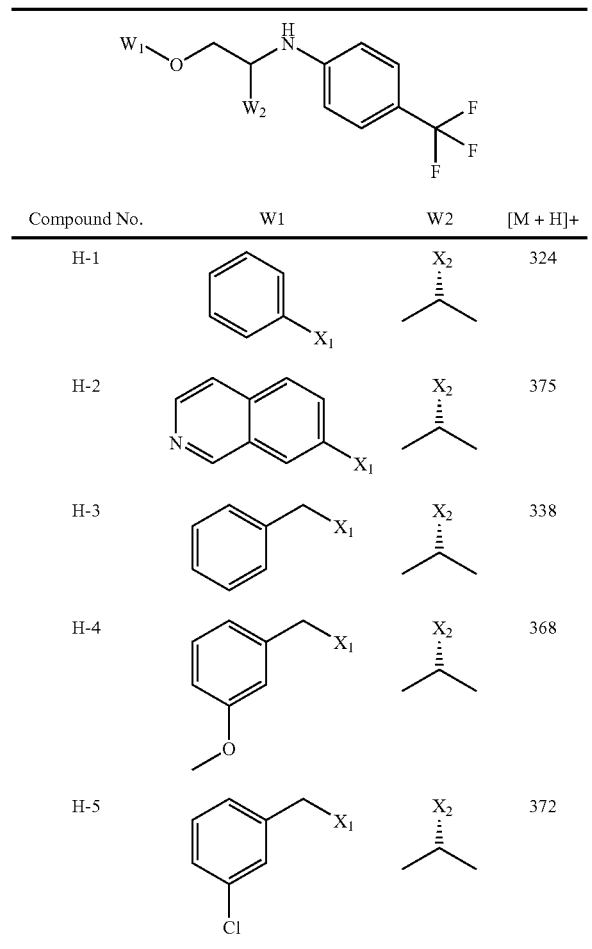

| Compound No. | W1 | W2 | [M + H]+ |
|---|---|---|---|
| H-1 | phenyl-X₁ | isopropyl-X₂ | 324 |
| H-2 | isoquinolinyl-X₁ | isopropyl-X₂ | 375 |
| H-3 | benzyl-X₁ | isopropyl-X₂ | 338 |
| H-4 | 3-methoxybenzyl-X₁ | isopropyl-X₂ | 368 |
| H-5 | 3-chlorobenzyl-X₁ | isopropyl-X₂ | 372 |

TABLE 2-30-continued

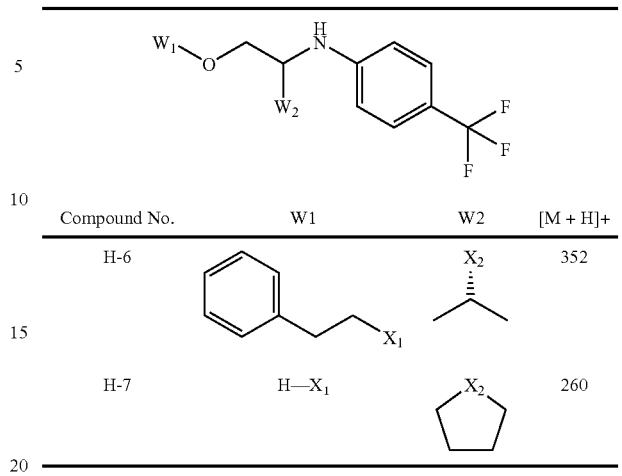

| Compound No. | W1 | W2 | [M + H]+ |
|---|---|---|---|
| H-6 | phenethyl-X₁ | isopropyl-X₂ | 352 |
| H-7 | H—X₁ | cyclopentyl-X₂ | 260 |

Experimental Example 1

Measurement of tissue kallikrein inhibitory activity

Expression and purification of human activated tissue kallikrein was performed according to the method of Angermann (A. Angermann et al., *Eur. J. Biochem.*, 206, 225-233 (1992)). That is, a gene was prepared by adding 6 residues of histidine to the C-terminal side of human pancreas kallikrein gene (D. Fukuchima et al, *Biochemistry,* 24, 8037-8043 (1985)), and tissue prokallikrein was expressed by a system using a baculovirus-insect cell (Sf21). Purified human tissue kallikrein was obtained from the culture supernatant by purification using a nickel chelate column (Ni-NTA, QIAGEN K. K.), digestion with TPCK trypsin and further nickel chelate column. To a solution (100 µL) of the human activated tissue kallikrein adjusted to 0.0625 µg/mL with an assay buffer (100 mM tris-hydrochloride buffer (pH 8.4) containing 0.2M NaCl, 0.02% Tween 20, and 0.1% PEG 6000) was added an assay buffer (containing 2% DMSO) solution (50 µL) of the test compound adjusted to the objective concentration, and the mixture was incubated at 37° C. for 10 minutes (min=minutes). Then, a 4 mM solution (50 µL) of D-valyl-L-leucyl-L-arginyl-p-nitroanilide hydrochloride (BACHEM AG) adjusted with the assay buffer was added, the absorbance was measured and the reaction rate was determined. As a control, a DMSO solution (50 µL) was added instead of the solution of the test compound. Absorbance was measured at a wavelength of 405 nm at 60 second intervals for 90 min using a Benchmark Plus Microplate Reader (BIO RAD). The negative logarithm value (abbreviated as $pIC_{50}$) of the test compound concentration when the activated tissue kallikrein activity (initial rate) was inhibited by 50% without addition of the test compound was used as an index of the activated tissue kallikrein inhibitory activity. The activated tissue kallikrein inhibitory activity of the representative compounds is shown in Table 3.

TABLE 3

| Compound No. | pIC50 |
|---|---|
| A-1 | 7.66 |
| A-3 | 7.59 |
| A-4 | 7.53 |
| A-5 | 7.30 |
| A-6 | 7.24 |
| A-7 | 7.07 |
| A-8 | 7.04 |

TABLE 3-continued

| Compound No. | pIC50 |
|---|---|
| A-9 | 6.99 |
| A-10 | 6.84 |
| A-11 | 6.80 |
| A-12 | 6.79 |
| A-13 | 6.75 |
| A-14 | 6.74 |
| A-15 | 6.74 |
| A-16 | 6.58 |
| A-17 | 6.53 |
| A-18 | 6.51 |
| A-39 | 7.38 |
| A-40 | 6.61 |
| A-41 | 6.68 |
| A-47 | 6.68 |
| A-48 | 7.33 |
| A-49 | 7.33 |
| A-50 | 6.97 |
| A-51 | 6.89 |
| A-52 | 6.82 |
| A-55 | 7.70 |
| A-56 | 7.30 |
| A-57 | 7.44 |
| A-58 | 7.31 |
| A-59 | 7.08 |
| A-60 | 6.87 |
| B-2 | 6.69 |
| C-40 | 7.19 |
| C-41 | 6.52 |
| C-42 | 6.89 |
| C-43 | 7.04 |
| E-2 | 6.95 |
| E-3 | 6.61 |
| E-4 | 6.59 |
| E-6 | 6.60 |

Experimental Example 2

Efficacy evaluation in acetic acid writhing model

The acetic acid writhing model was subjected to evaluation according to the method of *European Journal of Pharmacology*, 352, 47-52 (1998). To be specific, a solution of the test compound adjusted to the objective concentration with a 0.5 (w/v) % tragacanth gum solution was orally administered to male ICR mice (CHARLES RIVER LABORATORIES JAPAN, INC.) at 5 mL/kg, and a 0.9% acetic acid solution adjusted with a physiological saline was intraperitoneally administered 60 min later at 5 mL/kg. The number of writhing for 15 min from 5 min to 20 min after administration of a 0.9% acetic acid solution was counted and taken as the writhing number of the test compound. A mouse, to which a 0.5 (w/v) % tragacanth gum (TG) solution was orally administered at 5 ml/kg instead of the test compound, was used as a control. The suppression rate (%) was calculated by subtracting the relative value of each mouse from the relative value when the average value of the control group is 100%. The results of acetic acid writhing suppression of the representative compounds are shown in Table 4. As a Reference Example, the value obtained by oral administration of a positive control drug, indomethacin, instead of the test compound is shown. The data show mean value±standard error. For testing the significant difference, Dunnett's t-test was used, and statistic significance as shown by P<0.05 and P<0.01 relative to the TG control group is shown in the Table with * and **, respectively.

TABLE 4

Acetic acid writhing suppression effect of the compound of the present invention

| treatment | dose (oral) | suppression rate (%) |
|---|---|---|
| Control (0.5(w/v)% TG solution) | — | 0 ± 8.0 |
| compound E-6 | 3 mg/kg | 58.7 ± 7.0** |
|  | 10 mg/kg | 58.7 ± 5.8** |
|  | 30 mg/kg | 64.9 ± 8.3** |
| compound A-8 | 3 mg/kg | 33.7 ± 10.1* |
|  | 10 mg/kg | 52.7 ± 7.5** |
|  | 30 mg/kg | 63.5 ± 6.6** |
| Indomethacin (positive control) | 10 mg/kg | 64.1 ± 10.8** |

Experimental Example 3

Efficacy evaluation in DSS-induced enteritis model

The dextran sodium sulfate (DSS)-induced enteritis model was subjected to evaluation by a partly-modified methods of *Gastroenterology*, 98, 694-702 (1990) and *Cytokine*, 11, 890-896 (1998). A 5 (w/v) % DSS (manufactured by Sigma, MW 5,000) solution was freely taken by female CBA mice (CHARLES RIVER LABORATORIES JAPAN, INC.) for a given period to induce enteritis. A solution of the test compound adjusted to the objective concentration with a 0.5 (w/v) % tragacanth gum (TG) solution was orally administered at 5 mL/kg. Upon autopsy, the length, weight and the like of the large intestine were evaluated and used as an index of the onset of inflammatory enteritis. As a control, a mouse, to which a 0.5 (w/v) % TG solution was orally administered at 5 mL/kg instead of the test compound, was used. The length and weight of the large intestine are expressed as the relative value when the average value of the non-treatment group is 100%. The results of suppression by the representative compound in the DSS induced enteritis model are shown in Table 5. As a Reference Example, the values obtained by oral administration of a positive control drug, salazosulfapyridine, instead of the test compound are shown. The data show mean value±standard error. For testing the significant difference, Dunnett's t-test was used, and statistic significance as shown by P<0.05 and P<0.01 relative to the TG control group is shown in the Table with * and **, respectively.

TABLE 5

DSS enteritis improving effect by the compound of the present invention

| treatment | dose (oral) | large intestine length (%) | large intestine weight (%) |
|---|---|---|---|
| without treatment | — | 100.0 ± 1.3 | 100.0 ± 2.8 |
| control (0.5 (w/v) % TG solution) | — | 72.4 ± 1.1 | 146.3 ± 4.2 |
| Compound E-6 | 10 mg/kg | 85.2 ± 2.4** | 117.5 ± 5.1** |
|  | 30 mg/kg | 87.9 ± 2.0** | 110.7 ± 4.1** |
| Compound A-8 | 10 mg/kg | 80.4 ± 1.8** | 130.5 ± 5.28** |
| salazosulfapyridine (positive control) | 200 mg/kg | 78.1 ± 1.5* | 123.0 ± 1.9** |

INDUSTRIAL APPLICABILITY

The aniline derivative or a salt thereof the present invention has a kininogenase activity inhibitory action, and is effective as an agent for the prophylaxis or treatment of various diseases (gastrointestinal tract disease, inflammatory disease, allergic disease, pain, edematous disease, cell proliferative disease, inflammatory bowel disease, irritable bowel syndrome, pancreatitis, asthma etc.) for which inhibition of kininogenase is considered to be effective.

The invention claimed is:

1. A compound represented by the formula (A):

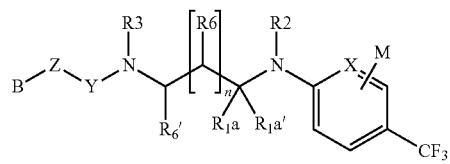

(A)

wherein

X is a carbon atom;

M is selected from the group consisting of a hydrogen atom, a halogeno group, a lower alkyl group optionally having substituent(s), —(CH$_2$)$_m$ORa, —CH(ORa)(ORa'), —(CH$_2$)$_m$NRaRa', —(CH$_2$)$_m$CO$_2$Ra, —(CH$_2$)$_m$CONRaRa', —CH=CHCO$_2$Ra, —(CH$_2$)$_m$COCO$_2$Ra, and —(CH$_2$)$_m$PO(ORa)(ORa')

wherein m is an integer of 0 to 2, and

Ra and Ra' are each independently selected from the group consisting of a hydrogen atom and a lower alkyl group;

Z is selected from the group consisting of a single bond, —CH(Rb)—, —CH(Rb)—CH(Rb')—, —CH=CH—, and —C(O)— wherein

Rb and Rb' are each independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -QR10 wherein

Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$—, and —R11S(O)$_p$— wherein p is an integer of 0 to 2, and

R10 and R11 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and an acyl group, or R10 and R11 are optionally bonded to form a ring;

B is selected from the group consisting of a hydrogen atom, a lower alkyl group optionally having substituent(s), and a group represented by the formula (D):

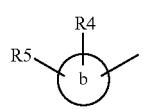

(D)

wherein ring b is selected from the group consisting of a cycloalkyl group, a heterocyclic group, and an aryl group, and R4 and R5 are each independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -Q'R20 wherein

Q' is selected from the group consisting of —O—, —S(O)$_{p'}$—, —S(O)$_p$O—, —NH—, —NR21-, —C(=O)—, —C(=O)O—, —C(=O)NH—, —C(=O)NR21-, —S(O)$_p$NH—, —S(O)$_p$NR21-, —NHC(=O)—, —NR21C(=O)—, —NHS(O)$_{p'}$—, and —NR21S(O)$_{p'}$— wherein p' is an integer of 0 to 2, and

R20 and R21 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), an acyl group, and a hydroxyl group, or R20 and R21 are optionally bonded to form a ring;

R3 is selected from the group consisting of a hydrogen atom, a lower alkyl group optionally having substituent(s) and an aryl group optionally having substituent(s), or R3 is optionally bonded to B to form a nitrogen-containing 5- or 6-membered ring, wherein said nitrogen-containing 5- or 6-membered ring optionally further contains a heteroatom in the ring in addition to the nitrogen atom, and wherein said nitrogen-containing 5- or 6-membered ring is optionally substituted by substituent(s) selected from the group consisting of a hydroxy group, an alkylamino group, an acyl group, a heterocyclic group optionally having substituent(s), and an aryl group optionally having substituent(s);

Y is —C(O)— or —SO$_2$—;

R$_1$a is a lower alkyl group optionally having substituent(s) or an aryl group optionally having substituent(s), and R$_1$a' is a hydrogen atom; or R$_1$a and R$_1$a' are bonded to form a 3- to 6-membered ring, wherein said 3- to 6-membered ring optionally contains a heteroatom in the ring and optionally having substituent(s), R2 is a hydrogen atom or a lower alkyl group, or R$_1$a (or R$_1$a') and R2 are optionally bonded to form a 5- or 6-membered ring, wherein said 5- or 6- membered ring optionally contains a heteroatom in the ring and optionally having substituent(s);

n is 0 or 1; and

R6 and R$_6$' are each independently selected from the group consisting of a hydrogen atom, a lower alkyl group optionally having substituent(s), an amino group, an aminoalkyl group, and an alkoxy group;

or a pharmaceutically acceptable salt thereof.

2. The compound of claim 1, which is represented by the formula (A):

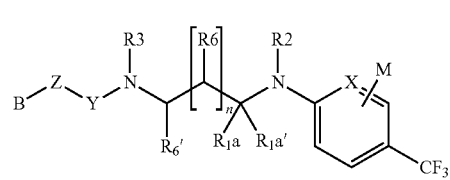

(A)

wherein

X is a carbon atom;

M is selected from the group consisting of a hydrogen atom, a halogeno group, a lower alkyl group optionally having substituent(s), —(CH$_2$)$_m$ORa, —CH(ORa)(ORa'), —(CH$_2$)$_m$NRaRa', —(CH$_2$)$_m$CO$_2$Ra, —(CH$_2$)$_m$CONRaRa', —CH=CHCO$_2$Ra, —(CH$_2$)$_m$ COCO$_2$Ra, and —(CH$_2$)$_m$PO(ORa)(ORa')

wherein m is an integer of 0 to 2, and

Ra and Ra' are each independently selected from the group consisting of a hydrogen atom and a lower alkyl group;

Z is selected from the group consisting of a single bond, —CH(Rb)—, —CH(Rb)—CH(Rb')—, and —CH=CH—
wherein
Rb and Rb' are each independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -QR10
wherein
Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$—, and —R11S(O)$_p$—
wherein
p is an integer of 0 to 2, and
R10 and R11 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R10 and R11 are optionally bonded to form a ring;
B is selected from the group consisting of a hydrogen atom, a lower alkyl group optionally having substituent(s), and a group represented by the formula (D):

(D)

wherein
ring b is selected from the group consisting of a cycloalkyl group, a heterocyclic group, and an aryl group, and
R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -Q'R20
wherein
Q' is selected from the group consisting of —O—, —S(O)$_{p'}$—, —S(O)$_p$O—, —NH—, —NR21-, —C(=O)—, —C(=O)O—, —C(=O)NH—, —C(=O)NR21-, —S(O)$_p$NH—, —S(O)$_p$NR21-, —NHC(=O)—, —NR21C(=O)—, —NHS(O)$_p$—, and —NR21S(O)$_{p'}$—
wherein
p' is an integer of 0 to 2, and
R20 and R21 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s) and an acyl group, or R20 and R21 are optionally bonded to form a ring;
R3 is selected from the group consisting of a hydrogen atom and a lower alkyl group;
Y is —C(O)— or —SO$_2$—;
R$_1$a is a lower alkyl group optionally having substituent(s) and R$_1$a' is a hydrogen atom; or R$_1$a and R$_1$a' are bonded to form a 3- to 6-membered ring, wherein said 3- to 6-membered ring optionally contains a heteroatom in the ring and optionally having substituent(s);
R2 is a hydrogen atom or a lower alkyl group, or R$_1$a (or R$_1$a') and R2 are optionally bonded to form a 5- or 6-membered ring, wherein said 5- or 6- membered ring optionally contains a heteroatom in the ring) and optionally having substituent(s);
n is 0 or 1; and
R6 and R$_6$' are each independently selected from the group consisting of a hydrogen atom, a lower alkyl group optionally having substituent(s), an amino group, an aminoalkyl group, and an alkoxy group;
or a pharmaceutically acceptable salt thereof.

3. The compound of claim 2, wherein B is a group represented by the formula (D), or a pharmaceutically acceptable salt thereof.

4. The compound of claim 2, wherein M is selected from the group consisting of a hydrogen atom, a halogeno group, a lower alkyl group optionally having substituent(s), —(CH$_2$)$_m$ORa, —(CH$_2$)$_m$NRaRa', —(CH$_2$)$_m$CO$_2$Ra, and —CH=CHCO$_2$Ra wherein m is an integer of 0 to 2, and Ra and Ra' are each independently selected from the group consisting of a hydrogen atom and a lower alkyl group, or a pharmaceutically acceptable salt thereof.

5. The compound of claim 1, wherein B is a group represented by the formula (D), or a pharmaceutically acceptable salt thereof.

6. The compound of claim 1, wherein n is 0, and R2, R3, R6 and R$_6$' are each independently selected from the group consisting of a hydrogen atom and a lower alkyl group optionally having substituent(s), or a pharmaceutically acceptable salt thereof.

7. The compound of claim 1, wherein M is selected from the group consisting of a hydrogen atom, a halogeno group, and a lower alkyl group optionally having substituent(s), or a pharmaceutically acceptable salt thereof.

8. The compound of claim 1, wherein Y is —C(O)—, or a pharmaceutically acceptable salt thereof.

9. The compound of claim 1, wherein Z is a single bond or —CH(Rb)—, or a pharmaceutically acceptable salt thereof.

10. The compound of claim 1, wherein R$_1$a is a lower alkyl group optionally having substituent(s) and R$_1$a' is a hydrogen atom; or R$_1$a and R$_1$a' are bonded to form a 3- to 6-membered ring, wherein said 3- to 6- membered ring optionally contains a heteroatom in the ring and optionally having substituent(s), or a pharmaceutically acceptable salt thereof.

11. The compound of claim 1, wherein B is a group represented by the formula (D), and ring b is selected from the group consisting of a phenyl group, a pyridinyl group, an indolyl group, and a benzimidazolyl group, or a pharmaceutically acceptable salt thereof.

12. The compound of claim 5, wherein n is 0, and R2, R3, R6 and $R_6'$ are each independently selected from the group consisting of a hydrogen atom and a lower alkyl group optionally having substituent(s), or a pharmaceutically acceptable salt thereof.

13. The compound of claim 12, wherein M is selected from the group consisting of a hydrogen atom, a halogeno group, and a lower alkyl group optionally having substituent(s), or a pharmaceutically acceptable salt thereof.

14. The compound of claim 13, wherein B is a group represented by the formula (D), and ring b is selected from the group consisting of a phenyl group, a pyridinyl group, an indolyl group, and a benzimidazolyl group, or a pharmaceutically acceptable salt thereof.

15. A compound represented by the formula (H):

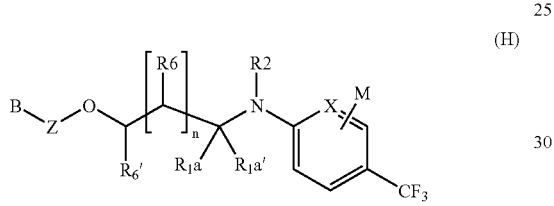

(H)

wherein
X is a carbon atom or a nitrogen atom;
M is selected from the group consisting of a hydrogen atom, a halogeno group, a lower alkyl group optionally having substituent(s), —(CH$_2$)$_m$ORa, —CH(ORa)(ORa'), —(CH$_2$)$_m$NRaRa', —(CH$_2$)$_m$CO$_2$Ra, —(CH$_2$)$_m$CONRaRa', —CH=CHCO$_2$Ra, —(CH$_2$)$_m$COCO$_2$Ra, and —(CH$_2$)$_m$PO(ORa)(ORa')
wherein
m is an integer of 0 to 2, and
Ra and Ra' are each independently selected from the group consisting of a hydrogen atom and a lower alkyl group;
Z is selected from the group consisting of a single bond, —CH(Rb)—, —CH(Rb)—CH(Rb')—, —CH=CH—, and —C(O)—
wherein
Rb and Rb' are each independently selected from the group consisting of a hydrogen atom, a halogeno group, a nitro group, a cyano group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -QR10
wherein
Q is selected from the group consisting of —O—, —S(O)$_p$—, —S(O)$_p$O—, —NH—, —NR11-, —C(=O)—, —C(=O)O—, —C(=O)NH—, —C(=O)NR11-, —S(O)$_p$NH—, —S(O)$_p$NR11-, —NHC(=O)—, —NR11C(=O)—, —NHS(O)$_p$—, and —R11S(O)$_p$—
wherein
p is an integer of 0 to 2, and
R10 and R11 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and an acyl group, or R10 and R11 are optionally bonded to form a ring;
B is selected from the group consisting of a hydrogen atom, a lower alkyl group optionally having substituent(s), and a group represented by the formula (D):

(D)

wherein
ring b is selected from the group consisting of a cycloalkyl group, a heterocyclic group, and an aryl group, and
R4 and R5 are independently selected from the group consisting of a hydrogen atom, a halogeno group, a cyano group, a nitro group, an ammonium group, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), and -Q'R20
wherein
Q' is selected from the group consisting of —O—, —S(O)$_{p'}$—, —S(O)$_{p'}$O—, —NH—, —NR21-, —C(=O)—, —C(=O)O—, —C(=O)NH—, —C(=O)NR21-, —S(O)$_p$NH—, —S(O)$_p$NR21-, —NHC(=O)—, —NR21C(=O)—, —NHS(O)$_{p'}$—, and —NR21S(O)$_{p'}$—
wherein
p' is an integer of 0 to 2, and
R20 and R21 are each independently selected from the group consisting of a hydrogen atom, an alkyl group optionally having substituent(s), an alkenyl group optionally having substituent(s), an alkynyl group optionally having substituent(s), a cycloalkyl group optionally having substituent(s), a heterocyclic group optionally having substituent(s), an aryl group optionally having substituent(s), a cycloalkylalkyl group optionally having substituent(s), a heterocyclylalkyl group optionally having substituent(s), an aralkyl group optionally having substituent(s), an acyl group, and a hydroxyl group, or R20 and R21 are optionally bonded to form a ring;

$R_1a$ is an isopropyl group, an isobutyl group, a sec-butyl group or a tert-butyl group, and $R_1a'$ is a hydrogen group; or $R_1a$ and $R_1a'$ are bonded to form a 3- to 6-membered ring, wherein said 3- to 6- membered ring optionally contains a heteroatom in the ring and optionally having substituent(s);

R2 is a hydrogen atom or a lower alkyl group, or $R_1a$ (or $R_1a'$) and R2 are optionally bonded to form a 5- or 6-membered ring, wherein said 5- or 6- membered ring optionally contains a heteroatom in the ring and optionally having substituent(s);

n is 0 or 1; and

R6 and $R_6'$ are each independently selected from the group consisting of a hydrogen atom, a lower alkyl group optionally having substituent(s), an amino group, an aminoalkyl group, and an alkoxy group, or a pharmaceutically acceptable salt thereof.

16. The compound of claim 15, wherein X is a carbon atom, and B is a group represented by the formula (D), or a pharmaceutically acceptable salt thereof.

17. The compound of claim 15, wherein M is selected from the group consisting of a hydrogen atom, a halogeno group, a lower alkyl group optionally having substituent(s), —(CH$_2$)$_m$ORa, —(CH$_2$)$_m$NRaRa', —(CH$_2$)$_m$CO$_2$Ra, and —CH═CHCO$_2$Ra wherein m is an integer of 0 to 2, and Ra and Ra' are each independently selected from the group consisting of a hydrogen atom and a lower alkyl group, or a pharmaceutically acceptable salt thereof.

18. The compound of claim 17, wherein B is a group represented by the formula (D), and ring b is selected from the group consisting of a phenyl group, a pyridinyl group, an indolyl group, and a benzimidazolyl group, or a pharmaceutically acceptable salt thereof.

19. The compound of claim 18, wherein $R_1a$ is an isopropyl group, an isobutyl group, a sec-butyl group or a tert-butyl group, and $R_1a'$ is a hydrogen group; or $R_1a$ and $R_1a'$ are bonded to form a 3- to 6-membered ring, wherein said 3- to 6-membered ring optionally contains a heteroatom in the ring and optionally having substituent(s), or a pharmaceutically acceptable salt thereof.

20. The compound of claim 19, wherein n is 0, R2, R6 and $R_6'$ are each independently selected from the group consisting of a hydrogen atom and a lower alkyl group optionally having substituent(s), and Z is —CH(Rb)— or —CH(Rb)—CH(Rb')—, or a pharmaceutically acceptable salt thereof.

21. The compound of claim 20, wherein B is a group represented by the formula (D), and ring b is selected from the group consisting of a phenyl group, a pyridinyl group, an indolyl group and a benzimidazolyl group, or a pharmaceutically acceptable salt thereof.

22. A pharmaceutical agent comprising the compound of claim 1, or a pharmaceutically acceptable salt thereof.

23. A pharmaceutical agent comprising, the compound of claim 15, or a pharmaceutically acceptable salt thereof.

24. The pharmaceutical agent of claim 22, wherein said pharmaceutical agent is a kininogenase inhibitor.

25. The pharmaceutical agent of claim 23, wherein said pharmaceutical agent is a kininogenase inhibitor.

26. The pharmaceutical agent of claim 24, wherein said kininogenase is tissue kallikrein.

27. The pharmaceutical agent of claim 25, wherein said kininogenase is tissue kallikrein.

* * * * *

UNITED STATES PATENT AND TRADEMARK OFFICE
CERTIFICATE OF CORRECTION

PATENT NO. : 7,879,863 B2
APPLICATION NO. : 11/537139
DATED : February 1, 2011
INVENTOR(S) : Tokumasu et al.

Page 1 of 1

It is certified that error appears in the above-identified patent and that said Letters Patent is hereby corrected as shown below:

Please amend Claim 2, Column 120, Lines 27-31, as follows:

R2 is a hydrogen atom or a lower alkyl group, or R1a (or R1a') and R2 are optionally bonded to form a 5- or 6-membered ring, wherein said 5- or 6-membered ring optionally contains a heteroatom in the ring and optionally having substituent(s)

Signed and Sealed this
Thirty-first Day of May, 2011

David J. Kappos
*Director of the United States Patent and Trademark Office*

SEQUENCE LISTING

<160> NUMBER OF SEQ ID NOS: 5

<210> SEQ ID NO 1
<211> LENGTH: 16
<212> TYPE: PRT
<213> ORGANISM: Homo sapiens

<400> SEQUENCE: 1

Ser Leu Met Lys Arg Pro Pro Gly Phe Ser Pro Phe Arg Ser Ser Arg
1               5                   10                  15

<210> SEQ ID NO 2
<211> LENGTH: 10
<212> TYPE: PRT
<213> ORGANISM: Homo sapiens

<400> SEQUENCE: 2

Lys Arg Pro Pro Gly Phe Ser Pro Phe Arg
1               5                   10

<210> SEQ ID NO 3
<211> LENGTH: 9
<212> TYPE: PRT
<213> ORGANISM: Homo sapiens

<400> SEQUENCE: 3

Arg Pro Pro Gly Phe Ser Pro Phe Arg
1               5

<210> SEQ ID NO 4
<211> LENGTH: 9
<212> TYPE: PRT
<213> ORGANISM: Homo sapiens

<400> SEQUENCE: 4

Lys Arg Pro Pro Gly Phe Ser Pro Phe
1               5

<210> SEQ ID NO 5
<211> LENGTH: 8
<212> TYPE: PRT
<213> ORGANISM: Homo sapiens

<400> SEQUENCE: 5

Arg Pro Pro Gly Phe Ser Pro Phe
1               5